United States Patent [19]

Mann et al.

[11] Patent Number: 4,590,944

[45] Date of Patent: May 27, 1986

[54] CARDIAC TISSUE STIMULATOR FOR STIMULATING IN THE DDX MODALITY

[76] Inventors: Brian M. Mann, 12079 Beaufait, Northridge, Calif. 91326; Joseph J. Florio, 10805 Wicks St., Sunland, Calif. 91040

[21] Appl. No.: 574,708

[22] Filed: Jan. 27, 1984

[51] Int. Cl.$^4$ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,407,287 | 10/1983 | Herpers | 128/419 PG |
| 4,412,541 | 11/1983 | Schaldach et al. | 128/419 PG |
| 4,452,248 | 6/1984 | Keller, Jr. | 128/419 PG |
| 4,485,818 | 12/1984 | Leckrone et al. | 128/419 PG |

Primary Examiner—William E. Kamm
Attorney, Agent, or Firm—Robert R. Meads; Bryant R. Gold

[57] ABSTRACT

A programmable cardiac stimulator capable of stimulation in the DDX modality having a first sensing system (46) for sensing electrical activity in the atrium, a second sensing system (48) for sensing electrical activity in the ventricle, a pulse generator (24) connected to the first (46) and second (48) sensing system and responsive to electrical activity sensed by these systems (46, 48) for determining the timing for supplying electrical pulses to the atrium and ventricle, for this depolarization and a circuit with the pulse generator (24) for changing the stimulation modality from DDD to DVI when premature ventricular activity is sensed by the second sensing system (46) prior to sensing electrical activity by the first sensing system (48) during the pacer cycle.

7 Claims, 39 Drawing Figures

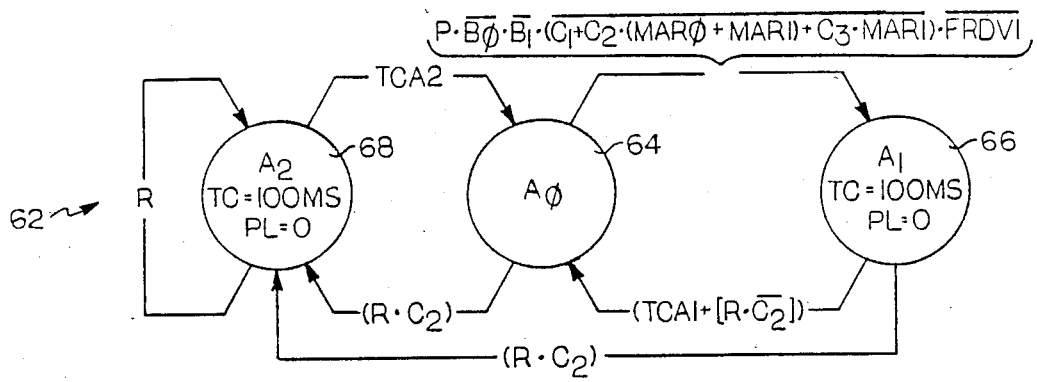
FIGURE 2 ('A' TIMER)
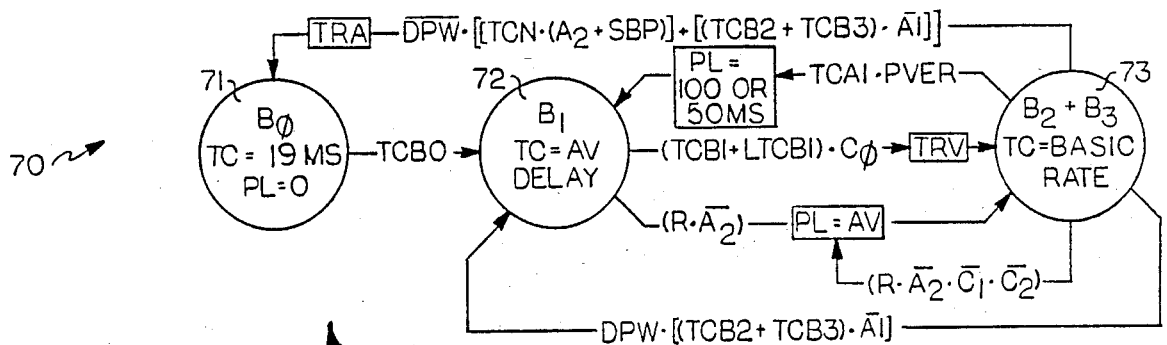
FIGURE 3 ('B' TIMER)
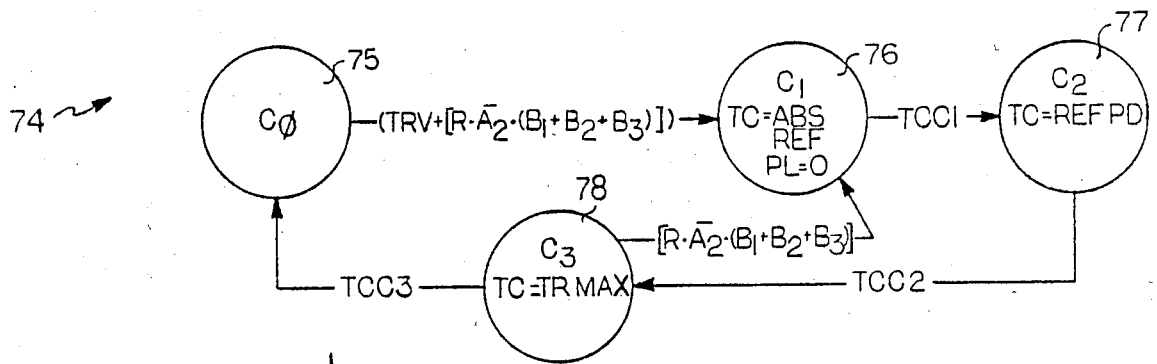
FIGURE 4 ('C' TIMER)
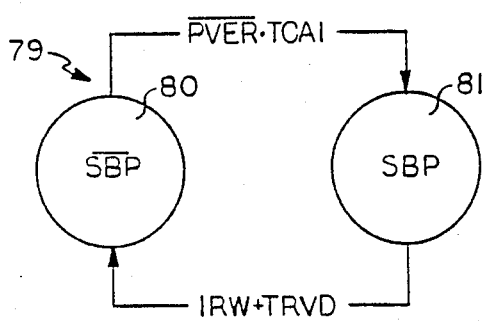
FIGURE 5A
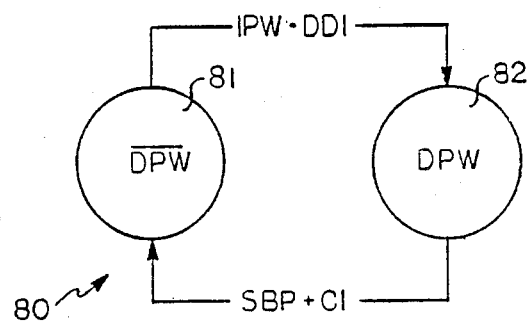
FIGURE 5B

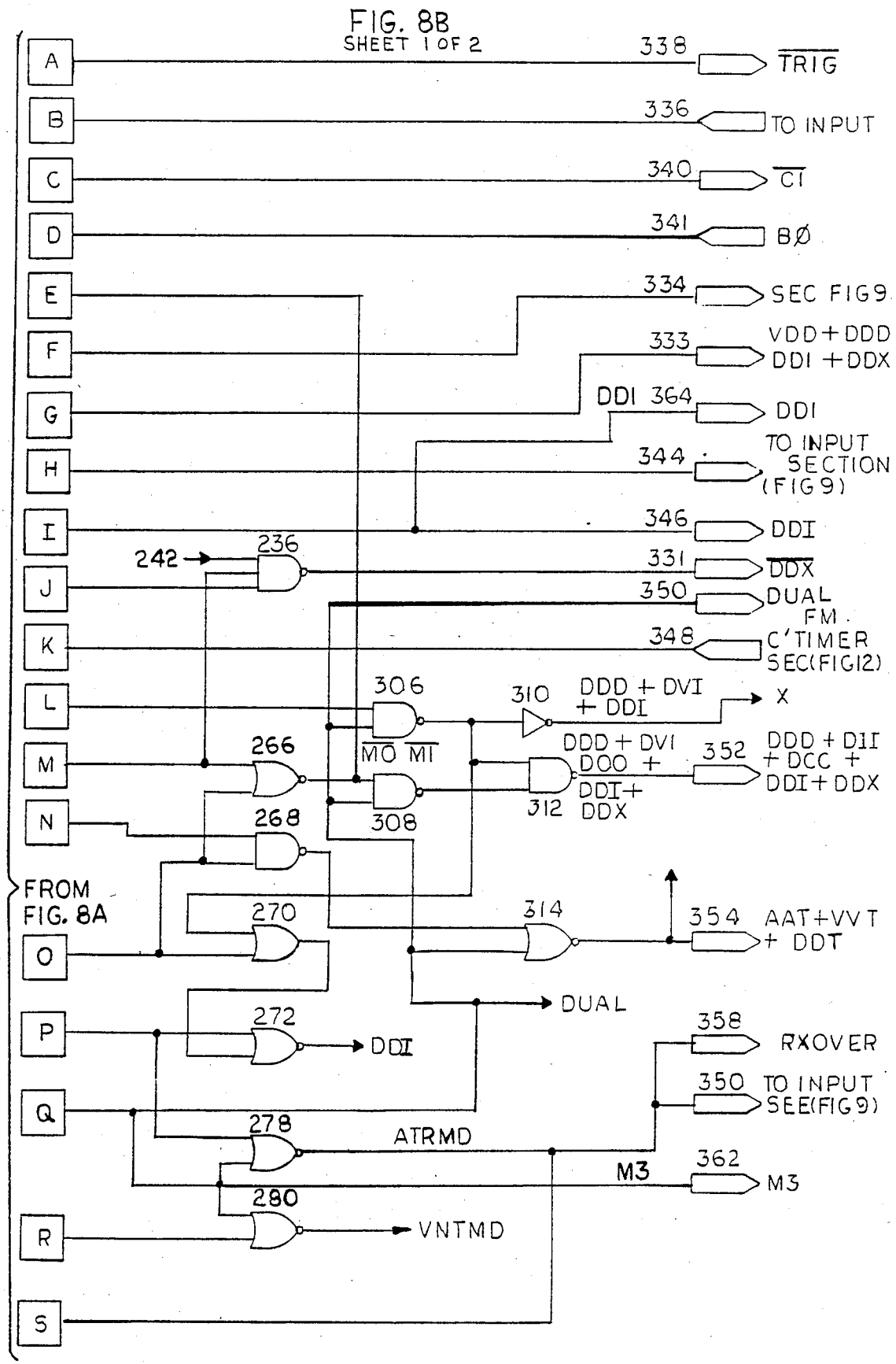

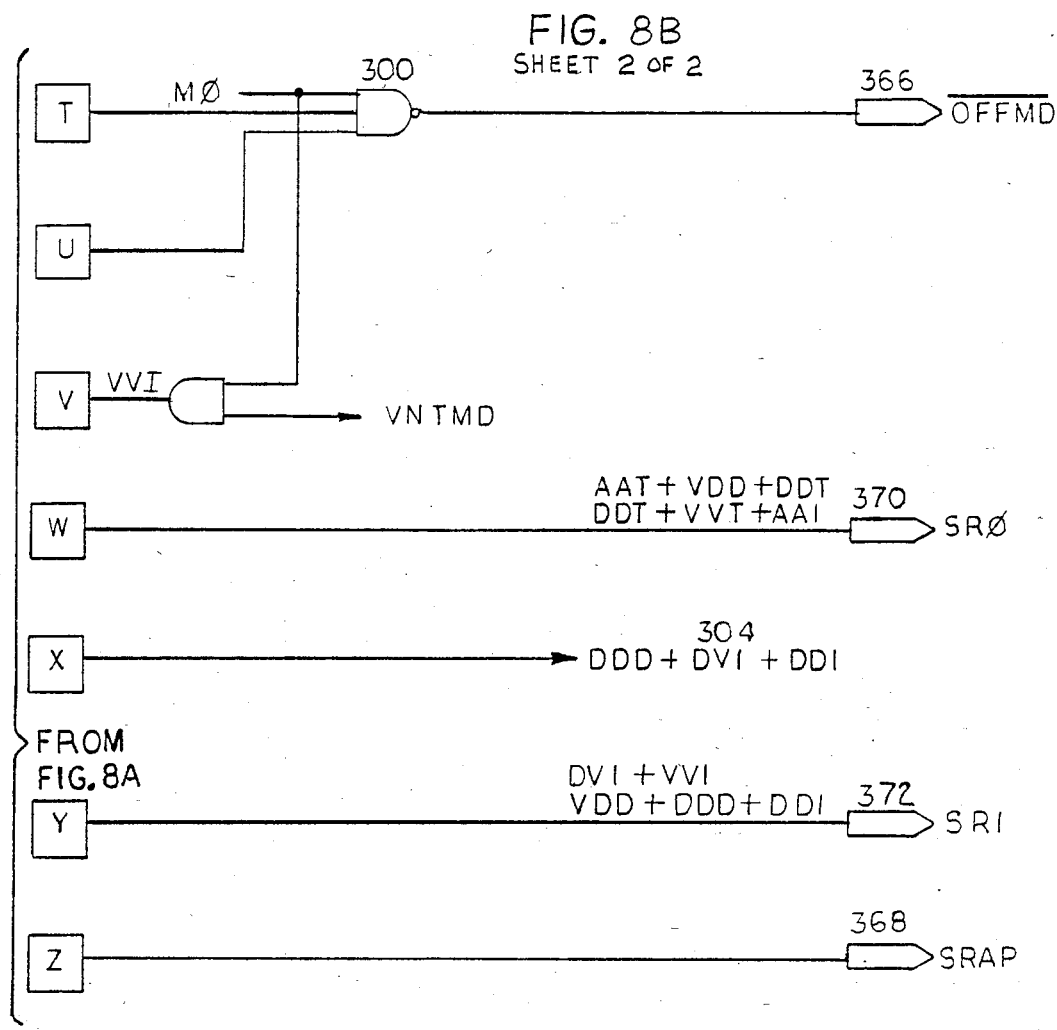

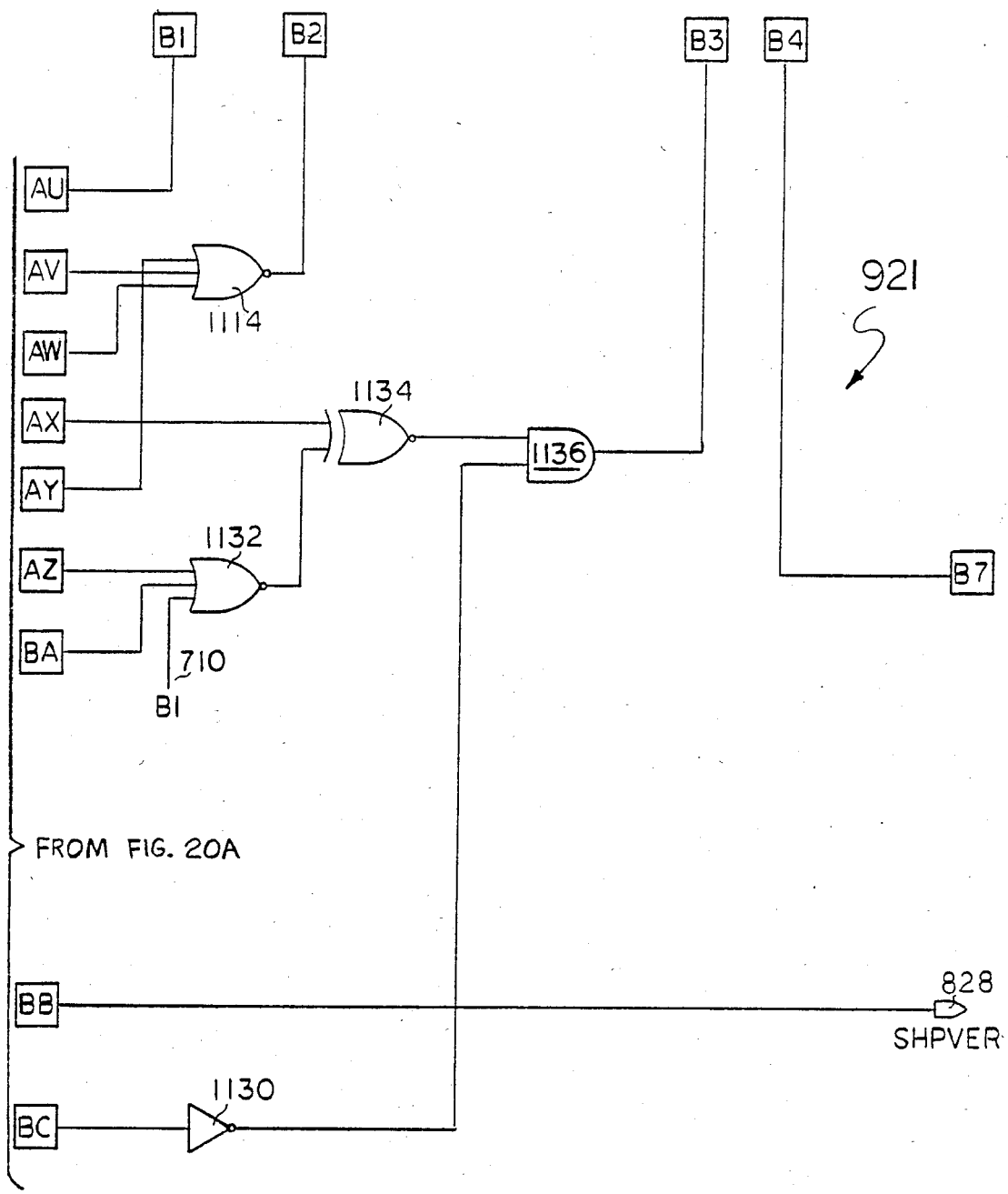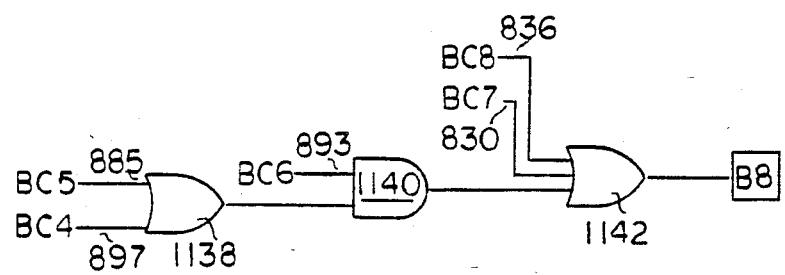
FIG. 20B
SHEET 3 OF 4

CARDIAC TISSUE STIMULATOR FOR STIMULATING IN THE DDX MODALITY

TECHNICAL FIELD

The present invention relates to the field of mode programmable tissue stimulating apparatuses and their method of operation. In particular, the present invention further relates to mode programmable cardiac stimulating apparatuses which provide single chamber and dual chamber pacing, such as pacing in VOO, VVI, VVT, AOO, AAI, AAT, DOO, DVI, VDD and DDD modes.

BACKGROUND ART

There has been an evolutionary development in tissue stimulating apparatuses. The advent of programmable tissue stimulators has allowed for the optimal pacing system for a specific individual, simplified troubleshooting of stimulator problems, and noninvasive changes in the stimulator programming.

At present, the newest and most sophisticated mode programmable cardiac pacing apparatuses (which are a subset of tissue stimulators) are designed to pace in the DDD mode. These apparatuses, while having the ability to stimulate (pace in the DDD mode) can also be programmed to pace in the AOO, VOO, VVI, AAI, AAT, VVT, VDD, DOO and DVI. The DDD mode of operation, at present, is the state of the art mode in pacing.

The DDD mode possesses the characteristics of truer physiologic pacing because of the advantages in its hemodynamic and electrophysiologic abilities.

The DDD mode of operation is designed to mimic the cardiac cycle electronically. Therefore, atrial or ventricular stimulation alone or atrial and ventricular stimulation in sequence will be delivered, so as to continuously maintain atrial and ventricular synchrony over a wide range of rates.

When a cardiac pacing apparatus is operated in the DDD mode, stimulation is provided to: (1) the atrium only in the presence of an atrial bradycardia with intact A-V conduction, (2) the ventricle alone in the presence of normal sinus rhythm in the absence of A-V conduction, and (3) both the atrial and ventricle in the presence of bradycardia in both chambers.

When the cardiac pacing apparatus is operated in the DDD mode, ventricular sensing is inhibited for a period of time after atrial stimulation to prevent cross-talk. This refractory or blanking period prevents the apparatus from sensing in the ventricle and falsely interpreting an atrial output pulse as a true ventricular depolarization. However, a drawback is that ventricular activity occurring during this blanking period may go undetected.

The DDD mode of operation for a cardiac pacing apparatus has been found to be ineffective in situations in which there is an electrically unstable atrium as evidenced by intermittent atrial flutter/fibrillation or frequent extra-systoles, or slow retrograde atrial activation which triggers ventricular pacing. DDD mode pacing is ineffective in these situations because the atrium cannot be stimulated, or atrial depolarization cannot be consistently sensed, or the timing of the atrial signal is inappropriate for governing physiological ventricular activation.

To combat many of the problems associated with pacing in the DDD mode only, the DDD mode pacing apparatus can reprogram from among the currently known pacing modalities, i.e., AAI, VVI, VDD, or DVI, in order to approximate normal physiological cardiac functions in the presence of bradycardia rhythm disturbances.

In recent years, some of these same pacing apparatuses have been equipped to cope with tachycardias. The techniques incorporated in these apparatuses to terminate tachycardias were either competitive underdrive pacing (asynchronous competitive pacing below the rate of the tachycardia); or burst or overdrive pacing (a short burst of rapid stimulation at a rate faster than the tachycardia); or delivery of programmed stimuli (emission of a single or double (or more) stimuli at a precise time to break the tachycardia). Such tachycardia terminating pacing apparatuses had external activation in early systems which dictated the method which is activated to terminate the tachycardia. Later there was the devleopment of automatic systems which would automatically provide the programmed method for breaking a tachycardia.

The present day DDD mode cardiac pacing apparatus, although approaching the point of being a true physiological pacing apparatus because of the conjunctive use of the other programmed pacing modes incorporated therein, still has many problems. These problems are associated with arrhythmias caused by pacing in a programmed DVI mode where there is no sensing in the atrium, or noneffective atrial stimulation which shortens battery life. There are also problems when pacing in the DDD mode when an R-wave that is premature (Premature Ventricular Contraction, PVC or junctional beat) is sensed and is followed by a slow retrograde atrial activity. This can result in a tachycardia consisting of a slow V-A retrograde pathway in the heart followed by sensing of that retrograde P-wave by the pacemaker and subsequent pacing of the ventricle, which is known as "pacer mediated tachycardia".

Besides particular mode problems associated with the present day DDD mode pacers, there are also problems in evaluating the performance of implanted DDD pacers due to their complexity when viewed on a surface ECG apparatus.

Besides those problems associated particularly with DDD mode pacing apparatus, there are other general problems with programmable pacing apparatus. Consistently there are problems in determining if a signal sensed on the P-channel of the pacing apparatus is actually a P-wave or merely noise. The existence of a valid P-wave will cause the pacer to be inhibited, where noise will not. Since there is no proper method to validate whether what is detected on the P-channel is noise or a valid P-wave the pacer can improperly acknowledge noise as a P-wave or not acknowledge a P-wave because it thought it was noise.

The present invention solves these and other problems associated with programmable pacing apparatus capable of pacing in the DDD mode.

SUMMARY OF INVENTION

The present invention is directed to a tissue stimulator, specifically a cardiac pacing apparatus, which implements, in addition to the operating modes of DDD, DOO, VOO, VVI, VVT, AOO, AAI, AAT, DOO, DVI, and VDD, the additional modes of DDI and DDX.

The main purpose for the DDI mode is to prevent arrhythmias associated with atrially asynchronous DVI pacing. It also does not have the problems associated with DDD pacing with regard to retrograde conduction.

The new operating mode of DDI is somewhat similar to the DVI pacing mode except that instead of sensing only in the ventricle, it senses activity in the atrium as well. However, when the pacer detects an atrial depolarization, it does not synchronize timing from that depolarization in order to pace the ventricle, even though such detection does cause the next atrial stimuli from the pacer to be suppressed or inhibited. The ventricular side of the pacemaker resets the timing as well as inhibits either of the two stimuli if an R-wave is sensed. Therefore, if an R-wave is sensed in a period before the atrial stimulus, the timing is reset and both stimuli are inhibited. If an R-wave is sensed between the atrial stimulus and the ventricle stimulus, the timing is reset and the atrial stimulus is inhibited.

The DDX mode is somewhat similar to the DDD mode except that when an R-wave is sensed, prior to atrial activity or an atrial stimulus or a time window, it is assumed that what is sensed is some type of premature activity. When this premature activity is sensed, all timers are reset as in the DDD mode but the pacer will pace in a forced DVI mode or extend the atrial refractory period for the next cardiac cycle. In this situation, the atrial sensing is inhibited. The purpose for inhibiting atrail sensing is based on the concept of preventing atrial sensing for the extension period after a premature activity (usually a premature ventricular contraction, PVC), thereby preventing the sensing of the likely retrograde P-wave. Therefore, any atrial sensing is inhibited for the next beat or extended part thereof.

The antitachycardia modes, (anti-tach) are incorporated in the apparatus of the invention. The anti-tach mode of operation are initiated by a programming sequence. In the anti-tach modes, the leading edge of an electro-magnetic burst will trigger pacing of the programmed chamber.

The apparatus of the invention has the ability, when given the appropriate command, to telemeter from the apparatus for reception and interpretation by an external device, the events as they take place in the cardiac tissue. The marker channels which are telemetered indicate whether the apparatus sensed a P or R-wave, and whether the apparatus put out an atrial or ventricular pulse for stimulation of the cardiac tissue.

There are two types of anti-tach modalities disclosed herein. The first is A-tach and the second is V-tach. When in one of these respective modalities, the respective mode of operation is AAI or VVI, respectively. The anti-tachycardia modalities are used in conjunction with the previously described marker channels, which channels mark whether the activity was paced or sensed or in the atrium or ventricle. The marker channels allow a separate external apparatus to synchronize the tach-trig signal with what is actually going on in the heart.

The command for entering the anti-tach mode of operation is given as a command signal to the communication section of the programmable pacing apparatus. In operation, when the anti-tach mode is selected there is either a forced AAI or a forced VVI operation. Therefore, the stimulation from the pacer is inhibited if there is sensed activity. However, if there is no sensed activity, the pacer will stimulate the respective chamber at the basic rate. In conjunction with a separate external apparatus, a stimulation pulse is introduced everytime a tach-trig signal from the communication section is detected. This will take place everytime the RF is turned on. Essentially, the antitachycardia modes provide an output pulse, at a fixed time after the leading edge of the RF burst. This output pulse signals the pacer to go ahead and trigger a pulse on the atrial or ventricular lead depending on whether it was in the atrial or ventricular mode.

The present invention also incorporates circuitry that is used to verify whether what is sensed on the P-wave detection channel is a sensed P-wave or noise. When an actual P-wave is sensed, the apparatus is inhibited to prevent the output of atrial stimuli. The P-wave verification circuitry takes the incoming signal and determines whether it is an actual P-wave or noise based on the time period that the signal lasts. This circuitry is integrally connected to the timing within the pacing apparatus. Additionally, if the timing out of the main counter is near the end of the cycle and there is not enough time to complete the noise test, a decision is made by the apparatus that the signal was not noise and that there was a valid P-wave. The apparatus sensing this condition will inhibit an atrial stimulus.

The above described modes of operation, DDX, DDI, anti-tach modes, markers, and the P verification circuitry are all integrally connected to three timers. These timers are designated as the A, B, and C timers. These timers are incorporated using complimentary metal oxide semi-conductor (cmos) logic circuitry within the pacing apparatus.

The A timer has three States, State A0, State A1 and State A2. State A0, is a holding State when not in state A1 or A2. State A1 lasts 50 or 100 milliseconds, and is used to test whether a signal from the atrial input amplifier is a sensed P-wave or noise. If the signal sensed on the atrial channel lasts less than the entire 50 or 100 ms. period a verified P-wave will result. If not, a failed P-wave test results and the signal is considered noise. State A2 defines an approximately 100 millisecond period within which, if successive R-waves are sensed, the A timer is reactivated. In the presence of continuous ventricular channel noise exhibiting greater than approximately 600 ppm (pulses per minute), the A timer will be continuously reset resulting in asynchronous pacing. In state A2 atrial sensing is also disabled.

The B timer has four States. The B timer is preloadable to 0, 50 ms., 100 ms., or the AV delay. The States are designated as B0, B1, B2 and B3. State B0 represents the absolute refractory of the ventricle and is presettable to 13, 26, 39, or 51 ms. It is essentially a blocking period for ventricular sensing. State B1 represents the portion of the A-V delay in which there is sensing for ventricle activity. Atrial sensing is disabled in both State B0 and B1. State B1 is presettable to 63, 89, 114, 140, 165, 190, 210, or 241 ms. State B2 represents the atrial escape interval following a paced ventricular event. State B3 represents an internal representative of the hysteresis function.

The C counter also has four States. The four States are designated as C0, C1, C2, and C3. State C0 is a holding State and essentially an alert state of the C timer. State C1 defines an absolute refractory period for both atrium and ventricle sensing. If is fixed at 150 ms. State C2 is the noise sample interval for ventricle refractory. This counter State is used in conjunction with the counter State A2, such that, if there is a sensed ventricular event, then the A timer is reset and placed in State A2. This State is presettable to 250 ms., 324 ms., 394 ms. or 470 ms. The C3 State defines the maximum tracking rate of the C timer. It can be programmed to rates of 90, 110, 130, or 150 pulses per minute (PPM). The maximum tracking feature guarantees that no TRV (pacer generated ventricular pulses) will follow another or a valid R-wave by less than the terminal count for this State. The atrial refractory may be programmed to consist of either State C1 only, State C1 and C2 or States, C1, C2 and C3.

It is the conjunctive use of these A, B, and C timers with the remainder of the CMOS circuitry which provide the pacing apparatus of the present invention to function in the DDI, DDX and the other previously addressed modalities. Additionally, it allows for P-wave verification, proper functioning of the antitachycardia modes, and provides proper marker signals for the marker channel telemetry.

An object of the invention is to provide a mode programmable advanced function pacing apparatus which can operate in the DDD AOO, VDD, DVI, DOO, VVT, AAI, VOO, VVI, AAT, DDI, and DDX modalities.

Another object of the invention is to provide a cardiac pacing apparatus which more closely approximates a true physiological pacing apparatus.

A still further object of the invention is to provide a cardiac pacing apparatus which has specific modalities for breaking tachycardias in either the atrium or ventricle.

Another object of the invention is to provide a pacing apparatus which allows for pacing in the DDX and DDI modalities.

Another object of the invention is to provide the means by which telemetric signals are used to mark sensed and paced events with a plurality of marker channels.

A still further object of the invention is to provide circuitry which will verify whether a signal sensed on the atrial channel is actually a P-wave or noise.

These and further objects of the invention will be subsequently described in detail in the following paragraphs.

BRIEF DESCRIPTION OF THE DRAWINGS

FIG. 2 shows the State diagram for the A-timer.

FIG. 3 shows the State diagram for the B-timer of the apparatus of invention.

FIG. 4 shows the State diagram for the C-timer.

FIG. 5A shows the State diagram for the blocked P and blocked P States of the A, B, and C timers.

FIG. 5B shows the state diagram for sensed P-waves in the DDI modality.

BEST MODE FOR CARRYING OUT THE INVENTION

The present invention is a tissue stimulator, more specifically a cardiac pacing apparatus which is capable of pacing in the pacing modes of VOO, VVI, VVT, AOO, AAI, AAT, DOO, DVI, VDD, DDD, and the further modes of DDI and DDX.

Pacing modalities VOO, VVI, VVT, AOO, AAI, AAT, DOO, DVI, VDD, DDD and new pacing modalities of DDI and DDX are represented by a three letter definition. The first letter represents the chamber or chambers of the heart which are paced by the stimulator apparatus. A "D" represents pacing in both the atrium and ventricle, an "A" represents pacing in the atrium alone and a "V" represents pacing in the ventricle alone.

The second letter represents the chambers of the heart that are being sensed. A "D" represents sensing in both the atrium and ventricle, an "A" represents sensing in the atrium alone and a "V" represents sensing in the ventricle alone.

The third letter represents the activity of the stimulator in the presence of a naturally occurring R or P-wave. An "I" represents the apparatus generated pulse is inhibited in the presence of a naturally occurring P or R-wave and a "T" represents triggering of an apparatus generated pulse in the presence of a naturally occurring P or R-wave. A "D" represents inhibiting and/or triggering in the presence of both a P and R-wave.

The letter "O" in the second and third positions of the modality symbol indicates that there is no sensing in the ventricle and atrium, and no inhibiting or triggering based on sensing, respectively.

The letter "X" in the DDX modality is a special letter representing a change in the apparatus' pacing characteristics which are temporary or permanent based on sensor inputs.

In order to understand how the present invention paces in the novel modes of DDI and DDX, the interaction of the logic circuitry between the pulse generator state logic and the A, B and C timers state logic will be disclosed. The description, therefore, will describe completely the interactive nature of the pulse generator state logic (PGSL), the logic of the A, B and C timers for carrying out these specific modes of operation, and other supporting logic circuitry.

Figure 1:
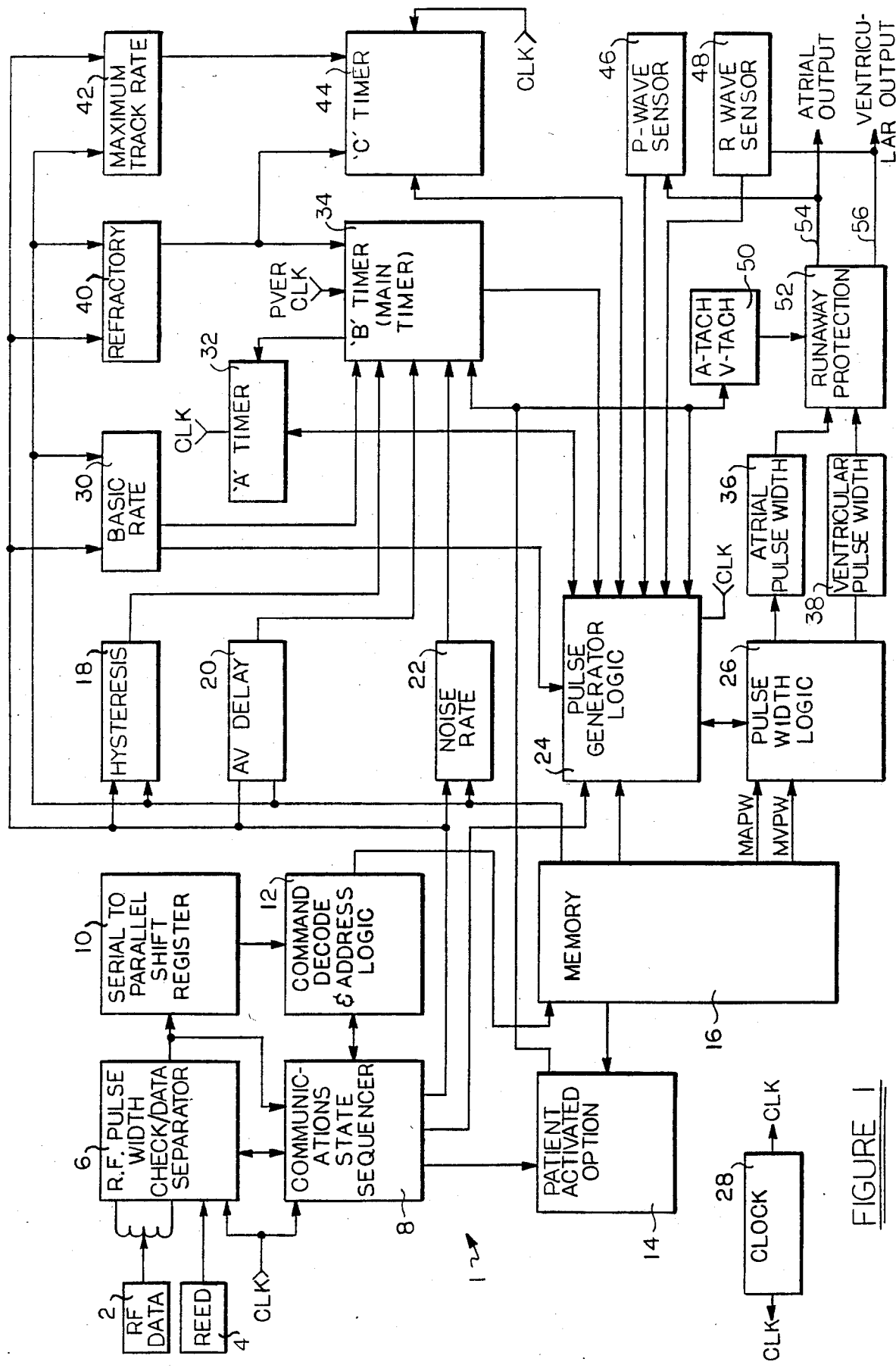
FIG. 1 is a block diagram of the tissue stimulator incorporating operation modes of DDI, DDX, P-wave verification, markers, and anti-arrhythmia modes of operation.

FIG. 1 shows a block diagram of the tissue stimulator of the invention.

The tissue stimulator of the invention is generally shown at 1 in FIG. 1. The programming data for the mode programmable tissue stimulator, specifically a cardiac pacing apparatus, is supplied via an RF carrier with data modulated on the signal. The data comes into the stimulator by RF Data Signal 2. The external unit provides an RF data link between the programming apparatus and the tissue stimulator such that programming of the specific modes of operation of the tissue stimulator 1 can be accomplished. In order to allow the RF Data 2 to be input into the memory the tissue stimulator 1, reed switch 4 must be closed unless it is deactivated by prior programming under circumstances for certain programming codes such as anti-tach activation. The reed switch 4 is closed by an external apparatus (not shown) and once closed will allow data to be input into memory via the command section comprising the RF pulse width check/data separator 6, Communications State Sequencer 8, serial to parallel shift register 10, and the command decode and address logic 12. The external apparatus for closing the reed switch is magnet.

The timing mechanism for the tissue stimulator invention is a 32768 hertz crystal oscillator 28. This provides the timing for controlling all the data flow within the tissue stimulator. The 32 kHz signal is divided to a pair of 158 Hz pulse trains. The first is designated CK1 and the second is designated CK2. Most of the logic of the apparatus of invention is clocked by the leading edge of the CK1. This includes driving the A, B, and C timers, synchronizing the R and P signals, clocking the T timer and all of the communications circuitry. The trailing edge of CK1 initiates atrial pulses or ventricular pulses and clocks the PGSL State flip-flops. The other 158 Hz pulse train, CK2, has pulses that are wider than CK1, overlaps CK1 on both edges, and is negative going. The entire width of CK2 is used to preload the B timer and reset A and C timers.

RF Pulse Width Check/Data Separator 6 receives an input from clock 28. RF Pulse Width Check/Data Separator 6 provides an output to serial to parallel shift register 10 and the Communications State Sequencer 8. The Communication State Sequencer 8 provides sequenced command signals for controlling the flow of data from the serial to parallel shift register 10 to the command decode and address logic 12. Therefore, upon entry into RF pulse width check/data separator 6, the information is input in serial form to parallel shift register 10 and output in parallel form to command decode and address logic 12. This logic is controlled by the Communication State Sequencer 8. The parallel data received by command decode and address logic 12 is output to memory 16 in accordance with the commands and addressing of the Communication State Logic Sequencer 8.

Memory 16, to which the parallel output of the command decode and address logic 12 is directed, has various memory sections which in FIG. 1 are shown separately. Hysteresis memory 18, AV delay memory 20, noise rate memory 22, basic rate memory 30, refractory memory 40 and maximum track rate memory 42 are all portions of memory 16. For simplicity, they have been set out separately but all are part of memory 16.

The data output from the command check decode and address logic 12 is output on the address bus which directs each bit of the data output from the Communications State Sequencer on the data bus to the correct cell of memory. The data bus is connected to the Communications State Sequencer 8 and the command data decode and address logic 12. The address bus is connected to the command check decode and address logic 12 and provides the addresses for the output data to the individual cells of memory for storage until required for a specific pacing modality as selected by the mode of operation of the apparatus. The third bus, the control bus, is connected to each of the memory cells and State sequencer 8. This provides the output control for the memory cells.

B-timer 34 is the main timer and accessed by hysteresis section 18 of memory, AV delay section 20 of memory, noise rate section 22 of memory, basic rate section 30 of memory, and refractory section 40 of memory. C-Timer 44 is accessed by the refractory section 40 of memory, and the maximum track rate 42 of memory. The A-timer is not accessed by memory, but is accessed by the B-timer 34, and the pulse generator logic 24.

PGSL 24 is accessed by the command sense sequencer 8, the mode sections of memory 16, pulse width logic section 26, the basic rate section 30 of memory 16, A-Timer 32, B-Timer 34, C-Timer 44, P-wave sensor 46, and R-wave sensor 48.

After the modes of operation have been selected, the PGSL, in conjuctive activity with the A, B and C timers, determines the actual pacing scheme of the apparatus, contingent on sensing a P-wave by the P-wave sensor 46 and an R-wave by the R-wave sensor 48. This sensing dictates when the stimulator provides outputs to the respective chambers through the pulse width logic 26, which in turn provides appropriate signals to either the atrial pulse width logic 36 or ventricular pulse width logic 38. This ultimately provides the appropriate atrial or ventricular output 54 or 56 to the tissue to be stimulated after passing through runaway protection logic 52 and output logic (not shown).

FIGS. 2 through 21B disclose the operable portions of the PGSL 24, and the A, B, and C timers 32, 34, and 44 respectively for operating the stimulator in the novel modes of DDI and DDX. The component parts for each of the logic circuits described therein include AND Gates, NAND Gates, OR Gates, NOR Gates, inverters, Exclusive OR Gates, Exclusive NOR Gates, flip-flops or latches, and multiplexers (MUX), the operation and use of which are well known to those skilled in the art.

DEFINITION OF SIGNAL TERMS

Disclosure and description of the apparatus and the method of use of the apparatus of the invention uses the following terms to describe the signals used throughout its description:

1. ADELTRVA—A delay trigger signal for the atrium or ventricle whichever is later for the programmed pacing modality.
2. $\overline{ADET}$—A signal which has a logic "0" value when there is a signal detected by atrial sensing by apparatus of the invention.
3. ATACH—The signal representative of a temporary atrial antitachycardia mode to allow an external device to pace the atrium on receipt of the appropriate RF burst.
4. ACCR—Analog counter reset signal.
5. ACC0—Analog counter bit 0 signal.
6. ACC1—Analog counter bit 1 signal.
7. ACC2—Analog counter bit 2 signal.
8. ACC3—Analog counter bit 3 signal.
9. AEDET—Any RF edge detect signal.
10. ANALG—Analog telemetry, command mode 6 signal.
11. APW—Atrial pulse width signal.
12. ARST—The signal representative of the resetting of the A timer.
13. ASYNCAT—The signal representative of the magnet activated asynchronous antitachycardia pacing modality.
14. ATREF—The signal representative of atrial refractory.
15. ATRMD—The signal representative of a selection of one of the atrial modalities.
16. AUTEST—Automatic test command, command mode signal.
17. AVLD—The signal representative of the atrium/ventricle (AV) preload for the B timer.
18. AV1P—The signal representative of the decoded AV delay signal.
19. AV2P—The signal representative of the decoded AV delay signal.
20. AV3P—The signal representative of the decoded AV delay signal.
21. A0—The holding State of the A-counter when not in A counter States A1 or A2.
22. A1—The 50 ms. or 100 ms. period of the A counter for allowance of testing a sensed P-wave.
23. A2—This is a 100 ms. resettable period to screen for continuous noise on the ventricular channel.
24. $\overline{B\text{-}DET}$—A signal which has a logic "0" value when there is a signal detected by ventricular sensing by the apparatus of invention.
25. BC0—The signal representative of B counter output Q0.
26. BC1—The signal representative of B counter output Q1.
27. BC2—The signal representative of B counter output Q2.
28. BC3—The signal representative of B counter output Q3.
29. BC4—The signal representative of B counter output Q4.
30. BC5—The signal representative of B counter output Q5.
31. BC6—The signal representative of B counter output Q6.
32. BC7—The signal representative of B counter output Q7.
33. BC8—The signal representative of B counter output Q8.
34. BP—The signal representative of the blocked P-wave.
35. BPLCK—The signal representative of B counter preload.
36. BX0—The signal representative of external bus 0.
37. BX1—The signal representative of external bus 1.
38. BX2—The signal representative of external bus 2.
39. BX3—The signal representative of external bus 3.
40. BX4—The signal representative of external bus 4.
41. B0—The B counter State which represents absolute refractory in the atrium and ventricle.
42. B1—The B counter State in which there is sensing for ventricle activity but there is absolute refractory in the atrium (AV delay).
43. B2—The B Counter State which represents the B counter State which is the atrial escape interval.
44. B3—The B counter State representative of hysteresis.
45. CK1—This is a divided down clock signal from the 32768 hertz crystal controlled clock. This is a 158 hz pulse train which is used to clock most of the State logic with a leading edge. The CK1 clock drives the A counter, B and C timers, synchronizes the R and P signals, clocks the T-timer and all of the communication circuitry. The trailing edge of CK1 initiates the TRA and TRV pulses and clocks a pulse generator State logic (PGSL) flip-flops.
46. CK2—The second 158 hz clock which is wider than CK1, overlaps it at both edges and is negative going. The B timer is preloaded and the A and C timers are reset when CK2 has a logic "0" value.
47. CMDW—A command wait command, communications mode 3 signal.
48. COMASYNC—The signal representative of the command to direct the apparatus to stimulate asynchronously.
49. COMCYC—The command cycle signal.
50. CPAOCMD—Strobe signal for the patient option activate command.
51. CRST—The signal representative of resetting the C-timer.
52. C0—The holding State of the C-timer after timing out of State C3 until the end of the cycle of the main or B timer. This is an alert State for the C counter.
53. C1—The C timer State in which there is absolute refractory in both the atrium and ventricle chambers.
54. C2—The C timer which is the noise sample interval for ventricular activity. If there is a ventricular activity in this State, the A timer is placed in State A2 and reset.
55. C3—The C timer State that is the maximum track rate for the C timer.

56. DBACC—A signal for placing the analog section counter on the bus.
57. DBMRK—The signal for placing markers on the bus.
58. DPW—The signal representative of a sensed P-wave in the DDI modality.
59. DUAL—The signal representative of the operation of the apparatus of invention in the dual chamber modes. (Same as M3)
60. FASTEN—The signal representative of the fast enable count for the pacer. This is for signaling the state of the battery. Prior to the recommended replacement time the magnet rate will increase by 14% and the AV delay will be fixed at 101 ms. This signal is used in conjunction with the Patient Activated Option to increase pacing rate and other parameters.
61. FRDVI—The signal representative of the forced DVI pacing modality of the apparatus.
62. HYST—The signal representative hysteresis enablement of the apparatus. This will enable the hysteresis function of the apparatus.
63. INDEX—The signal for indexing in analog telemetry and/or enabling signal for antitachycardia modes.
64. IPW—The signal representative of an inhibiting P-wave. This inhibiting P-wave will inhibit a pacer generated atrial pulse.
65. IRW—The signal representative of an inhibiting R-wave. This inhibiting R-wave will inhibit a pacer generated ventricular pulse.
66. IW—The signal representative of an inhibiting wave, either P or R which will inhibit a pacer generated signal for either the atrium or ventricle.
67. LTCB1—The signal representative of the latched TCB1 state.
68. M-DUAL—The signal representative of a dual chamber modality in memory.
69. M-MODE 0—The signal representative of the mode 0 bit in memory.
70. M-MODE 1—The signal representative of the mode 1 bit in memory.
71. M-MODE 2—The signal representative of the mode 2 bit in memory.
72. M-MODE 3—The signal representative of the mode 3 bit in memory.
73. MAR-0—The signal representative of atrial refractory period bit 0 in memory.
74. MAR-1—The signal representative of atrial refractory period bit 1 in memory.
75. MAGAV—The signal representative of force of the magnet used in conjunction with the fast enable to force a 101 ms. AV delay when a magnet is applied.
76. MAV 1, 2, 3—The signals representative of the AV delay storage bits in memory.
77. MCBP 0, 1, 2, 3—The signals representative of the course basic period bits in memory.
78. MCHY, 0, 1, 2, 3—The signals representative of the course hysteresis period bits in memory.
79. MEASCYC—The signal for the analog telemetry measurement cycle.
80. MFBP 1, 2, 3—The signals representative of the fine basic period bits in memory.
81. MFHY 0, 1, 2, 3—The signals representative of the fine hysteresis period for bits for memory.
82. MLC 0, 1—The signals representative of the lead configuration bits in memory.
83. MOPL 0—The signal representative of the patient option lockout bit 0.
84. MOPL 1—The signal representative of the patient option lockout bit 1.
85. MOPL 2—The signal representative of the patient option lockout bit 2.
86. MOPL 3—The signal representative of the patient option lockout bit 3.
87. MPAO 0—The signal representative of the patient activate option bit 0.
88. MPAO 1—The signal representative of the patient activate option bit 1.
89. MRK F—The signal representative of markers F.
90. MRK 8—The signals representative of markers 8.
91. MRR0, 1—The signals representative of the ventricular relative refractory period bits in memory.
92. MMTR 0, 1—The signals representative of the maximum tracking rate bits in memory.
93. MNR0, 1—The signals representative of the noise rate bit in memory.
94. M0—The signal representative mode 0 output from the $Q_0$ output latch 238.
95. $\overline{M0}$—The signal representative of the mode 0 output from the $\overline{Q}_0$ output of latch 238.
96. M1—The signal representative mode 1 output from the $Q_1$ output of latch 238.
97. $\overline{M1}$—The signal representative of the mode 1 output from the $\overline{Q}_0$ output of latch 238.
98. M2—The signal representative of the mode 2 output from the $Q_2$ output of latch 238.
99. $\overline{M2}$—The signal representative of the M2 output from the $\overline{Q}_2$ output of latch 238.
100. M3—The signal representative of mode 3 output from the $Q_3$ output of latch 238. (Duplicate signal name for DUAL)
101. $\overline{M3}$—The signal representative of the mode 3 output from the $\overline{Q}_3$ output of latch 238.
102. NCA—Least significant bit (LSB) of the communications mode.
103. NCB—The next LSB of the communications mode.
104. NCC—The most significant bit (MSB) of the communications mode.
105. NO EXPND—Signal to indicate no expansion chip.
106. OFFMD—The signal representative of the off mode.
107. PFASREQ—The signal representative of the patient activated fast rate request.
108. PPCYC—The signal representative of the pulse parameter cycle.
109. POSHD—Position head command, command mode 1 signal.
110. PSLOREQ—The signal representative of the patient activated rate slow down request.
111. PVER—The signal representative of a verified P-wave.
112. PWT—The signal representative of a P-wave trigger.
113. RAP OSC—The signal representative of the runaway protection oscillator.
114. RAP 170—The signal representative of the runaway protection limit 170 beats per minute is exceeded.
115. RDCNT—The signal representative of reading the address memory.
116. RDST—The signal representative of the read switch strobe.
117. RFD—The signal representative of the RF data synchronized with the CK1 clock.

118. RFDATA—Signal indicative of RF data being input to the stimulator.
119. RFOFF—RF is off communications, command mode 0 signal.
120. RWT—The signal representative of an R-wave trigger.
121. RXOVER—The signal to indicate atrial/ventricle crossover mode when in one of the atrial modes.
122. SA0—The A-timer State flip-flop signal.
123. SA1—The A-timer State flip-flop signal.
124. SBP—A signal representative of blocked P-wave.
125. SB0—The B counter State flip-flop signal.
126. SB1—The B counter State flip-flop signal.
127. SC0—The C counter State flip-flop signal.
128. SC1—The C counter State flip-flop signal.
129. SHPVER—The signal representative of the shortened P-wave verification time of 50 ms.
130. SLOEN—The signal representative of slow enable to indicate the replacement point for a battery. The magnetic rate will drop by 11% and the magnet AV delay will be set to 127 ms. The signal is used in conjunction with the Patient Activated Option to decrease pacing rate and other parameters.
131. SPW—The signal representative of a sensed P-wave.
132. SRW—The signal representative of a sensed R-wave.
133. T Counter (timer)—The communication State counter.
134. TACTRIG—The signal representative of RF antitachycardia pulse trigger.
135. TACH—The antitachycardia mode signal.
136. TACH FORCE—The signal representative of the antitachycardia mode change.
137. TB—The signal representative of the T counter State B.
138. TCA—The signal representative of a terminal count of the A timer.
139. TCA1—The signal representative of a terminal count of the A0 State of The A timer.
140. TCA2—The signal representative of a terminal count of the A 2 State of the A timer.
141. TCBS—The signal representative of a terminal count of the B timer.
142. TCB0—The signal representative of a terminal count of the B0 State of the B timer.
143. TCB1—The signal representative of a terminal count of the B 1 State of the B timer.
144. TCB2—The signal representative of a terminal count of the B 2 State of the B timer.
145. TCB3—The signal representative of a terminal count of the B 3 State of the B timer.
146. TCC—The signal representative of a terminal count on the C timer.
147. TCC1—The signal representative of a terminal count of the C 1 State of the C timer.
148. TCC2—The signal representative of a terminal count of the C 2 State of the C timer.
149. TCC3—The signal representative of a terminal count of the C 3 State of the C timer.
150. TCN—The signal representative of a terminal count for the B timer when noise is present.
151. TD—The signal representative of the T counter State D.
152. TF—The signal representative of the T counter State F.
153. TMIRT—The signal representative of a telemetry transmission of an inhibiting R-wave.
154. TQ2—The signal representative of the T counter Q2 bit.
155. TQ3—The signal representative of the T counter Q3 bit.
156. TQ4—The signal representative of the T counter Q4 bit.
157. TR—The signal representative of a temporary selection of a 30 PPM diagnostic pacing rate as per programming by a physician.
158. TRAD—The signal representative of the clock cycle immediately preceding an atrial pacer pulse request. 159. TRAREQ—The signal representative of atrial pacer pulse request.
160. TRA or TRV—The signal representative of the trigger for the atrium or ventricle whichever comes first in the designated mode.
161. TRIG—The signal representative of a trigger for antitachycardia pulse.
162. TRVD—The signal representative of the clock cycle immediately preceding a ventricular pacer pulse request.
163. TRVREQ—The signal representative of ventricle pacer pulse request.
164. TST 0—Normal pacer operation including runaway protection and clock prescaler. In any other test mode the clock prescaler pulse width logic and runaway protection are bypassed.
165. TST 1—Loading address using CK1 as a strobe.
166. TST 2—Data bits X1 to X4 are read to or written from memory. Static operation period. H=write and where L=read. BX4 is a logic "1" value to write and logic "0" value to read.
167. TST 3—Not used.
168. TST 4—Normal pacer operation except that the clock prescaler and runaway protection are bypassed.
169. TST 5—RF data input strobed with CK1 and communication states.
170. TST 6—The signal representative of PGSL States.
171. TST 7—The signal representative of PGSL States.
172. T0—The signal representative of the T counter State 0.
173. T1—The signal representative of the T counter State 1.
174. T2—The signal representative of the T counter State 2.
175. T3—The signal representative of the T counter State 3.
176. T4TF—The signal representative of the T counter States T4 through TF.
177. VTACH—The signal representative of a ventricular anti-tachycardia mode which is initiated by RF pulse.
178. VNTMD—The signal representative of the ventricular modes of operation.
179. ZOO—The signal representative of all of the modes comprising AOO, VOO and DOO.

The description of the circuit will describe the logic functions, however, it is understood that the events described simultaneously take place on the occurrence of a single clock signal from $\overline{CK1}$ or CK2 in the PGSL, A, B, C timers and flip-flops unless otherwise stated.

Before describing the specific state logic of the PGSL, A timer, B timer and C timer, a description of the State diagrams and timing diagrams of the A, B and C timer will be set forth. The description of the State and timing diagrams for these timers shown in FIGS. 2 through 7 are helpful to understanding the logic circuits of the invention.

Referring to FIG. 2, the state diagrams for the A timer are generally shown at 62. There are three states for the A timer, Stste A0, 64; State A1, 66; and State A2, 68. State A0, 64 is the A timer holding state that is not time limited; accordingly its terminal count TCA0 is ignored. To terminate State A0 and to proceed to State A1 or A2, there must be a sensed P-wave or R-wave, respectively.

In order to enter State A1, there must be a sensed P-wave and the B timer must not be in State B0, 71, or B1, 72, (FIG. 3). Additionally, the C timer must not be in atrial refractory and the FRDVI state must not be set. The atrial refractory states are determined by C1 if atrial refractory bits MAR0 and MAR1 are logic "0" values, by (C1+C2) if MAR0 is a logic "1" value and MAR1 is a logic "0", and by (C1+C2+C3) if MAR1 is a logic "1" value where C1, C2, and C3 represent the states C1, C2, and C3 of the C timer 44.

When the foregoing takes place the A timer will change from State A0 to State A1. State A1, 66, once initiated has a terminal count of 50 or 100 ms. depending on the AV delay. State A1 has no preload value.

There are three methods to terminate State A1, the first two result in initiating State A0, 64 and the third results in initiating State A2. The two events that will result in initiating State A0, 64, are the timing out of the A timer with a TCA1 50 or 100 ms. terminal count or a sensed R-wave and the C timer not being in State C2, 77, (FIG. 4). The third event which will terminate State A1, 66, and will result in the initiation of State A2, 68, is a sensed R-wave and the C timer being in State C2, 77, (FIG. 4). Additionally, when the A timer is in State A0, 64 and an R-wave is sensed and the C-timer is in State C2, 77, State A2, 68, will be initiated.

State A2, 68, is the R-wave noise avoidance State. The terminal count on State A2, 68 is 100 ms. and there is no preload value for this State. As was described, State A2, 68, can be initiated from States A0, 64 and A1, 66. State A2, 68 will continually be reset if an R-wave is sensed during the counting out of State A2, 68. State A2, 68, is terminated only by a TCA2. At TCA2, the A timer initiates State A0, 64.

The state diagram for the B timer is generally shown in FIG. 3 at 70. The B timer has four states. In the diagram shown in FIG. 3 States B2 and B3 are combined at 73, where B2 is representative of the basic rate and B3 is representative of the hysteresis rate. In either case only State B2 or B3 can be running at one time and never can they run simultaneously.

State B0, 71, is the first B timer State. Its terminal count can be set at 13, 26, 39 or 52 ms. This State has no preload value. This is the blanking State for both P and R-wave sensing. To terminate State B0, 71, there must be a terminal count of TCB0. This terminal count initiates State B1, 72, because the B timer is a continuous timer.

State B1, 72 is the AV delay State which is programmable to 63, 89, 114, 140, 165, 190, 210 or 241 ms. During this period, P-wave sensing is refractory but R-wave sensing is alert. There are two ways to terminate State B1, 72. The first way to terminate this State is to reach its terminal count, TCB1, or to have a latched TCB1 (LTCB1), and to have the C timer in State C0, 75 (FIG. 4). After this takes place a State B2, 73 will be initiated after a resulting TRV (trigger ventricular pulse).

The second method of terminating State B1, 72 is to have a sensed R-wave and the A timer not being in State A2, 68 (FIG. 2). This will initiate State B2 or B3, 73, depending on the programming, and preload the AV delay value in the B timer.

As previously described State B2 or B3 are shown at 73, as the basic and hysteresis rates respectively. The B2 or B3 states can be terminated by terminal count TCA1 when the PVER state (FIG. 5E) is set. This will cause initiation of State B1, 72 and the 50 or 100 ms. value TCA1 will be preloaded into the B counter in State B1.

State B2 or B3 can be terminated when there is a $\overline{DPW}$ ($\overline{SPW}$ state for the DDI modality) State set and a TCN and the A timer is in State A2 or the SBP state is set; or TCB2 or TCB3 is reached and A timer is not in A1. When this is found, a TRA (trigger A pulse) will be produced and State B0 will be initiated and the pacer cycle will start again.

The third method of terminating State B2 or B3 which does not result in a TRA is when the DPW State is set and there is a TCB2 or TCB3 and the A timer is not is State A1. This will result in the initiation of State B1.

The fourth method of terminating State B2 or B3 does not actually terminate the State but restarts it. If while in State B2 or B3 there is a sensed R-wave and the A timer is not in State A2, 68 and the C timer is not in State C1, 76, or C2, 72, the B timer State B2 or B3 will be preloaded with the AV delay and restarted.

The C timer State diagram is generally shown at 74 in FIG. 4. There are four states in the C timer. State C0, 75, is the State of unlimited duration and its terminal count, TCC0 has no affect on pacer operations. State C1 will be initiated if there is a TRV or there is an R-wave and the A timer is not in State A2, 68 (FIG. 2) and the B timer is not in State B1, B2, or B3.

State C1, 76, is the absolute refractory state and has no preload value. Ther period of State C1, 76 is fixed at 150 ms. State C1, 78 is totally refractory to both the P and R-waves being sent. The only method to terminate State C1 is the occurrence of a TCC1, which initiates State C2, 77.

State C2 is a relative refractory state of the C timers programmable to 250, 325, 394, or 470 ms. The only method to terminate State C2 is the occurrence of a TCC2, which initiates State C3,78.

State C3, 78 is the maximum tracking rate of the C timer. Its terminal count is programmable to 90, 110, 130 or 150 PPM. This guarantees that no TRV will follow another or follow a valid R-wave by less than the programmed inverval of C3. There are two methods to terminate State C3, 78. The first is a sensed R-wave and the A timer not being in State A2, 68 and the B timer being in State B1, 72 or B2, 73 or B3, 73. This will terminate State C3, 78 and initiate State C1, 76. The second way to terminate State C3 is the occurrence of a TCC3, which will initiate holding State C0,75.

Referring to FIG. 5A, the block P State diagram is generally shown at 79. There will be a sensed block P (SBP) State, 81 whenever there is a TCA1 and an invalid PVER signal. A block P State, ($\overline{SBP}$) 80 is initiated when there is an IRW signal or a TRVD signal.

Referring to FIG. 5B, the State diagram for the DPW State is generally shown at 80'. To enter the DPW State, 82', there must be an IPW signal and the apparatus must be in the DDI modality. To leave the DPW State 82' and enter the $\overline{DPW}$ State 81' there must be an SBP signal or the C timer must be in State C1.

Figure 5C:
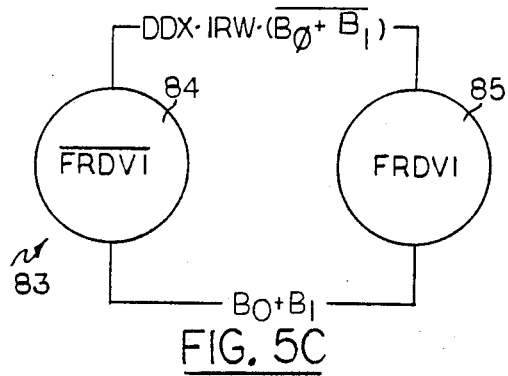
FIG. 5C shows the state diagrams for FRDVI (forced DVI) in the DDX modality.

Referring to FIG. 5C, the State diagram for the FRDVI States is generally shown at 83'. To enter the FRDVI State 85', the apparatus must be in DDX modality, there must be an IRW signal and the B timer must not be in States B0 or B1. To leave the FRDVI State 85' and enter the $\overline{\text{FRDVI}}$ State 84', the B timers must be State B0 or B1.

Figure 5D:
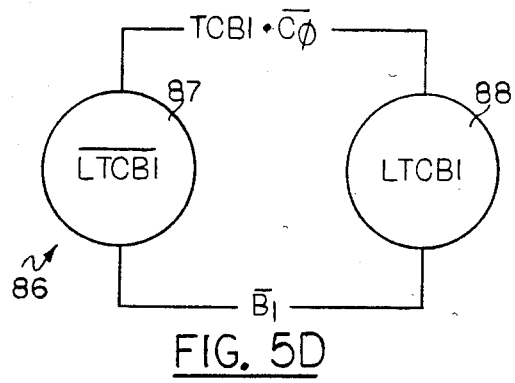
FIG. 5D shows the state diagrams for the LTCB1 (latched TCB1) state.

Referring to FIG. 5D, the State diagram for the Latch TCB1 state is generally shown at 86'. To enter the latched TCB1 State 88' there must be a TCB1 signal and the C timer must not be in State C0. To leave the latched TCB1 State 88' and enter the latched $\overline{\text{TCB1}}$ State 87', the B timer must not be in State B1.

Figure 5E:
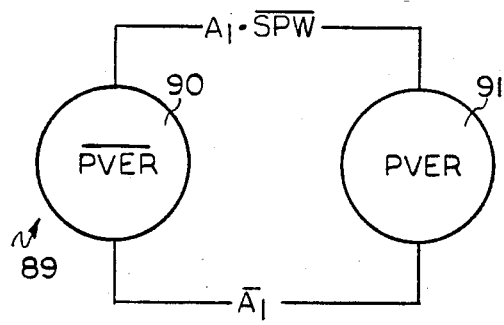
FIG. 5E shows the state diagram for P-wave verification (PVER).

Referring to FIG. 5E, the state diagram for the PVER state is generally shown at 89'. To enter the PVER state 91', the A timer must be in State A1 and a P-wave must not be sensed. To leave the PVER State 91' and enter the $\overline{\text{PVER}}$ State of 90' the A timer must not be in State A1.

Figure 5F:
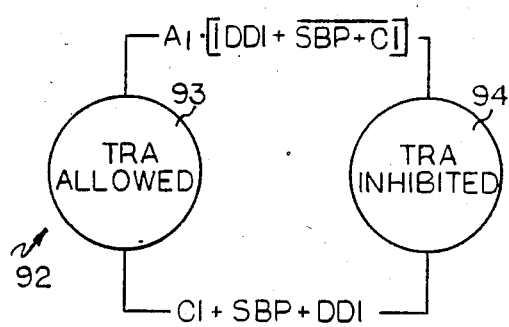
FIG. 5F shows the state diagram for the generation of a TRA signal in the DDI modality.

Referring to FIG. 5F, the state diagram for generation of a TRA signal in the DDI modality is shown generally at 92'. To allow a TRA signal 93', the C timer must be in State C1 or the P-wave verification test must have failed resulting in a SBP signal or the apparatus must not be in the DDI modality. In order to inhibit a TRA signal 94', the A timer must be in State A1 and: the apparatus must be in the DDI modality or not have failed the P-wave verification resulting in an $\overline{\text{SBP}}$ signal, or the C timer is in State C1.

Figure 6:
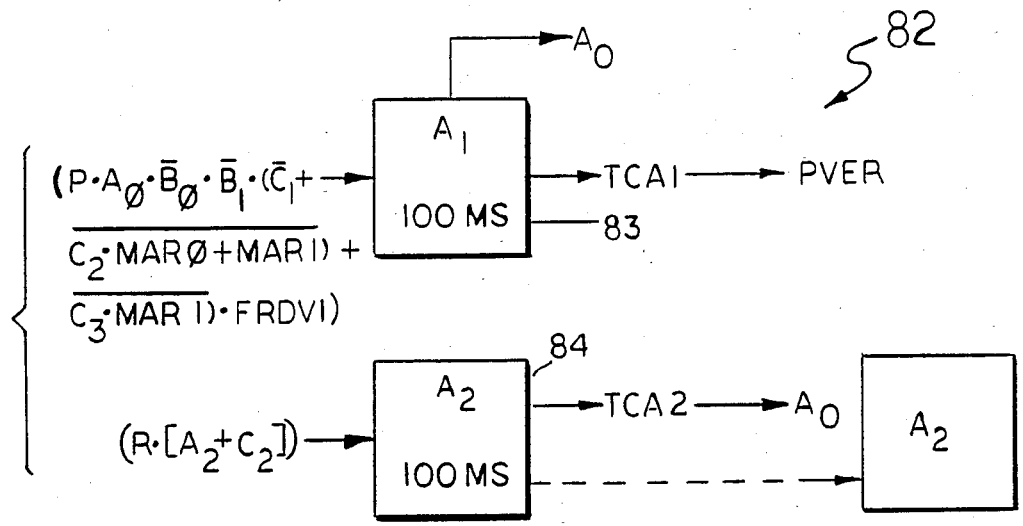
FIG. 6 shows the timing diagram for the A timer.

Referring to FIG. 6, the timing diagram for the A timer is shown generally at 82. The A timer is not a continuous timer which times from State A0 through State A2. The two States A1 and A2 are used for timing the detection of P-waves and R-waves, respectively. The A1, 83 State is 50 or 100 ms, dependent on the AV delay and A2, 84 is 100 ms.

State A0 is unlimited in time and a TCA0 will not cause any events. However, when there is a sensed P-wave and the A timer is in State A0; and not in B timer States B0 or B1; and not in the post ventricular atrial refractory period as defined by the C timer in accordance with MAR 0–1 State A1 is entered. After timing out with a TCA1 terminal count, providing there was a valid P-wave, a PVER signal is generated and the A timer returns to State A0. If there is no valid P-wave, the A timer will reach a TCA1, setting the blocked P-wave State SBP, and initiate State A0.

The A2 State, 84 has a duration of 100 ms. and is initiated from State A0 or A1. Once initiated, the A State will time for a 100 ms. period and, at the occurrence of a TCA2, it will return to State A0. However, if an R-wave is sensed during A2, this State will be reset for another 100 ms. period. It is only when no additional R-waves are sensed during State A2 that a TCA2 is reached, returning the A timer to State A0.

Figure 7:
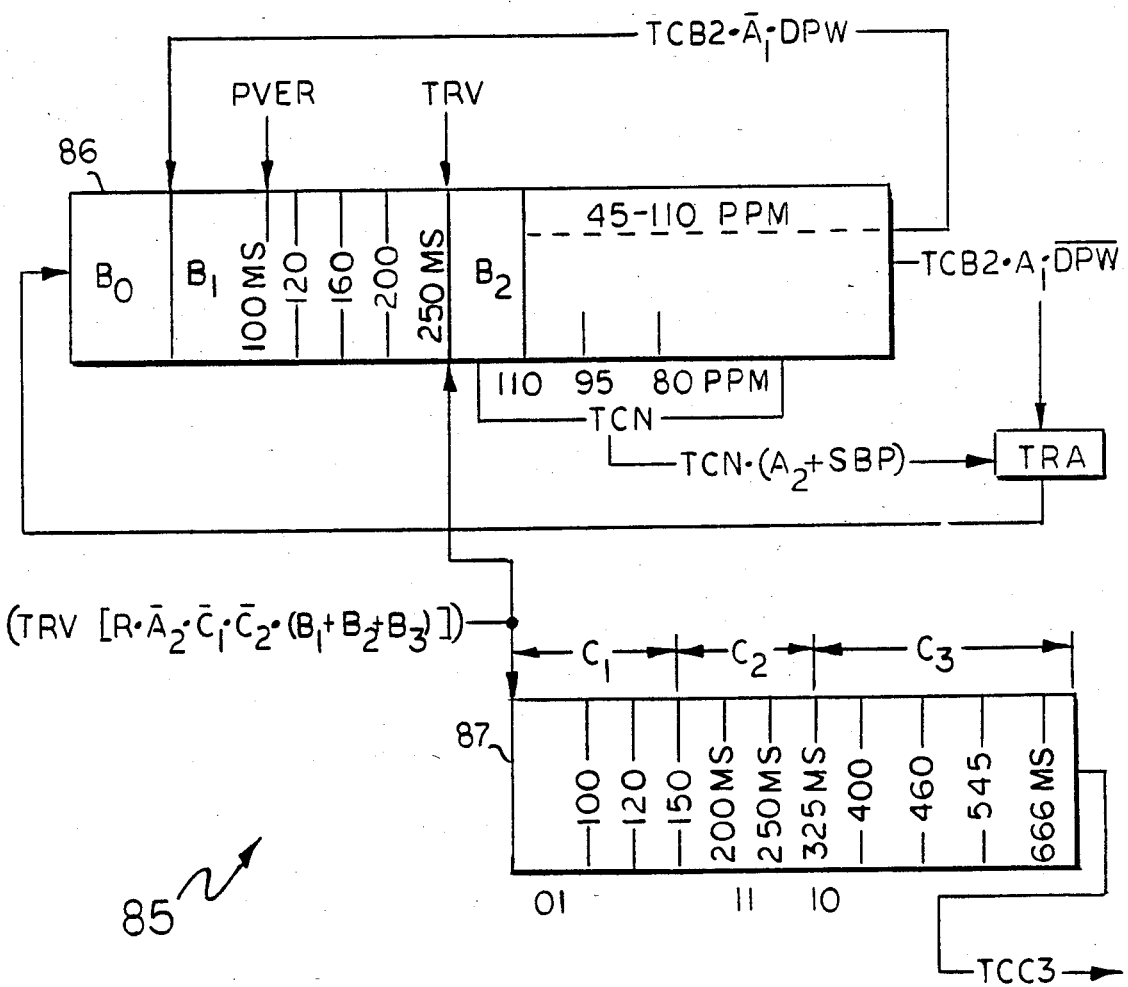
FIG. 7 shows the interactive timing diagrams of the B and C timers.

Referring to FIG. 7, the timing diagrams for the B and C timers are shown generally at 85. The B timer diagram is shown at 86 and the C timer diagram is shown at 87. Both the B and C timers are consecutive timers in which a terminal count on one state initiates the next state.

Referring to B timer timing diagram 86, State B0 is the blanking period. At TCB0, State B1 is initiated. A TCB1 will occur at a maximum of 250 ms. after initiation of State B1. State B1, may also be entered with a preload of 50 or 100 ms. following a valid P-wave in DDD and DDX modes. Also if an R-wave is not sensed during B1, a TRV will be generated at TCB1 if the C timer is in State C0. If the C Timer is not in State C0, then the latched TCB1 (LTCB1) will result in a TRV only after TCC3.

The B2 State will time out to a TCB2 if the A timer is not in the A1 state and there is no sensed P-wave, which TCB2 then results in a TRA. If during B2, a TCN results and noise was detected on the P channel resulting in a SBP or A2 is running, a TRA will also result. After the TRA, the B0 State is set.

If there is either a TRV or a sensed R-wave during State B1, B2 or B3 and the A timer is not in A2 and the C timer is not in C1 or C2, C timer State C1 is initiated. The C timer, like the B timer, is a continuous timer in which a terminal count on one State initiates the next State except for State C0. When the TCC3 is reached, the C timer reinitiates wait State C0.

The novel modalities of DDI and DDX will be described with reference to FIGS. 8A through 21. The novel modalities of DDI and DDX have their logic values derived from the M-Mode 0–3 logic values programmed into memory. Therefore, the description of the State logic for each of the novel modalities of stimulation will begin in the mode section of the PGSL.

Figure 8A:
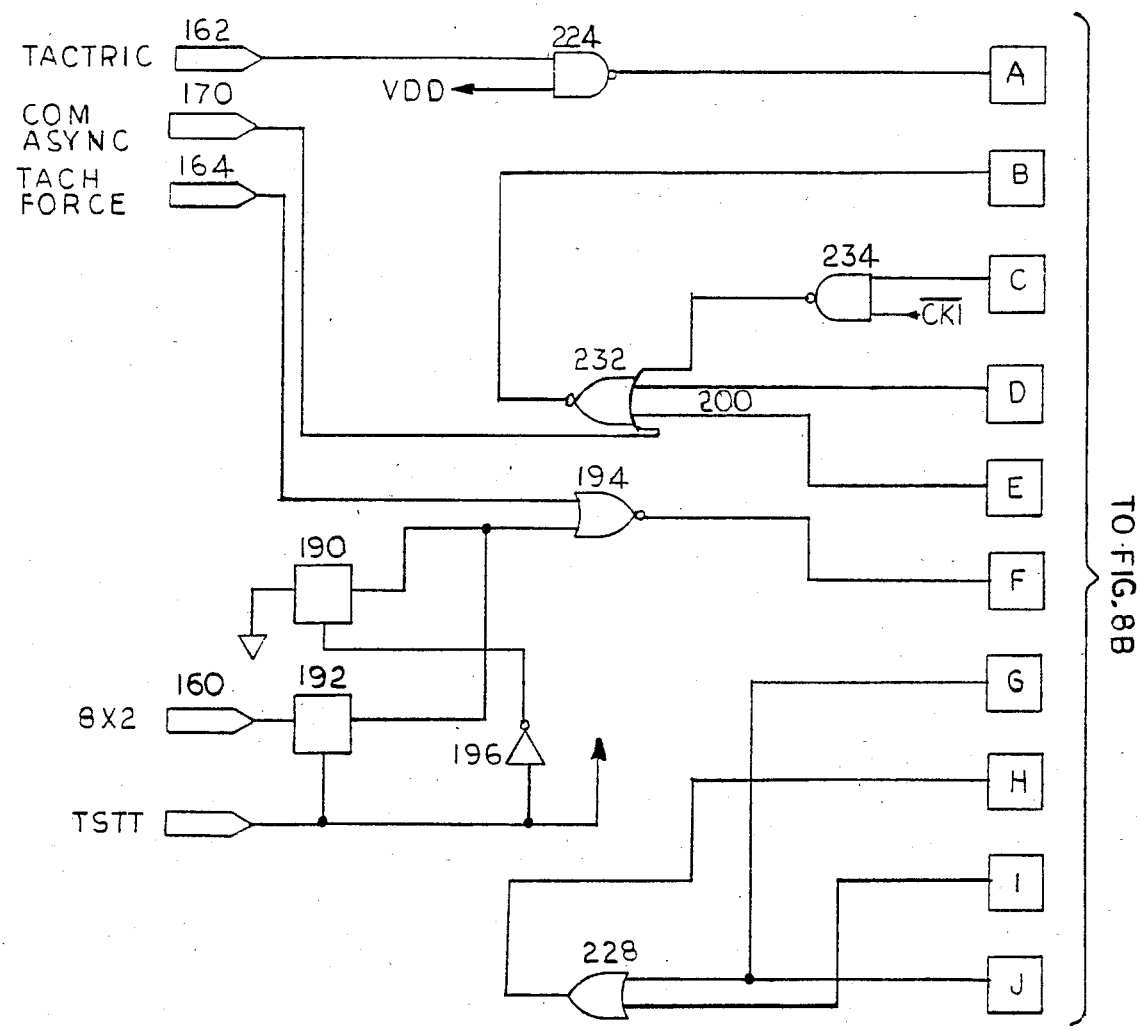
FIGS. 8A and B show the mode section of the pulse generator logic.

Referring to FIGS. 8A and B generally at 160 and 161 respectively, the determination of what modality is to be used for pacing is determined by the programmed modality in memory. The manifestation of this modality is input to the PGSL through the logic values of M-Mode 0 through 3 inputs to the PGSL at 172, 174, 176 and 178, respectively. The logic values "1" and "0" are input to quad D latch 238 which is clocked by the signal input at 240.

The stimulation modes are derived from the signal inputs from memory having logic values of "0" or "1". Combinations of the M-Mode 0–3 signals input at 172, 174, 176 and 178 through logic Gates form the logic values for the modalities, VOO, VVI, VVT, AOO, AAI, AAT, DOO, DVI, VDD, DDD and the new modalities of DDI and DDX. Combinations of the M-Mode 0–3 logic signals along with TACTRIG, 162, TACH FORCE, 164, VTACH, 180, and ATACH, 182 allow for the stimulation modalities for antitachycardia pacing which preempt the programmed modes.

Again referring to FIGS. 8A and B, the M-Mode 0 signal having a logic value of "0" or "1" at 172 is the first input to NOR Gate 204. The other two inputs to NOR Gate 204 are VTACH signal 180 and ATACH signal 182 which have a logic "0" value in normal operations. The output of NOR Gate 204 is input to inverter 202. The output of inverter 202 is input to latch 238 $D_0$, 242. This logic value output by inverter 202 is the same logic value as the one input at M-MODE 0, 172.

The M-Mode 1 input at 174 is connected to the input of inverter 206. The output of inverter 206 is connected to the input of NOR Gate 208. For this logic, the compliment of the M-Mode 1 logic value is input into NOR Gate 208. As long as VTACH signal 180 and ATACH signal 182 have a logic "0" value, this logic value of the output of NOR Gate 208, which is connected to $D_1$ input 244 of quad latch 238, will be the same logic value as the one input at M-MODE 1, 174.

The M-Mode 2 input at 176 is connected to the input of inverter 210. The output of inverter 210 is connected to the input of NOR Gate 212. The other input to NOR Gate 212 is the logic value of the VTACH signal at 180. Since the logic value of V TACH at 180 is normally "0", the output of NOR Gate 212 is determined by the logic value of the M Mode 2 input at 176. When the M-Mode 2 logic value at 176 is "1", the NOR Gate 212 output will be "1". When the M-Mode 2 logic value at 176 is "0", the output of NOR Gate 212 is "0".

The output of NOR Gate 212 is an input to the NOR Gate 214. The other input to NOR Gate 214 is the logic value of the ATACH signal at 182. Since the ATACH signal input at 182 is normally "0", the output of NOR Gate 212 will determine the output of NOR Gate 214 which is input to the $D_2$ input at 246 of latch 238.

Therefore, the compliment of the M-MODE 2 signal is output from NOR Gate 214 and input to the $D_2$ input 246 of QUAD latch 238. The M-Mode 3 input at 178 is connected to the input of inverter 216. The compliment of the M-Mode 3 logic value input is input to NOR Gate 220 as the third input.

The other two inputs to NOR Gate 220 are V TACH 180 and ATACH 182. The same criteria applies as was described for NOR Gate 208 regarding the VTACH and ATACH signals. So, the same logic value input at 178 after processing by inverter 216 and NOR Gate 220 is input at the $D_3$ input of quad latch 238.

The outputs of QUAD latch 238 at 242 ($D_0$), 244 ($D_1$), 246 ($D_2$) and 248 ($D_3$) follow the inputs when the clock input at 240 is a logic "1" value and are latched on a negative going clock pulse input at 240. Therefore, on each clock logic value of "1", the $Q_o$ output at 250 will output the logic value of the $D_o$ input at 242 and the $\overline{Q_o}$ output at 252 will be the compliment of $Q_o$; the $Q_1$ output at 254 will output the logic value of the $D_1$ input at 244, and the $\overline{Q_1}$ output at 256 will be the compliment of $Q_1$; the $Q_2$ output at 258 will output the logic value of the $D_2$ input at 246, and the $\overline{Q_2}$ output at 260 will be the compliment of $Q_2$; and the $Q_3$ output at 262 will be the output logic value of the $D_3$ input at 243, and the $\overline{Q_3}$ output will be the compliment of the $Q_3$ output.

DDX OPERATION

The DDX mode of operation is somewhat identical to the DDD mode of operation except when an R-wave is sensed, prior to atrial activity or atrial stimulus, it is assumed that is some type of premature activity. When this premature activity is sensed the timers are reset and instead of pacing in the DDD mode, the pacer will pace in forced DVI, or extend the atrial refractory period for one cycle only, unless additional premature activity is detected.

Referring to FIGS. 8A and B, the $\overline{DDX}$ mode signal is generated as the output of NAND Gate 236. The DDX mode is operative when the output of that Gate is a logic "0" value because it is a negative true logic. When this modality is in operation, the pacer will pace in the DDD mode unless a premature R-wave is sensed at $\overline{B-DET}$ at 384 in FIG. 9A. When this premature activity is sensed, the DDX mode will cause pacing in the forced DVI modality or, in a second embodiment, extend the atrial refractory period for the following cardiac cycle.

The DDX modality is set when M-MODE 0, 172, logic value is "1"; M-MODE 1, 174 logic value is "1"; M-MODE 2, 176, logic value is "1", and M-MODE 3, 178, logic value is "1".

The $Q_o$ output, at 250, will have a logic "1" value when the $D_o$ input has a logic value "1", which will be the M0 input to NAND Gate 236. The $Q_2$ output, at 260, will have a logic value of "1", when the $D_2$ input, at 246, has the logic value of "0". This logic "1" value is the M2 input to NAND Gate 236.

The third input to NAND Gate 236 is the output of AND Gate 292. The output of AND Gate 292 has a logic "1" value when both of its inputs have logic "1" values. The inputs to AND Gate 292 are the logic value of the $Q_1$ output, 254, from latch 238 output (the M1 signal); and the logic value of DUAL signal 350 which is the M3 signal 262. When the $D_1$ input is a logic "1" value, the M1 signal has a logic "1" value. DUAL signal 350 will have a logic "1" value when the $D_3$ input 248 to latch 238 has a logic value of "1". This will cause a logic "1" value to be output at the $Q_3$ output 262 of the latch as the M3 signal. This provides an M3 or DUAL signal with a logic value of "1".

The output of AND Gate 292, designated the VDD+DDD signal, will have a logic "1" value, which is input to NAND Gate 236.

Since the three input signals to NAND Gate 236 are logic "1" values, NAND Gate 236 will have a logic "0" value output, which is indicative of the DDX modality being operable. The pacer, once this modality is programmed, will pace in the DDD modality until premature activity is sensed, then it will pace in a forced DVI modality or extend the atrial refractory period as will be described subsequently.

Figure 13:
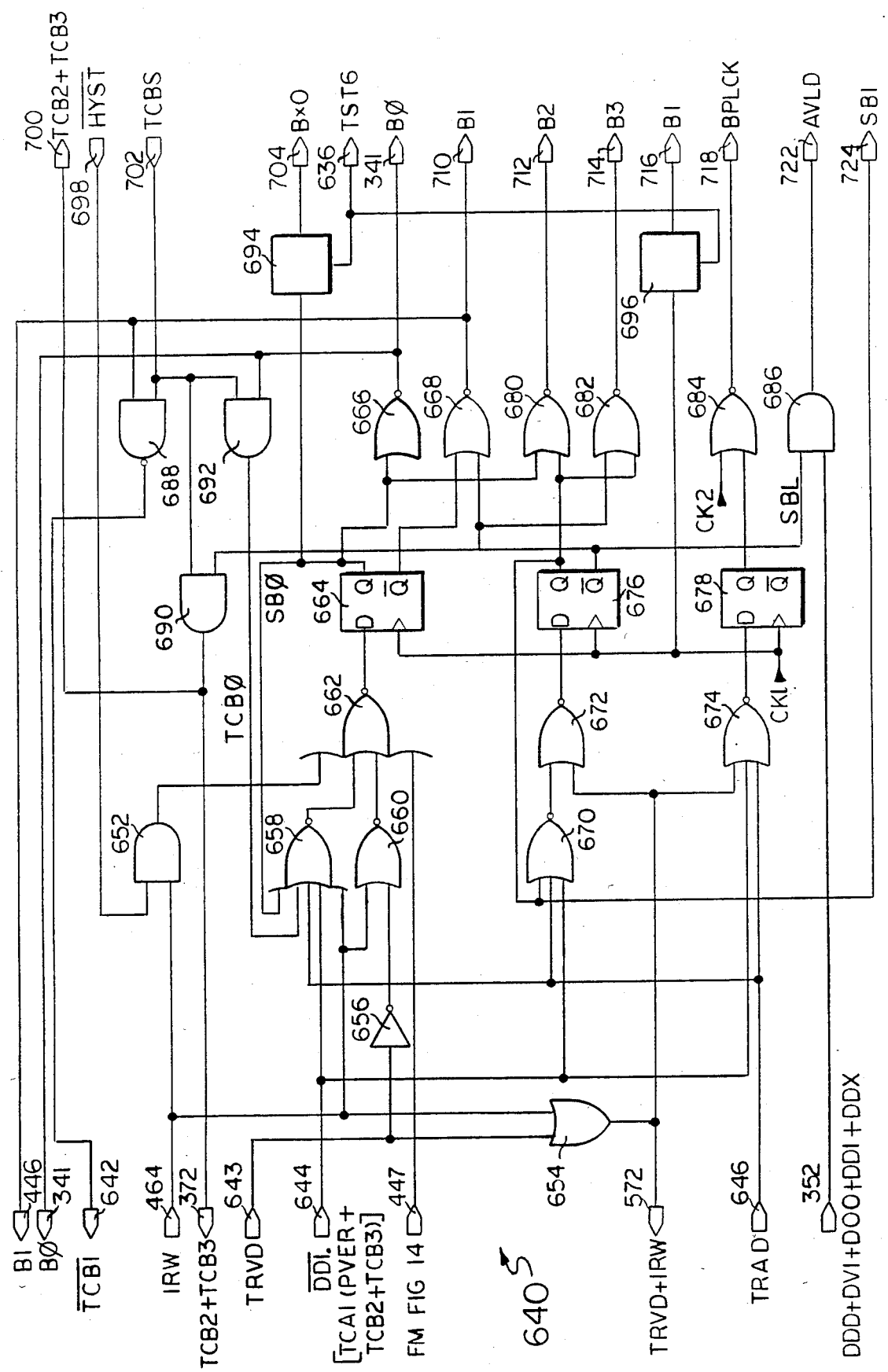
FIG. 13 shows the B-timer section of the pulse generator logic.
Figure 14:
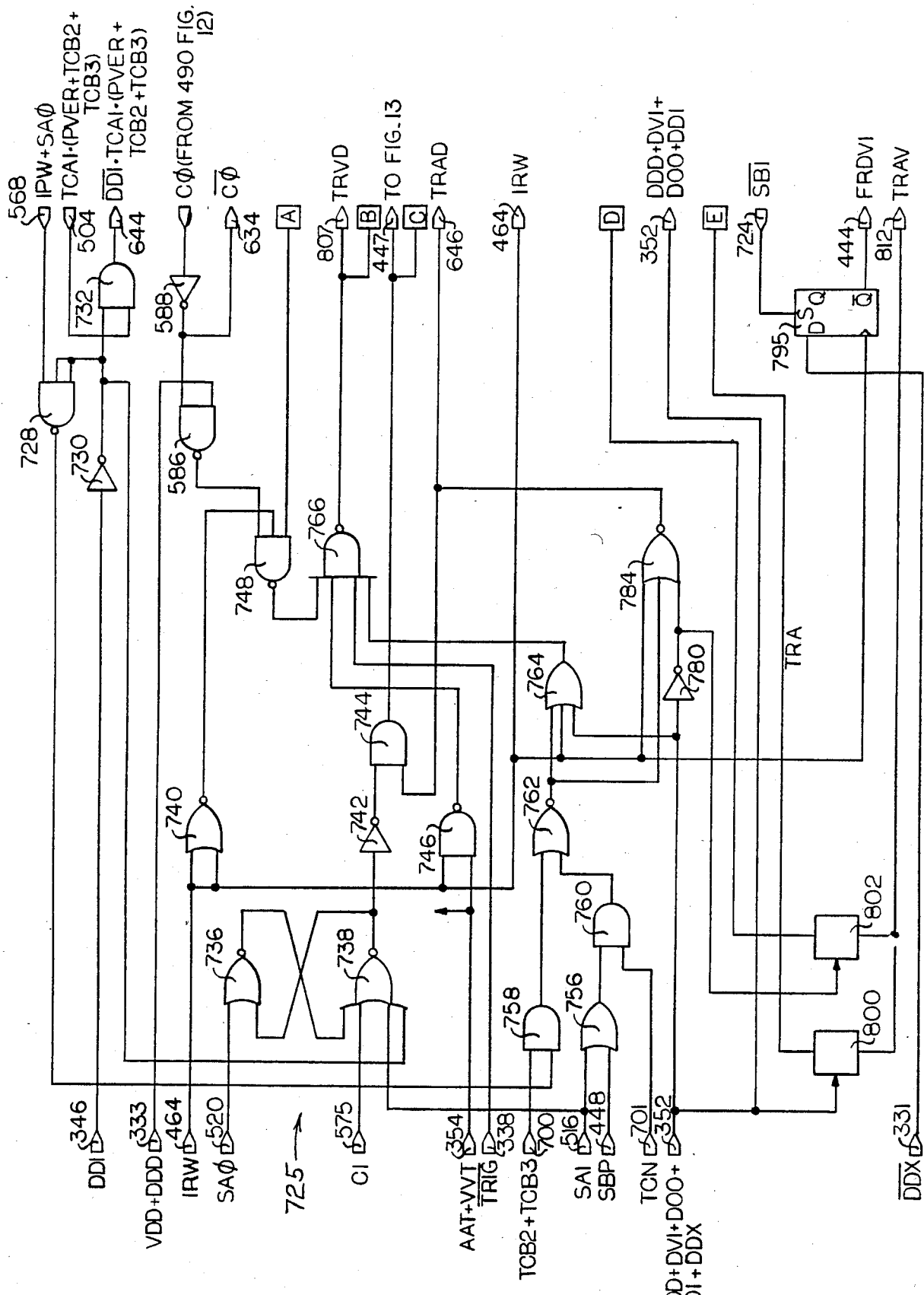
FIG. 14 shows the output section of the pulse generator logic.
Figure 14:
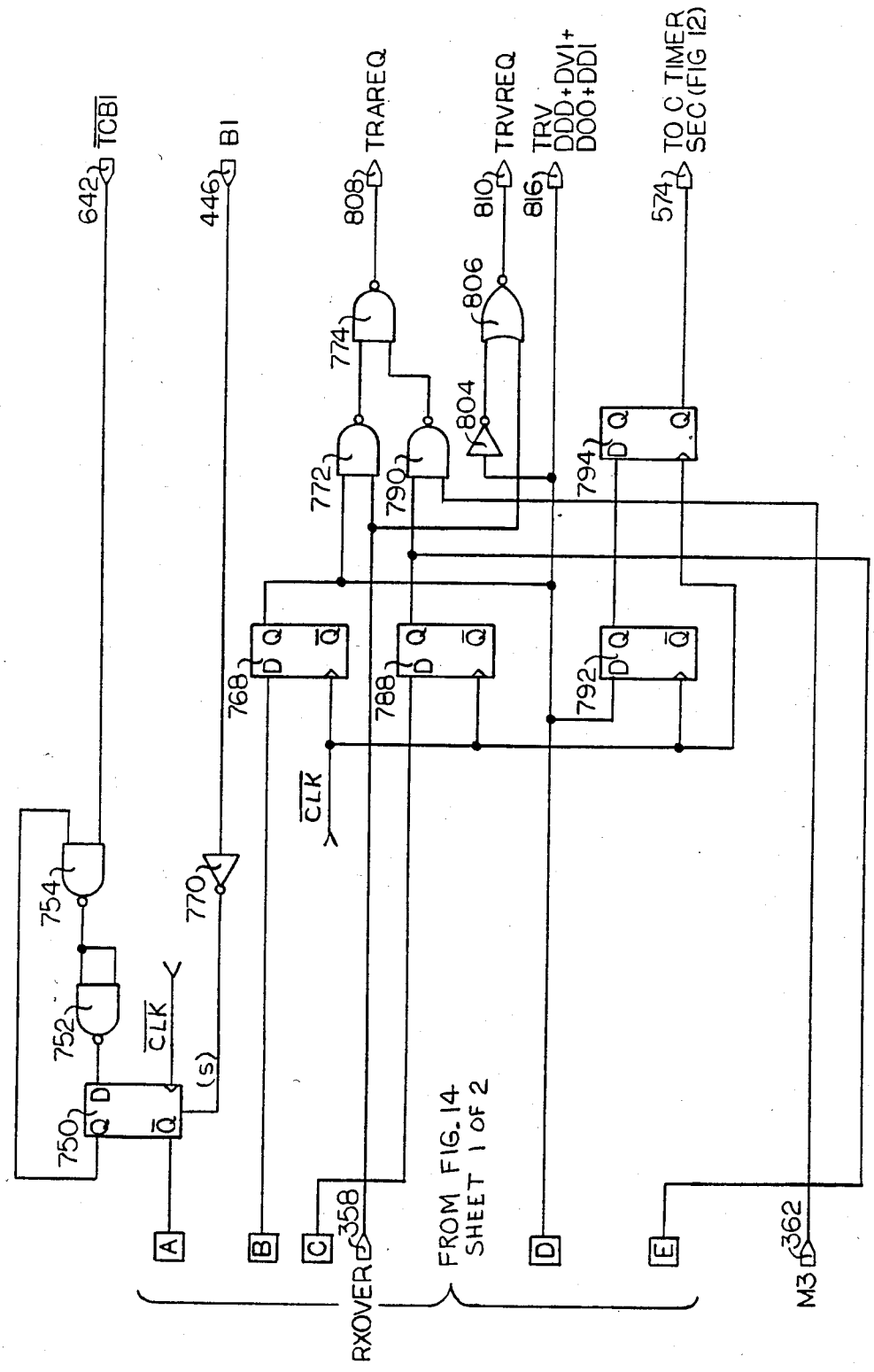

Referring to FIG. 14, $\overline{DDX}$ signal 331 having a logic "0" value is input to the D input of flip-flop 795. Flip-flop 795 is edge triggered. The clock pulse for flip-flop 795 is IRW signal 464. The set term for flip-flop 795 is $\overline{SB1}$ signal 724 output from flip-flop 676 (FIG. 13). Whenever the set term assumes a logic "1" value which means State B0, 71, (FIG. 2) or B1, 72 (FIG. 2) are set, then the Q output of flip-flop 795 assumes a logic "1" value and the $\overline{Q}$ output assumes a logic "0" value regardless of the clock condition or what the data input logic value is at the time the set input changes from a logic value of "0" to "1".

When the set input is a logic "0" value, the logic value of the $\overline{Q}$ of flip-flop 795 is determined by the logic value input to the D input at the time the flip-flop is clocked. When the DDX modality is programmed, the logic value loaded in the D input to flip-flop 795, is a logic "0" value. When the edge of the clock pulse clocks the flip-flop, which in this case is an IRW signal 464, the $\overline{Q}$ output will have a logic value of "1", which is FRDVI signal 444. When the stimulator is not in the DDX modality, the $\overline{DDX}$ signal will have a logic value of "1" and the output at $\overline{Q}$ will be a logic "0" value on the happening of a clocking edge of the clock pulse and FRDVI signal 444 will assume a logic "0" value.

Before describing the affect of FRDVI signal 444 on other logic circuitry, the signals that clock QUAD latch 238 and flip-flop 795 will be described. The generation of the logic values involves substantially all of the logic of the PGSL.

Figure 12:
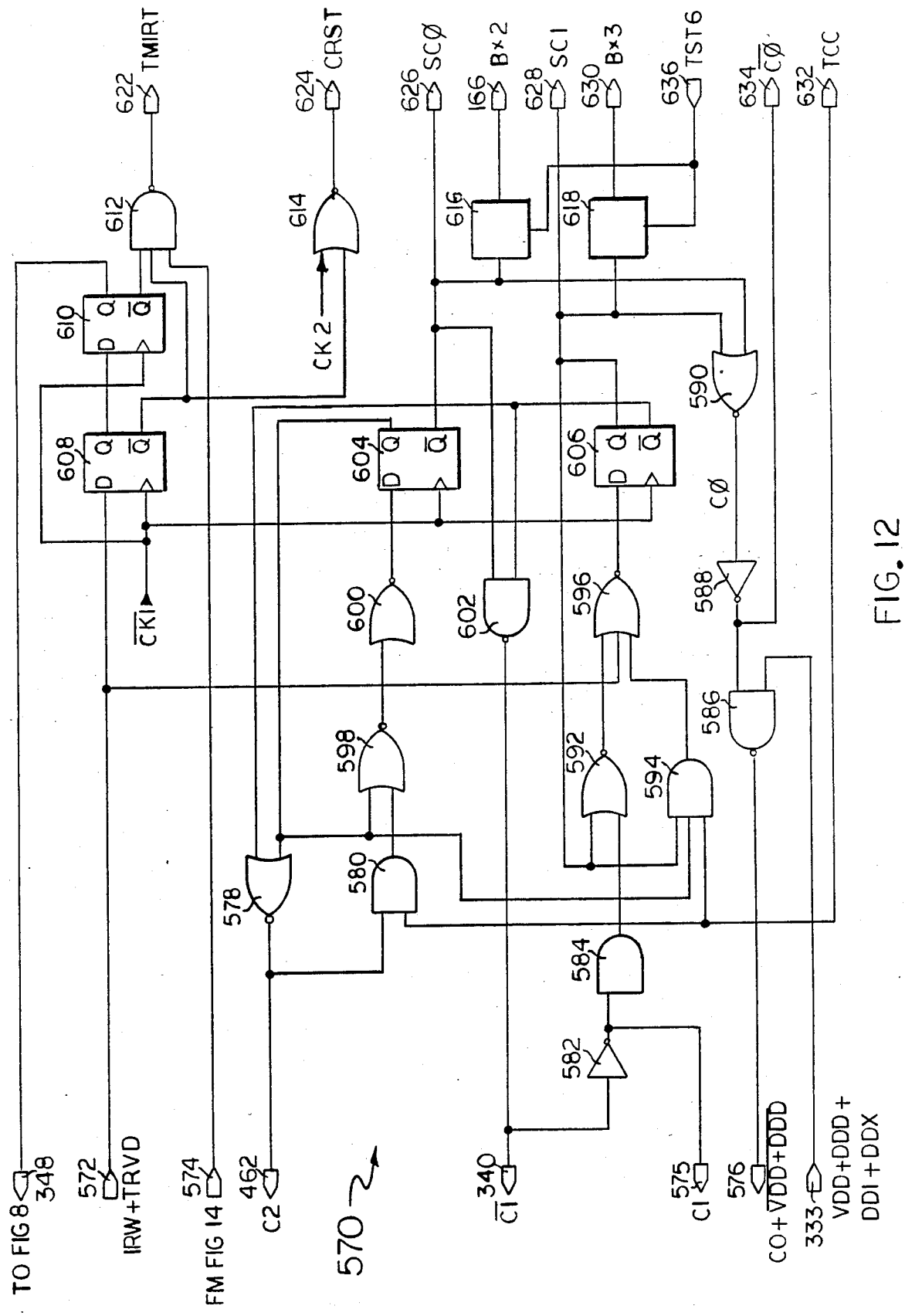
FIG. 12 shows the C-timer section of the pulse generator logic of the apparatus of invention.

The clock pulse that clocks latch 238 is generated in the C timer section of the PGSL shown in FIG. 12. Referring to FIG. 12, the clock pulse is the Q output of flip-flop 610. The Q output of flip-flop 610 will have a logic "1" value when the D input to that flip-flop has a logic "1" value when clocked. The D input to flip-flop 610 is connected to the Q output of flip-flop 608. In order for the Q output of flip-flop 608 to load the D input of flip-flop 610 with a logic "1" value, on the previous clock, the D input to flip-flop 608 had to have been loaded with a logic "1" value. The signal input to the D input of flip-flop 608 is the IRW+TRVD signal 572.

Referring to FIG. 13, IRW+TRVD signal, 572, is the output of OR Gate 654. The output of OR Gate 654 will have a logic value 1, when either the IRW input or the TRVD input or both have a logic value of "1". Additionally, it is this same IRW signal which clocks flip-flop 795 (FIG. 14).

Since the IRW signal is used in clocking flip-flop 795 and is one of the signals that can cause clocking of quad latch 238, the disclosure for obtaining a logic "1" value IRW signal will be described first and then the obtaining of a logic "1" value TRVD signal will be described. As will be explained subsequently, IRW with a logic "1" value can be generated in all B timer states except B0, C timer State C2 cannot be set; and the A timer must not be in State A2. For purposes of explanation, it will be assumed that the B timer is in State B1; the C timer in State C0 and the A timer is not in State A2.

Figure 9B:
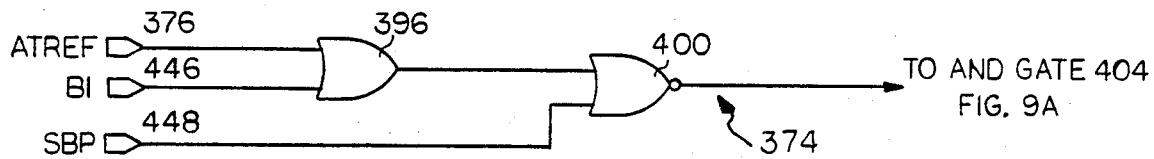
FIG. 9B shows a secondary embodiment for input of the ATREF signal in DDX modality for extension of the atrial refractory period.
Figure 9A:
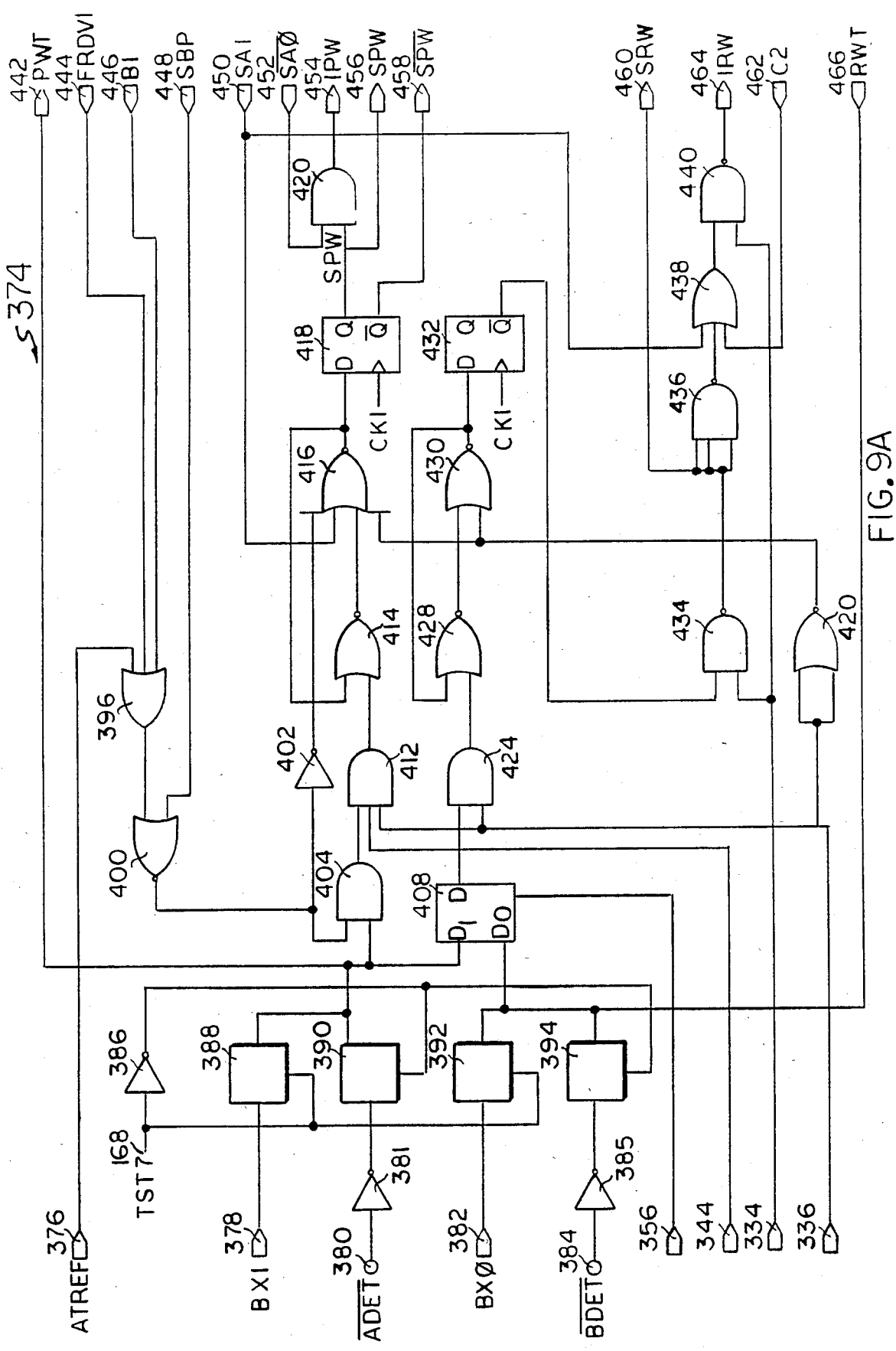
FIG. 9A shows the input section of the pulse generator logic.

Referring to FIG. 9A, IRW signal 464 is generated from the output of NAND Gate 440. IRW signal 464, is representative of an inhibiting R-wave. IRW 464 will inhibit the output of a ventricular pulse from the stimulator.

When a ventricular depolarization is sensed by the R-wave sensor 48, (FIG. 1) $\overline{B\text{-DET}}$ 384 has a logic "0" value. The logic "0" value is input to inverter 385 which provides as an output, the compliment of the input. The output logic value of inverter 385 is a logic "1" value. This logic "1" valve output of inverter 385 is input to transmission Gate 394.

Transmission Gate 394 will provide an output identical in logic value to its input if the control signal has a logic "1" value. The control signal is the $\overline{TST7}$ signal, which is the output of inverter 381. Since under normal conditions the apparatus operates in TST 0, the TST 7 signal will have a logic "0" value. The $\overline{TST7}$ signal having a logic "0" value passes through inverter 386 prior to input into the control input of transmission Gate 394. The logic "0" value is changed to its compliment, so a logic "1" value is provided to the control input to Gate 394, thus, turning it on.

When the control input has a logic "1" value, the logic "1" value input to the transmission Gate 392 is output. This signal is input to the $D_0$ input of MUX 408. The signal that is input to the $D_1$ input of MUX 408 is the output of transmission Gate 390, which is the logic value of the $\overline{A\text{-DET}}$ signal after passing through inverter 381.

Control signal 356 controls which input, $D_0$ or $D_1$ is output from the D output of MUX 408. When the control input is a logic "0" value, the $D_0$ input is output from the MUX. If the control input assumes a logic "1" value, the $D_1$ input is output. The control signal 356 is the output of NOR Gate 278 (FIG. 8B).

Referring to FIGS. 8A and B, the output of NOR Gate 278, ATRMD signal 356 is used as the control signal for MUX 408 as stated. There are two signals input to NOR Gate 278. These are $\overline{M2}$ signal 258 and M3 signal 262. The $\overline{M2}$ output 258 of QUAD latch 238 has a logic "0" value as previously described for the DDX modality. The M3 output, 262, as previously described for this modality, has a logic "1" value. So, the output of NOR Gate 278 will be a logic "0" value, which is signal 356. Therefore, this $D_0$ input of MUX 408 is output from the D output.

The output of MUX 408 is input to AND Gate 424 as the first input. The second input to AND Gate 424 is signal 336 which is the output of NOR Gate 232 (FIG. 8A). The output of NOR Gate 232 has a logic "1" value when the apparatus is not absolutely refractory to sensing for R-waves or P-waves.

The description of the signals that are input to NOR Gate 232 involve the mode section shown in FIG. 9A; the B Timer section of the PGSL,, shown in FIG. 13, and the C Timer section of the PGSL shown in FIG. 12. As previously stated it is assumed that the B timer is in State B1 and the C timer is in State C0 and the A timer is not in State A2 for purposes of example. The description of the various signals will be so based.

Referring to FIG. 8A, the first input to NOR Gate 232 is the COMASYNC signal 170. This signal forces asynchronous pacing by the stimulator during analog measurements. Therefore, except when these analog measurements are being performed, this signal has a logic "0" value.

The second signal input to NOR Gate 232 is ZOO signal which is the output of NOR Gate 266. The two inputs to NOR Gate 266 are the M0 signal, 250 and the M1 signal, 254 output from quad latch 238. As previously described for the DDX modality, both the M0 and M1 logic values are "1". Therefore, by applying these logic "1" values as inputs to NOR Gate 266, the output logic value of that Gate is "0" which is input to NOR Gate 232.

The third input to NOR Gate 232 is the B0 signal from the B timer section of the PGSL shown in FIG. 13. First the B0 signal will be briefly discussed, then the logic will be discussed considering the B timer in State B1 which is one of the three states of the B timer in which an IRW having a logic "1" value can be generated.

The B0 signal is indicative of the B timer State for blanking period in the atrium and ventricle. B0 signal, 341 is the output of NOR Gate 666 in FIG. 13. The inputs to NOR Gate 666 are the outputs from the B State flipflops 664 and 676. The outputs of these flipflops determine the B timer State. The States of the B timer represented by the SB1 and SB0 logic values in the following table:

TABLE 1

| B Counter State | SB1 | SB0 |
|---|---|---|
| B0 | 0 | 0 |
| B1 | 0 | 1 |
| B2 | 1 | 0 |
| B3 | 1 | 1 |

The SB0 State signal is the Q output of State flip-flop 664. The SB1 State signal is the $\overline{Q}$ output of State flip-flop 676. When both inputs to NOR Gate 666 have a logic value of "0", the output will have a logic value of "1", indicating that the State the B timer is in State B0, indicative the blanking period. When this is true, the logic "1" value output of NOR Gate 666 will cause the output of NOR Gate 232 to change from a logic "1" value to a logic "0" value. However, during the remaining B counter States (i.e., B1, B2, B3) an R-wave can be detected and the output of NOR gate 666, correspondingly, is a logic "0" value, which is input to NOR Gate 232 causing the desired output of a logic "" value.

To explain how the preceding is possible, the B timer section of the PGSL will be discussed assuming the B timer is in State B1. In this state it is possible to produce an IRW with a logic "1" value. However, it is to be understood that this could be either State B1, B2 or B3.

The B1 State of the B timer, is the B counter State in which there is sensing for venticular activity. As was shown in Table 1 for the B1 State, SB1 and SB0 have the respective logic values of "0" and "1".

Sensing R-waves in the B2 or B3 States, which will be classified premature activity, PVC, will be discussed subsequently in regard to the changing of pacing in the DDD modality to the DVI modality or the extension of the atrial refractory period.

Referring to FIG. 13, the B1 State has been entered from B0 and an IRW can occur. For State B1, the SB1 logic value is "0" and the SB0 logic value "1". To output these logic values, the D input to flip-flop 664 must have been a logic "1" value and the D input to flip-flop 676 must have been a logic "1" value upon the occurrence positive edge clock pulse $\overline{CK1}$, 167.

A clocked set/reset latch is formed by NOR Gate 658, NOR Gate 662 and flip-flop 664. The output of NOR Gate 662 is input to the D of flip-flop 664. For State B1, the output of NOR Gate 662 is a logic "1" value. In order for the output of NOR Gate 662 to be a logic "1" value, all of the inputs must have a logic "0" value.

The first signal input to NOR Gate 662 is the output of AND Gate 652. The inputs to AND Gate 652 are $\overline{HYST}$ signal 698 and the present IRW signal. The present IRW logic "0" value. The $\overline{HYST}$ input has a logic "0" value when hysteresis is programmed. It will be assumed that hysteresis is programmed so its logic value is "0". Therefore, the output logic value of AND Gate 652 is "0", since the IRW signal and $\overline{HYST}$ signal both have logic "0" values. This logic "0" value is input to NOR Gate 662 as the first input.

The second signal input to NOR Gate 662 is the output of NOR Gate 658. The first input to NOR Gate 658 is the SB0 signal output from flip-flop 664 which is fed back as an input to that Gate. This signal has a logic "1" value in State B1 as shown in Table 1. The second input to NOR Gate 658 is the TCB0 signal output from AND Gate 692. The inputs to that AND Gate are the output of NOR Gate 666 for State B0 and the TCBS signal 702. The logic value output from NOR Gate 666 during State B1 is a logic "0" value. TCBS signal 702, for representing a terminal count on the B counter has a logic "0" value before a complete counting out of the B timer State it is in. The generation of TCBS signal 702 requires lengthy description and will be described in detail subsequently.

Since both inputs to AND Gate 692 are logic "0" values, the output logic value is "0" which is input to NOR Gate 658.

The third input to NOR Gate 658 is TRAD signal 646. TRAD signal 646 is generated from the output of NOR Gate 784 (FIG. 14). Referring to FIG. 14, the first input to NOR Gate 784 is the present IRW signal which has a logic "0" value. The second input to NOR Gate 784 is the output of NOR Gate 762. The output of NOR Gate 762 is determined by the output of AND Gate 758, OR Gate 756 and AND Gate 760.

As stated, the A timer is not in State A2, therefore, the logic value of SA1 signal 516 is a logic "0" value (as is shown in Table 3 subsequently), which is the first input to OR Gate 756. The second input to OR Gate 756 is SBP signal 448. Although it has been stated that the B timer is in State B1, the C timer is in State C0; and the A timer is not in State A2, there would be no clue as to the logic value of the SBP when these conditions are set. The SBP signal will have the logic value which it had during State B2 or B3 of the previous cycle. If the PVER signal had a logic "1" value during the last duty cycle, the resulting SBP signal has a logic "0" value indicative of the passage of the P-wave verification test. If, however, there was failure of the P-wave verification test, the PVER signal will have a logic "0" value and SBP signal 448 will have a logic "1" value indicative of noise being sensed on the R-wave channel.

For exemplary purposes, it is assumed that the PVER output from the Q output of flip-flop 478 is a logic "0" value, and further that during the previous cycle SBP signal 448 had a logic "0" value. Having these conditions set the generation of a logic "1" value SBP signal will be described.

Figure 10:
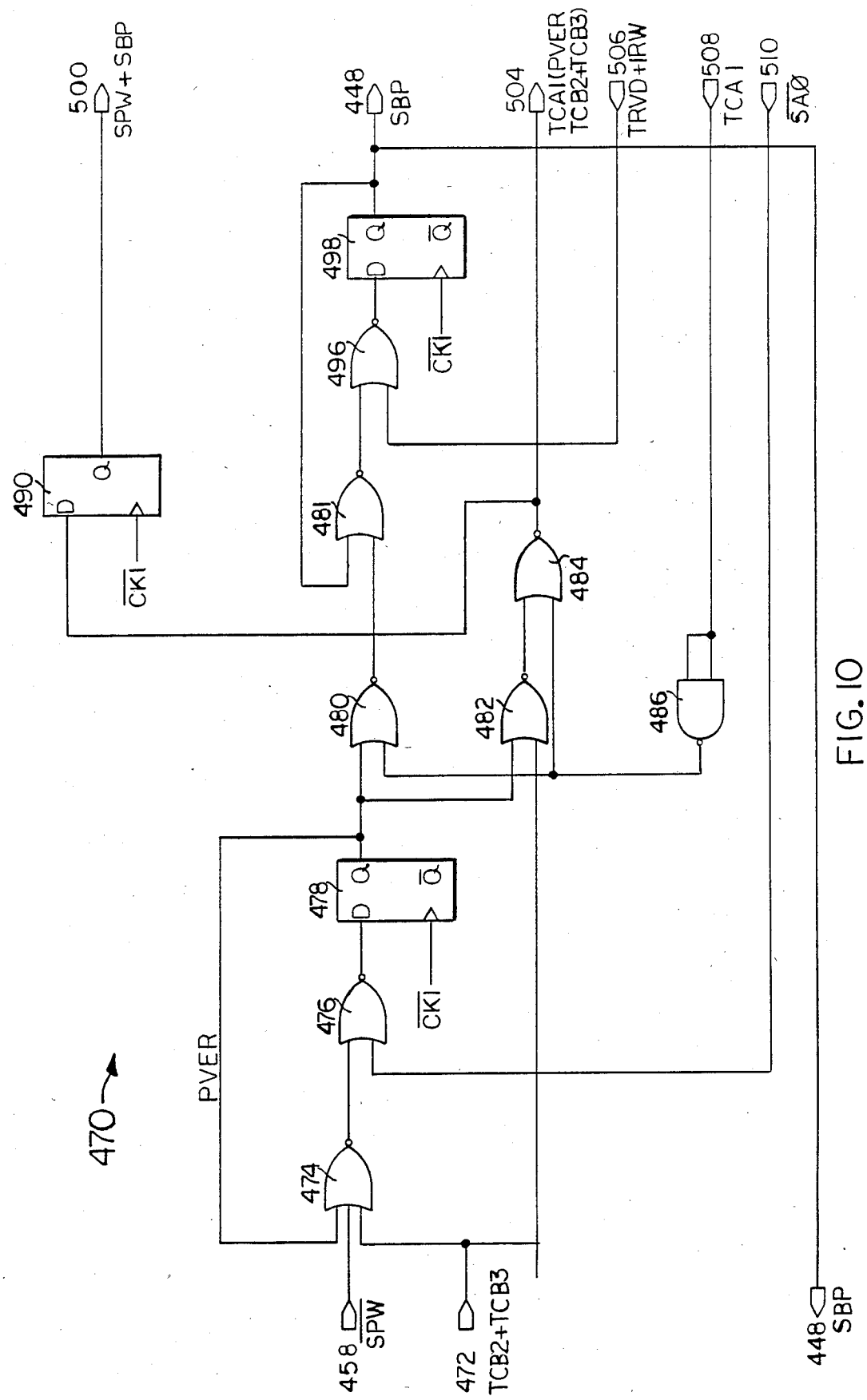
FIG. 10 shows the P-wave verification section of the pulse generator logic.

Referring to FIG. 10, NOR Gate 481, NOR Gate 496 and flip-flop 498 form a clocked set/reset latch. The PVER signal having a logic "0" value is input to NOR Gate 480 as a first input. The second input to NOR Gate 480 is the output of NAND Gate 486. In order to have an SBP signal with a logic "1" value, there must be a failure of the P-wave verification test resulting in PVER having a logic "0" value, and a timing out of the A timer State A1. This would mean that TCA1 signal 508 has a logic "1" value. When this is the case, a logic "1" value is input to the tied inputs of NAND Gate 486. This results in a logic "0" output which is input to NOR Gate 480. Since the two inputs to NOR Gate 480 are logic "0" values, the input of that gate is a logic "1" value, which is input to NOR Gate 481 as a first input.

The second input to NOR Gate 481 is the Q output of flip-flop 478 which is in a feedback loop to NOR Gate 481. This signal is the existing SBP signal and has a logic "0" value. Therefore, since both inputs to NOR Gate 481 are not logic "0" values, the output is a logic "0" value which is input to NOR Gate 496 as the first input.

The second input to NOR Gate 496 is TRVD+IRW signal 506. This signal is a reset signal, which will clear out SBP signal 502 having a logic "1" value, at the end or by the end to State B1. This signal, since generation of an IRW signal is based on a sensed R-wave, is a logic "0" value. Since both signals input to NOR Gate 496 are logic "0" values, the output logic value of that gate is a logic "1" value, which is input to the D input of flip-flop 498. On the positive edge of $\overline{CK1}$ signal 167, the Q output will assume a logic "1" value which is SBP signal 502 indicative of failure of the P-wave verification test.

Again referring to FIG. 14, SBP signal 448 will be assumed to have a logic "0" value from the previous cycle even though there was a description of the generation of SBP signal having a logic "1" value. This logic "0" value is input to OR Gate 756 as the second input. Since both inputs to OR Gate are logic "0" values, the output of OR Gate 756 is a logic "0" value which is input to AND Gate 760 as a first input.

The second input to AND Gate 760 is TCN signal 701. First an explanation of TCN signal 701 will be set forth describing the condition which must be present in order for it to assume a logic "1" value.

Figure 18:
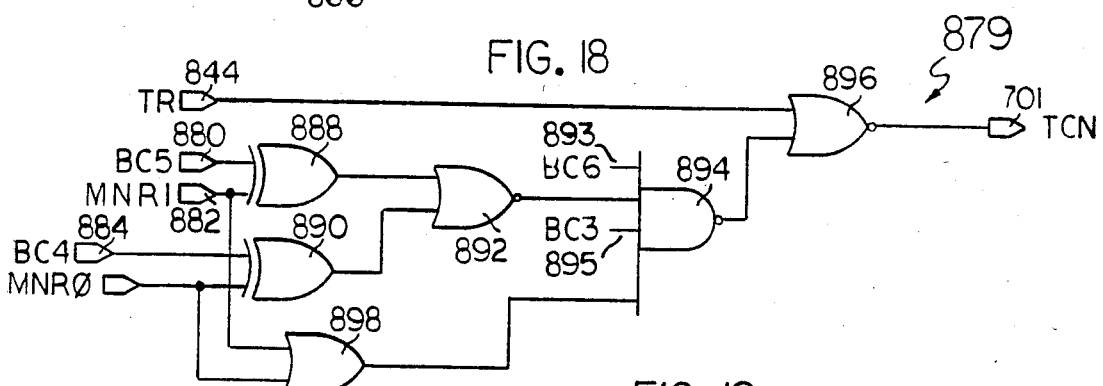
FIG. 18 shows logic of the noise counter of the B-timer.

Referring to FIG. 18, TCN signal 701 is the output of logic circuitry of a comparator in the B timer. TCN signal 701 is the terminal count on the noise rate counter. This comparator is incorporated in the logic circuitry of the apparatus, so that in the presence of noise on the P or R channel, it will prevent asynchronous pacing by the apparatus which can be competitive with natural depolarizations of the heart tissue in the presence of noise. Therefore, in the presence of noise, the apparatus will pace faster than the basic rate.

When noise is on the R channel, the ventricular refractory period will be extended until time out of the programmed period of TCN resulting in an early TRA. Also when there is noise on the P-channel, there will be an early TRA pulse from the apparatus.

Figure 20A:
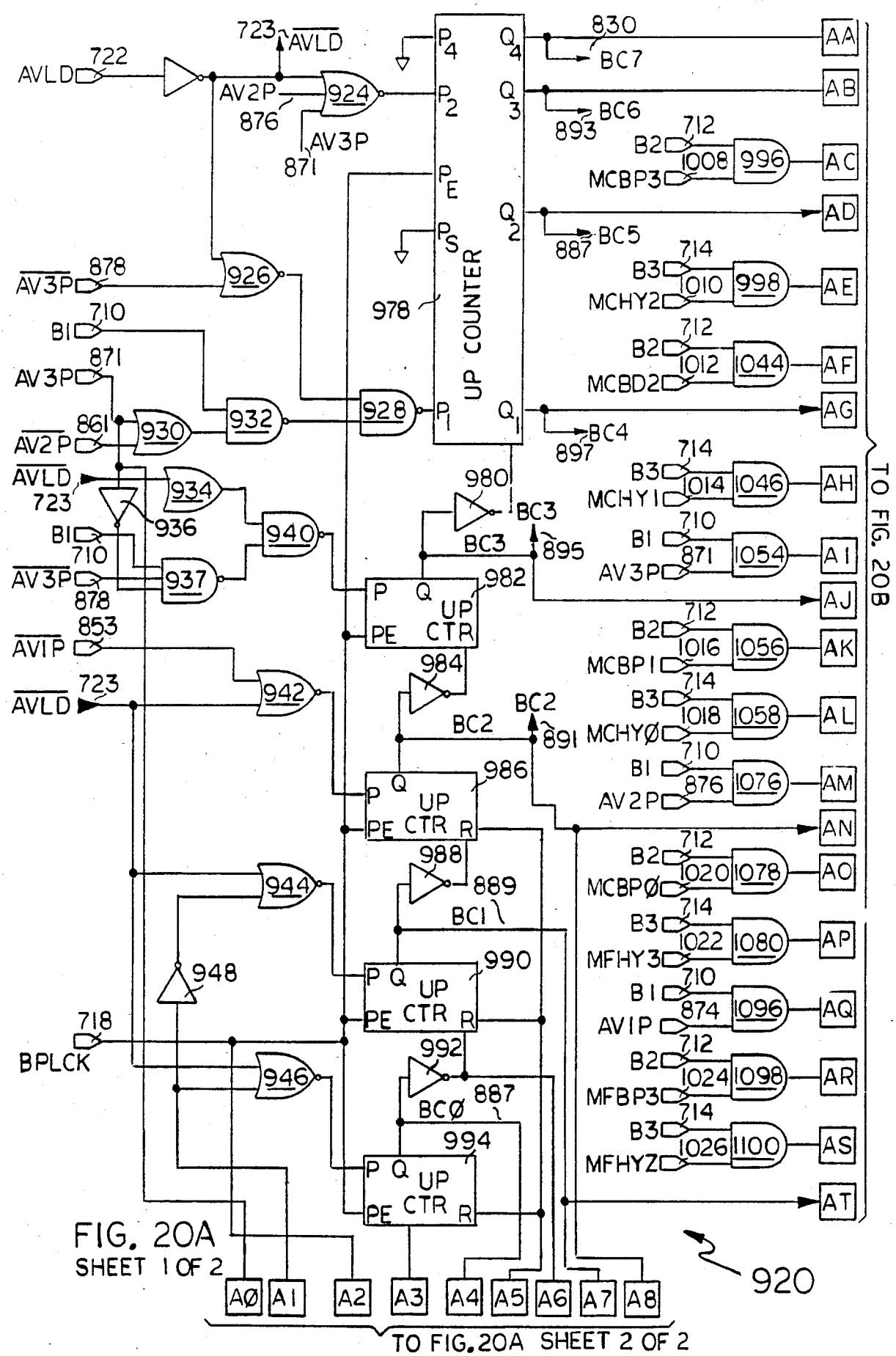
FIG. 20A shows the B-timer logic less the logic circuits of FIGS. 11, 12 13, 16, 17, 18, and 19.
Figure 20A:
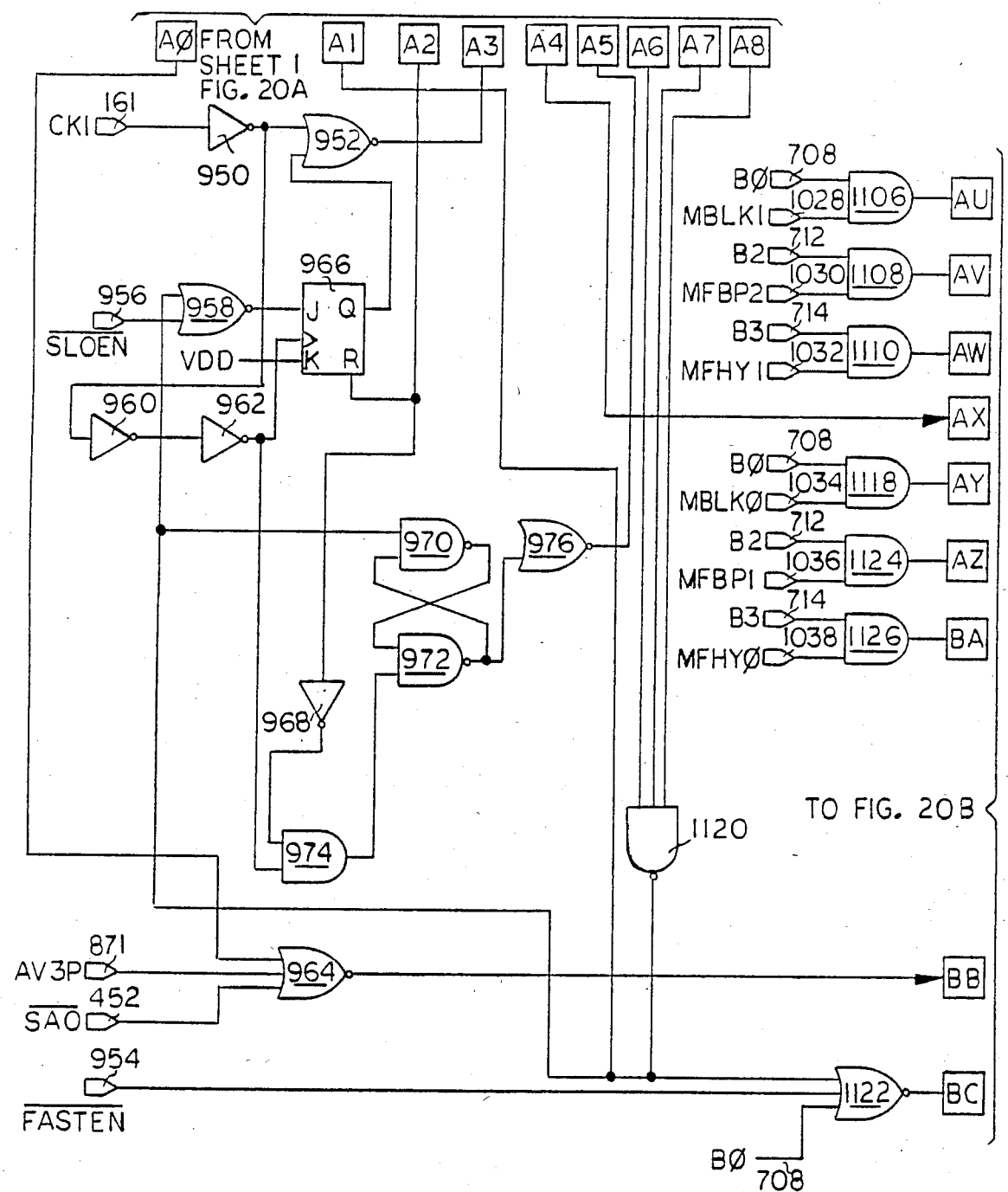

The TCN counter is a comparator in the B timer shown generally at 920 in FIGS. 20A and B. The logic gates associated with generation of TCN signal 701 is generally shown at 879 of FIG. 18 even though this is part of the B timer. In order to completely describe generation of the logic value of TCN signal 701, a description of the B timer is necessary. However, at this point in the description, a disclosure of the TCN logic circuitry will follow with reference to the signal generated in the main B timer which will be described completely at a later point in this disclosure.

Again referring to FIG. 18 the noise comparator is generally shown at 879. TCN is programmable based on the following table:

TABLE 2

| MNR 1 | MNR 0 | Rate |
|---|---|---|
| 0 | 0 | Basic rate |
| 0 | 1 | 560 ms. (110 ppm.) |
| 1 | 0 | 660 ms. (90 ppm.) |
| 1 | 1 | 760 ms. (80 ppm.) |

For purposes of explanation, it will be assumed that the terminal count of the comparator is set at 560 ms.

The following will be a description of the production of a TCN signal having a logic "1" value. It is assumed that 560 ms. have elapsed which is the programmed rate.

The output of NOR Gate 896 is TCN signal 701. This will have a logic "1" value when the inputs to NOR Gate 896 are both logic "0" values. The first input to NOR Gate 896 is TR signal 844. This signal is special 30 bpm command which a physician uses for test purposes, therefore, its logic value is normally a logic "0" value. It is therefore assumed that it has a logic "0" value. The second input to NOR Gate is the output of NAND Gate 894.

The first input to NAND Gate 894 is BC6 signal 893 which is output from the B timer. This signal will have a logic "1" value every 406 ms. Since 560 ms. have elapsed, BC6 has a logic "1" value which is input as the first input to NAND Gate 894. The second input to NAND Gate 894 is the output of NOR Gate 892. The inputs to this gate are the respective outputs of XOR Gate 888 and XOR Gate 890.

The first input to XOR Gate 888 is BC5 signal 880 which is an output of the B timer. The logic signal will have a logic "1" value every 203 ms. However, this added to BC6 signal would yield a count of 609 ms. which is greater than the programmed 560 ms. Therefore, BC5 signal 880 will have a logic "0" value. The second input is to XOR Gate 888 is MNR1 signal 882 which has a logic "0" value as indicated in Table 2. Since both inputs are logic "0" values, the output of XOR Gate 888 is a logic "0" value which is input to NOR Gate 892 as the first input.

The first input to XOR Gate 890 is BC4 signal 884 output from the B timer. This signal has a logic "1" value every 102 ms. This added to BC6 signal 893 would be a count of 506 ms. So this signal has a logic "1" value. The second input to XOR Gate 890 is MNR0 signal 886 which has a logic "1" value as shown in Table 2. Since both inputs are a logic "1" value, the output of XOR Gate 890 is a logic "0" value.

Both inputs to NOR Gate 892 are logic "0" values, so the output of that gate is a logic "1" value. This logic "1" value is the second input to NAND Gate 894.

The third input to NAND Gate 894 is BC3 signal 895, output from the B timer. This signal has a logic "1" value every 50 ms., so when added to BC6 signal 893 and BC4 signal 884 the elapsed period is 560 ms. Therefore, BC3 signal 895 will have a logic "1" value.

The fourth input to NAND Gate 894 is the output of OR Gate 898. The inputs to OR Gate 898 is MNR1 signal 882 and MNR0 signal 886. Since MNR0 signal 886 has a logic "1" value, the output of OR Gate 898 is a logic "1" value. Since all of the inputs to NAND Gate 894 are logic "1" values, the output logic value is a logic "0" value which is the second input to NOR Gate 896. Both inputs to NOR Gate 896 are logic "0" values, therefore, the output logic value is "1", which is TCN signal 701.

For purposes of the generation of an IRW signal with a logic "1" value, it has been previously set forth that the B timer is in State B1. The shortest time in which TCN signal 701 can have a logic "1" value is 560 ms. from initiation of the pacer cycle. The longest programmable period for B1 is 240 ms. Therefore, in B timer State B1, TCN can never assume a logic "1" value. So, referring to FIG. 14, TCN signal 701 input to AND Gate 760 will have a logic "0" value. Since one of the inputs to AND Gate 760 is a logic "0" value, the output logic value of that gate is a logic "0" value. So the second input to NOR Gate 762 is a logic "0" value.

The first input to NOR Gate 762 is the output of AND Gate 758. The first signal input to that gate is TCB2+TCB3 signal 472 which has a logic "0" value in State B1. Since this signal is a logic "0" value, the output of AND Gate 758 is a logic "0" value regardless of the logic value of the other input.

Since both inputs to NOR Gate 762 are logic "0" values, the output logic value of NOR Gate 762 is a logic "1" value. This logic value is input to 784 as the second input.

The first input to NOR Gate 784 is the present IRW signal which as described has a logic "0" value.

The third input to NOR Gate 784 is the $\overline{DDD+DVI+DOO+DDI+DDX}$ signal which is output from inverter 780. This signal is the compliment of DDD+DVI+DOO+DDI+DDX signal 352.

Figure 8A:
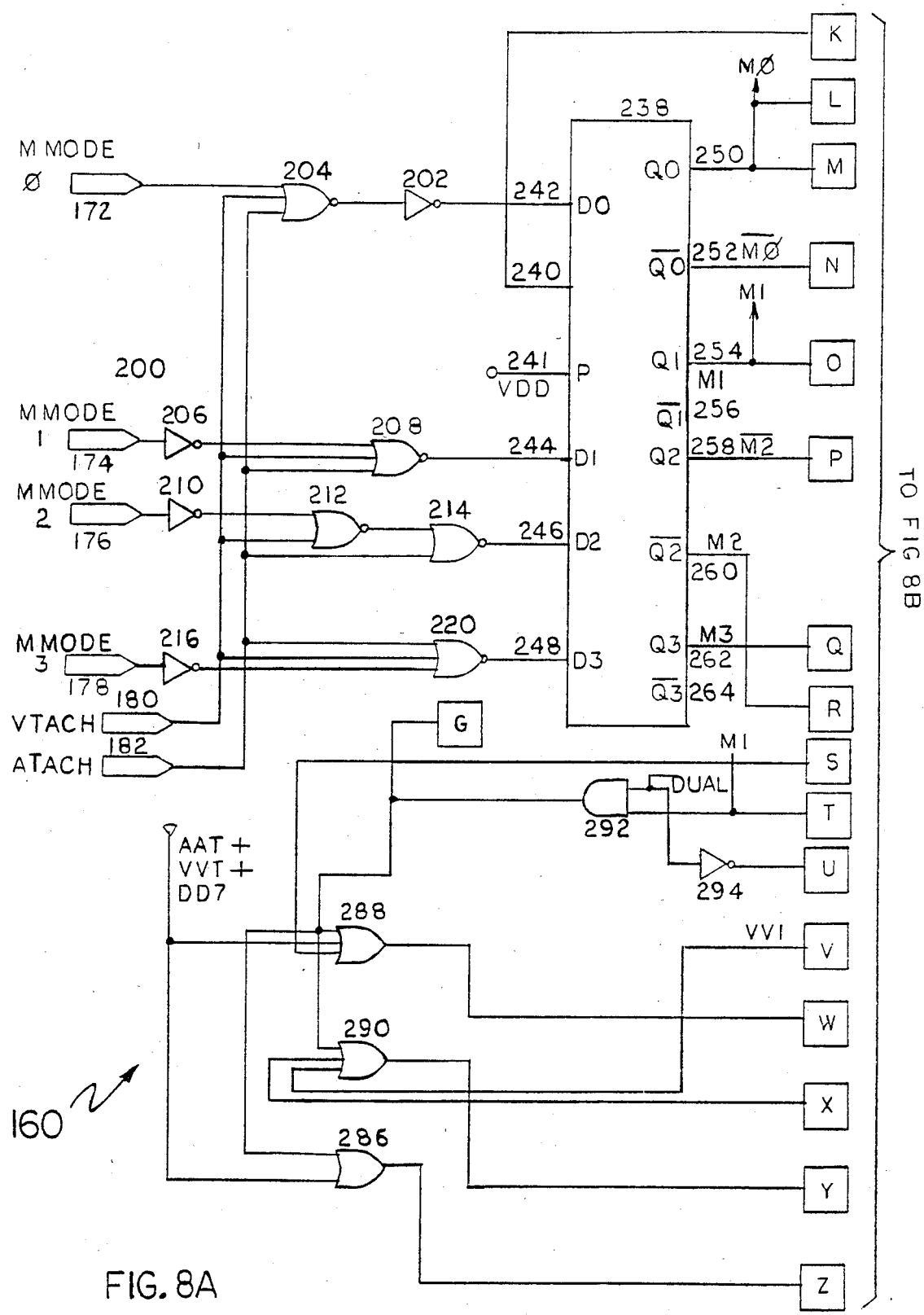

Referring to FIG. 8, DDD+DVI+DOO+DDI+DDX signal 352 is the output of NAND Gate 312. The gates which determine the output of NAND Gate 312 are NOR Gate 266, NAND Gate 306 and NAND Gate 308. NOR Gate 266 has inputs from the M0 output, 250, and the M1 output, 254, of quad latch 238. As previously described for this modality, both M0 and M1 have logic "1" values. Therefore, the output of NOR Gate 266 is a logic "0" value, which is input to NAND Gate 308 as the first input. The second input to NAND Gate 308 is DUAL signal 350, previously described as having a logic "1" value. Since the logic values input to NAND Gate 308 are a logic "0" and logic "1" value, the output logic "1" value. This is input to NAND Gate 312 as the second input.

The first input to NAND Gate 312 is the output of NAND Gate 306. The first input to that gate is M0 signal 250 which is logic "1" value and the second input the M3 signal 262, which also has a logic "1" value.

Therefore, the output of NAND Gate 306 is a logic "0" value, which is input to NAND Gate 312.

Since the logic value inputs to NAND Gate 312 are a logic "0" value and a logic "1" value, the output logic value of NAND Gate 312 is a logic "1" value which is DDO+DVI+DOO+DDI+DDX signal 352. This signal is input to inverter 780. So the output of inverter 780 is a logic "0" value, which is input as the third input to NOR Gate 784.

Referring to FIG. 14, since all of the input logic values to NOR Gate 784 are not logic "0" values, the output of NOR Gate 784 is a logic "0" value. This signal is the TRAD signal 646 input as the third input to NOR Gate 658 (FIG. 13).

The fourth signal input to NOR Gate 658 is the output of AND Gate 732 (FIG. 14). This gate synchronizes the timing of the B State timer with verified P-wave events.

Referring to FIG. 14, the first input to AND Gate 732 is signal 504 which is output from NOR Gate 484 in FIG. 10. Referring to FIG. 10, NOR Gate 474, NOR Gate 476, and flip-flop 478 form a clocked latch which along with NOR Gate 482 and TCA1 signal 508 determine the logic value output by NOR Gate 484.

There are three inputs to NOR Gate 474. The first input is the TCB2+TCB3 signal 472, which has a logic value of "0" while the B timer is in State B1. The second signal input to NOR Gate is $\overline{SPW}$ signal 458. The logic value of this signal in the B1 State is a logic "1" value as will be explained subsequently. The third input is the feedback from the output of flip-flop 478 which will be assumed to be a logic "0" value for the purposes of example.

The output of NOR Gate 474 is a logic "0" value, which is input to NOR Gate 476 as the first input. The second input to NOR Gate 476 is the $\overline{SA0}$ signal 510 output from the A State flip-flop 548 shown in FIG. 11.

As previously stated, the A timer is not in State A2. In State B1, atrial sensing is refractory so the A timer is in State A0 or A2. The state logic for the A timer is shown in the following table:

TABLE 3

| A Counter State | SA1 | SA0 |
|---|---|---|
| A0 | 0 | 0 |
| A1 | 0 | 1 |
| A2 | 1 | 0 |

$\overline{SA0}$ signal 510 will have a logic "1" value since the A timer is in State A0 or A2. This logic "1" value is input to NOR Gate 476. Since this input has a logic "1" value, NOR Gate 476 will have a logic "1" value, the output is a logic "0" value which is input in the D input to flip-flop 478. On the positive clock edge of $\overline{CK1}$ signal 167, a logic "0" value is output from the flip-flop.

The logic "0" value output from flip-flop 478 is input to NOR Gate 482. The second input to NOR Gate 482 is the TCB2+TCB3 signal having a logic value of "0" as previously described. The output of NOR Gate 482 has a logic "1" value which is input as the first signal to NOR Gate 484. The second signal input to NOR Gate 484 is the output of NAND Gate 486. As stated, the A counter State is not in A2, so TCA1 signal 502 has a logic "0" value. The tied inputs to NAND Gate 486 are logic "0" values so the output is a logic "1" value provided as the second input to NOR Gate 484.

When the logic values input to NOR Gate 484 are both logic "1" values, the output is a logic "0" value.

This signal designated TCA1 (PVER+TCB2+TCB3), 504, is applied to an input of AND Gate 732 in FIG. 14.

Referring again to FIG. 14, AND Gate 732 has as a second input, the compliment of DDI signal 346. DDI signal 346 has a logic "1" value only when that modality is programmed. Since the DDX modality is programmed, the DDI signal has a logic "0" value. The DDI signal is input to inverter 730, which will change the logic value from "0" to "1" and is the $\overline{DDI}$ signal. This logic "1" value is applied as to the second input of AND Gate 732. Since the inputs to AND Gate 732 are logic "1" and "0" values, the output signal 644 of AND Gate 732 has a logic "0" value. This logic "0" value is applied as the fourth input signal to NOR Gate 658 in FIG. 13.

The fifth signal input to NOR Gate 658 is the IRW signal, which as previously described, has a logic "0" value. Since, all of the inputs do not have a logic value of "0", the output of NOR Gate 658 is a logic "0" value, which is input as the second logic "0" value input to NOR Gate 662.

The third input to NOR Gate 662 is the output of NOR Gate 660. The first input to NOR Gate 660 is the previously described "0" logic value of the IRW signal. The second input is TRVD signal after it passes through inverter 656. The TRVD signal in State B1 has a logic "0" value except for that portion of the clock period before which B1 changes to B2, when TCB1 is a logic "1" value. TRVD signal 643 passes through inverter 656, and its compliment $\overline{TRVD}$, is provided as the second input. Since there is a logic "0" and a logic "1" value applied as inputs of NOR Gate 660, the output will be a logic "0" value. This logic "0" value output is input as the third logic "0" value input to NOR Gate 662.

The fourth input to NOR Gate 662 is signal 447, output from AND Gate 744 (FIG. 14). The output of AND Gate 744 is determined by the output of NOR Gate 784, inverter 742 and the R/S (reset/set) latch formed by NOR Gates 736 and 738. A complete description of the operation of the R/S latch will follow when discussing the DDI modality logic circuitry. In the DDX modality, $\overline{DDI}$ signal 346 having a logic "1" value is processed by inverter 730. The DDI signal having a logic "0" value output from the inverter 730 is input to NOR Gate 738. This logic "1" value $\overline{DDI}$ signal will hold the latch reset and the output of the latch will be a logic "0" value, which is input to inverter 742. The compliment of the input is output from inverter 742, so a logic "1" value is input to AND Gate 744 for the entire time the DDX modality is programmed.

The second input to AND Gate 744 is TRAD signal 646 which is output from NOR Gate 784. As previously described it has a logic "0" value. Since the inputs to AND Gate 744 are a logic "0" and a logic "1" value, the output signal 447 having a logic "0" value is input as the fourth input to NOR Gate 662.

Referring to FIG. 13, since all of the inputs to NOR Gate 662 are logic "0" values, the output is a logic "1" value. This logic "1" value is input to the D input of flip-flop 664. On the positive edge of $\overline{CK1}$ signal 167, the SB0 signal will have a logic "1" value. This is indicative of the logic value of the SB0 signal in State B1.

Referring to FIG. 13, now a description of the SB1 signal for State B1 will follow. In State B1, the SB1 signal will have a logic "0" value. This will be true if the $\overline{Q}$ output of flip-flop 676, is a logic "0" value. In order for the $\overline{Q}$ output to have a logic "0" value, the logic value input to the D input of flip flop 676 must have a logic "1" value prior to the positive edge of $\overline{CK1}$ signal 167. The Gates which determine the logic value loaded into the D input of flip-flop 676 are NOR Gate 670 and NOR Gate 672. These logic Gates form a clocked set/reset latch for the SB1 State signal.

There are three inputs to NOR Gate 670. The first input is the feedback signal from the Q output of flip-flop 676. This logic value in State B1 is "1" and so a logic "1" value is fed back as a first input. The second input is the TRAD signal 646, which has a logic "0" value, as previously described. The third input is $\overline{DDI} \cdot TCA1 \cdot (PVER+TCB2+TCB3)$ signal 644 which has a logic "0" value as previously described.

Since all of the inputs to NOR Gate 670 do not have a logic "0" value, the output is a logic "0" value. This logic value is input to NOR Gate 672 as a first input. The second input to NOR Gate 672 is the IRW+TRVD signal, which as previously described has a logic "0" value. Since both logic value inputs to NOR Gate 672 are "0", the output logic "1" value, which is input to the D input of flip-flop 676. This results in a logic "0" value output at the $\overline{Q}$ output on a positive clock edge of $\overline{CK1}$ signal 167.

The SB0 signal having a logic "1" value and the SB1 signal having a logic "0" value are input to NOR Gate 666. The output of NOR Gate 666 is a logic "0" value. This value is input to NOR Gate 232 as the third input (FIG. 8A).

Referring to FIGS. 8A and B, the fourth input to NOR Gate 232 is the output of a NAND Gate 234. The first input to NAND Gate is $\overline{C1}$ signal 340 generated in FIG. 12, which will be described subsequently. Since the apparatus is in State B1, the C timer state is C0 as previously set forth. Therefore, $\overline{C1}$ signal 340 has a logic "1" value. When CK1 signal 161 is a logic "0" value, the output of Gate 234 is a logic "0" value which is input to NOR Gate 232 as the fourth input.

Since all four inputs to NOR Gate 232 have a logic "0" value, the output is a logic "1" value.

Now having described what causes a logic "1" value output of NOR Gate 232, the remainder of the logic causing a logic "1" value IRW will be described.

Referring to FIG. 9A, the logic "1" value output from NOR Gate 232 (Signal 336) is input to AND Gate 424 as the second input. As previously described, the other input to AND Gate 424 is the logic "1" value output from MUX 408. Since both inputs to AND Gate 424 are logic "1" values, the output will be a logic "1" value, which is input to NOR Gate 428 as the second input.

The first input to NOR Gate 428 is the feedback from the output of NOR Gate 430. The two Gates, NOR Gate 428 and NOR Gate 430 form an R/S latch. The logic value fed back, as an input to NOR Gate 428, is a logic "0" value, since we have assumed no prior R-waves in this duty cycle and there is no noise on the R channel. The output of NOR Gate 428 is a logic "0" value. This logic "0" value is input to NOR Gate 430 as the first input. The second input to NOR Gate 430 is the output of NOR Gate 426.

NOR Gate 426 has two inputs, which are tied. The output signal of NOR Gate 232 is input to the tied inputs of NOR Gate 426. Since the logic value output from NOR Gate 232 has a logic "1" value when CK1 is logic "0" value, the output logic value of NOR Gate 426 is a logic "0" value, which is input to NOR Gate 430 as the second input. Both inputs to NOR Gate 430 have logic "0" values, so, the output of NOR Gate 430 is a logic "1" value. This logic "1" value is input to the D input to flip-flop 432. On a positive edge of CK1 signal 161 the $\overline{Q}$ output of flip-flop 432 will assume a logic "0" value. This logic "0" value is input to NAND Gate 434 as the first input.

The second input to NAND Gate 434 is the output of NOR Gate 194, (FIG. 8A) which has a logic "1" value, since both inputs to NOR Gate 194 have logic "0" values. Since one of the inputs to NAND Gate 434 has a logic "0" value, the output is a logic "1" value. This value is input to the tied inputs of NAND Gate 436. This output of NAND Gate 434 is also SRW signal 460.

The logic "1" value inputs cause a logic "0" value output from NAND Gate 436. This output is input to OR Gate 438 as a second input.

The first input to OR Gate 438 is the SA1 signal 450. As stated the A timer is in State A0 and no noise is present on the R channel. Therefore, SA1 will have a logic "0" value, which is input to OR Gate 438. The third signal input is C2 signal 462 output from NOR Gate 578. As stated, the C timer is in State C0 during State B1, therefore, the C2 signal will have a logic "0" value. Since all of the inputs have a logic "0" value, the output of OR Gate 438 is a logic "0" value.

The logic "0" value output for OR Gate 438 is input to NAND Gate 440 as the first signal input. The second signal input is the logic "1" value, which was output of NOR Gate 194, as previously described. Since the inputs to NAND Gate 440 are logic "0" and "1" values, it will result in IRW signal 464 having a logic "1" value.

Now having described the IRW signal, generation of the TRVD signal with a logic "1" value will be described. This is the second signal which can clock QUAD latch 238. Referring to FIG. 14, TRVD signal 807 is the output of NAND Gate 766.

When there is an IRW signal with a logic "1" value, TRVD signal 807 will have a logic "0" value. The reason for this is that an IRW will inhibit a TRVD which results in pacer-generated pulses unless the apparatus is the pacing modalities of AAT or VVT. Therefore, it will be assumed that the IRW signal has a logic "0" value so that the generation of a logic "1" value TRVD signal can be described. For example purposes, it is assumed that the B timer is in State B1; the A timer is in State A0 and the C timer is in State C0. Therefore, the following is a description of the logic circuitry which will generate a logic "1" value TRVD signal in the presence of a logic "0" value IRW signal.

Referring to FIG. 14, the first input to NAND Gate 766 is the output of NAND Gate 748. NAND Gate 748 has three inputs. The first input to NAND Gate 748 is the output of NAND Gate 586. The inputs to NAND Gate 586 are VDD+DDD signal 333 having a logic "1" value and $\overline{C0}$ signal 634. C0 signal has a logic "1" value since it has been assumed that the C timer is in State C0. The C0 signal passes through inverter 588, so, $\overline{C0}$ signal 634 having a logic "0" value is provided as the first input to NAND Gate 586.

The two inputs to NAND Gate 586 are a logic "1" and logic "0" value, so, the output is a logic "1" value. This logic "1" value is the first input to NAND Gate 748.

The second signal input to the NAND Gate 748 is the output of NOR Gate 740. The two inputs are tied and are connected to the IRW signal 464. Since the IRW is a logic "0" value, the output of NOR Gate 740 will have a logic "1" value, which is input as the second input NAND Gate 748.

The third input to NAND Gate 748 is the $\overline{Q}$ output of flip-flop 750. Flip-flop 750 and NAND Gates 752 and 754 form a clocked latch. This latch is necessary in case there is an early P-wave in the cycle. Under these conditions, the C timer is in State C0 at that time. It is only after the time out of State C3 that C0 can be reached. This prevents generation of a ventricular pulse faster than the maximum track rate.

NAND Gate 754 receives two inputs. The first is the $\overline{TCB1}$ signal, which as previously described, has a logic "1" value before TCB1 is reached.

In State B0, which precedes State B1, B1 signal 446 has a logic "0" value. In B0 because of inverter 770, $\overline{B1}$ signal is a logic "1" value and input to the set input of flip-flop 750 causing the Q output to assume a logic "1" value and the $\overline{Q}$ output to assume a logic "0" value. Once the new State B1 begins, the latch formed by flip-flop 750; NAND Gates 752 and 754 remains set. It is only at the changing of set term $\overline{TCB1}$ signal 642 for the latch that the latch will be reset. Therefore, in State B1, the feedback signal will be a logic "1" value. So, the output of NAND Gate 754 is a logic "0" value, which is input to the tied signal inputs of NAND Gate 752. Since both inputs to NAND Gate 752 have logic "0" values, the output is a logic "1" value. This logic "1" value is input to the D input to flip-flop 753 and on a positive clock edge of $\overline{CK1}$ signal 167, the Q output will have a logic "1" value and the $\overline{Q}$ output will have a logic "0" value. The $\overline{Q}$ output is input as the third input to NAND Gate 748. Therefore, since all of the inputs to NAND Gate 748 are not a logic "1" value, the output of this Gate is a logic "1" value, which is the first input to NAND Gate 766.

In order to produce a TRVD signal with a logic "1" value, the B timer must precede to a terminal count on State B1, as shown in timing diagram 86 in FIG. 7. Therefore, it must be assumed that TCB1 has been reached if there is to be a TRVD signal with a logic "1" value. When this takes place, the inputs to NAND Gate 754 will be the logic "1" value for the feedback from the Q output of flip-flop 750 and the logic "0" value of $\overline{TCB1}$ signal 642. The output of NAND Gate 754 is a logic "1" value which is input to the tied inputs of NAND Gate 752. Since the inputs to NAND Gate 752 are logic "1" values, the output is a logic "0" value, which is input to the D input of flip-flop 750. On the next positive clock edge of $\overline{CK1}$ signal 167, the Q output of flip-flop 750 will assume a logic "0" value and the $\overline{Q}$ output of logic "1" value. The $\overline{Q}$ logic value is input to NAND Gate 748 as the third input. Since all of the inputs to NAND Gate 748 are logic "1" values, the output is a logic "0" value, which is input to NAND Gate 766 as the first input.

The second input to NAND Gate 766 is the output of NAND Gate 746. The signals input to NAND Gate 746 are AAT+VVT signal 354 and IRW signal 464. Since the DDX modality is not one of the triggered modalities, the logic value of AAT+VVT signal 354 is a logic "0" value. The IRW signal, as described, has a logic "0" value. Therefore, the output of NAND Gate 746 is a logic "1" value, which is input as the second input to NAND Gate 766.

The third input to NAND Gate 766 is $\overline{TRIG}$ signal 330. As previously described, the logic value of the $\overline{TRIG}$ signal is a logic "1" value.

The fourth input to NAND Gate 766 is the output of OR Gate 764. The first input is the output of NOR Gate 762, which as described, has a logic "0" value. The second input is the IRW signal which as described has a logic "0" value. The third signal is DDD+DVI+-DOO+DDI+DDX signal 352, which as described for the DDX modality, has a logic "1" value. Since at least one of the inputs to OR Gate 764 has a logic "1" value, the output is a logic "1" value.

All of the inputs to NAND Gate 766 do not have a logic "1" value, so, the output is a logic "1" value, which is TRVD signal 807.

IRW signal 464 and TRVD signal 807 can input to OR Gate 654 (FIG. 13). The output of that gate is IRW+TRVD signal 572. Now having described the generation of an IRW signal or TRVD signal having a logic "1" value, the description will disclose the method in which IRW+TRVD signal 572 having a logic "1" value will cause clocking of QUAD latch 238.

Referring to FIG. 12, IRW+TRVD signal 572 having a logic "1" value is input to the D input of flip-flop 608. On the next positive clock edge of $\overline{CK1}$ signal 167, the Q output will assume a logic "1" value, which is input to the D input of flip-flop 610. On the following positive clock edge of $\overline{CK1}$ signal 167, the logic "1" value input to the D input of flip flop 610 will be output from the Q output to clock the quad latch 238. This clocking of quad latch 238 is present when either TRVD signal 807 or IRW signal 464 has a logic "1" value. However, clocking of flip-flop 795 in FIG. 14, for creating a logic "1" value for FRDVI signal 44, takes place only when IRW signal 464 changes from a logic "0" to a logic "1" value and the apparatus is in State B2 or B3.

Flip-flop 608, besides being used for providing the clocking signal for Quad latch 238, has its $\overline{Q}$ output used as one of the signals for generating CRST signal 624 for resetting the C timer.

Referring to FIG. 12, when the D input to flip-flop 608 has a logic "1" value, the $\overline{Q}$ output will assume a logic "0" value output that is input to NOR Gate 614. The second input to NOR Gate 614 is CK2 signal 163. On the negative edge of CK2, the output of NOR Gate 614 will have a logic "1" value output for resetting the C timer.

Now having disclosed the clocking of the flip-flop 795 for producing FRDVI signal 444 having a logic "1" value, the effect of this signal will be described on other portions of the logic circuitry.

Referring to FIG. 14, the FRDVI signal 444 value can only be a logic "1" value when an R-wave resulting in an IRW is sensed before a P-wave during State B2 or B3. FRDVI signal 444 cannot have a logic "1" value during State B0 and B1. During States B0 and B1, $\overline{SB1}$ signal 724 is input to the set input to flip-flop 795. This signal has a logic "1" value in States B0 and B1. This logic "1" value input will hold the $\overline{Q}$ output of flip-flop 795 which is FRDVI signal 444 at a logic "0" value. It is only during State B2 and B3, when $\overline{SB1}$ signal 724 is a logic "0" value that there will be clocking of the D input value in the event of a clocking IRW pulse.

If there is a sensed R-wave (SRW) during State B2 or B3 and the C timer is not in State C2 and the A timer is not in State A2, the SRW signal 460 will result in an IRW signal. This IRW signal is indicative of premature activity. This IRW signal will clock the flip-flop 795 and the stimulator will pace in the DVI modality until flip-flop 795 is forced set by States B0 or B1. At this time the stimulator will again pace in the DDD modality or the atrial refractory period will be extended as will be described in the second embodiment of the invention.

Referring to FIG. 9A, once FRDVI signal 444 having a logic "1" value is output from flip-flop 795 (FIG. 14), it is input to OR Gate 396. The output of OR Gate 396 will have a logic "1" value output regardless of the logic value of the other inputs. The output of OR Gate 396 is input to NOR Gate 400 as a first input.

Since the output logic value of OR Gate 396 is a logic "1" value, the output of NOR Gate 400 will be a logic "0" value. This logic "0" value is input to two gates. It is input to AND Gate 404, as a first input, and inverter 402. This logic "0" value output from NOR Gate 400, after being processed by inverter 402, is a logic "1" value and input to NOR Gate 416 as the first input. The output of NOR Gate 416 is input to the D input of flip-flop 418. As long as a logic "1" value is input to NOR Gate 416, its output will remain a logic "0" value. This means that a logic "0" value is input to the D input of flip-flop 418 and, upon clocking of the flip-flop, the Q output, which is SPW signal 456, will be a logic "0" value. This will mean that any P-wave sensed while in the forced DVI modality will not be acted upon by the apparatus. The apparatus will remain this way for the next beat until the FRDVI signal having a logic "1" value is cleared out upon reaching B timer State B0 or B1.

Referring to FIGS. 9A, 9B, 21A and 21B, a second embodiment of DDX is shown. In this second embodiment, when FRDVI signal 444 has a logic "1" value, it will cause an extension of the atrial refractory period. This will prevent sensing of any retrograde activity from a ventricular depolarization.

Figure 21B:
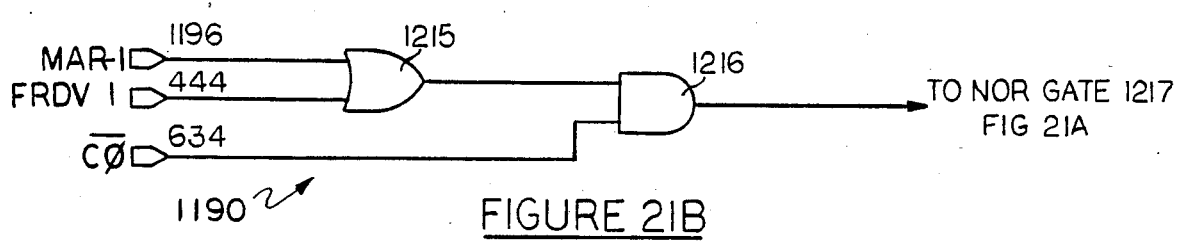
FIG. 21B shows a secondary embodiment for input of the FRDVI signal in the DDX modality for extension of the atrial refractory period.

In this second embodiment, in FIG. 9B, the inputs to OR Gate 396 are ATREF signal 376 and B1 signal 446. FRDVI signal 444 is no longer input to OR Gate 396 but is input as shown in FIG. 21B.

FRDVI signal 444 along with MAR-1 signal 1196 are input to OR Gate 1215. MAR-1 signal 1196 is the MSB for the set of bits programmed in memory for controlling the atrial refractory period. Therefore, when FRDVI signal 444 has a logic "1" value, it will act as the MSB (most significant bit) for atrial refractory and will cause an extension of atrial refractory until the FRDVI signal is cleared out, unless there has been programming of a long atrial refractory period which would moot the FRDVI signal's effect. So, when the apparatus experiences a premature activity, the apparatus will not change modalities from DDD to DVI, but will extend the atrial refractory period so that any depolarization in the atrium during the period of atrial refractory will have no affect on pacer operations.

DDI OPERATION

The DDI modality as stated is somewhat identical to the DVI modality except that instead of sensing only in the ventricle, it senses activity in the atrium as well. However, when the apparatus detects a natural atrial pulse, it does not synchronize off of it to stimulate the ventricle. The ventricular side of the stimulator works like the DVI modality normally does, and resets timing as well as inhibiting either of the two stimuli if an R-wave is sensed.

Referring to FIGS. 8A through 21, a description of the logic circuitry for the DDI modality will follow.

Referring to FIG. 8A generally shown at 160, for the DDI modality, the mode section of memory is programmed such that the M-MODE 0 signal, input at 172, has a logic "1" value; the M-MODE 1 signal, input at 174, has a logic "0" value; the M-MODE 2 signal, input at 176, has a logic "1" value; and the M-MODE 3 signal, input at 178, has a logic "1" value.

When the M-MODE 0-3 inputs have the above described logic value, quad latch 238 has inputs such that $D_0$ input 242 has a logic "1" value; $D_1$ input 244 has a logic "0" value; $D_2$ input 246 is loaded at a logic "0" value; and the $D_3$ input 248 has a logic "1" value.

Referring to FIG. 8B, when the DDI modality is programmed, DDI signal 346, output by NOR Gate 272, has a logic "1" value. NOR Gate 272 has two inputs. The first is the $\overline{M2}$ signal output from the $Q_2$ output 258 of latch 238. As described, the logic value input at the $D_2$ input 246 is a logic "0" value. When this latch value is clocked, the $\overline{M2}$ signal has a logic "0" value which is input to NOR Gate 272.

The second input to NOR Gate 272 is the output of OR Gate 270. The first input to OR Gate 270, is the output of NAND Gate 306. NAND Gate 306 has two inputs. The first input is the logic "1" value of the M0 signal output from the $Q_0$ output 250 of quad latch 238. The second input to NAND Gate 306 is DUAL signal 350. DUAL signal 350, which is the M3 output of QUAD latch 238, has a logic "1" value for the DDI modality as described. Since both inputs to NAND Gate 306 have logic "1" values, the output of that Gate is a logic "0" value, which is input, as a first input to OR Gate 270. The second input to OR Gate 220 is M1 signal having a logic "0" value. Both inputs to OR Gate 270 are a logic "0" value, so the output will be a logic "0" value. This logic "0" value output is input to NOR Gate 272.

Both inputs to NOR Gate 272 have logic "0" values, therefore, the output will be a logic "1" value indicative of the DDI modality being programmed.

Referring to FIG. 14, the DDI signal with a logic "1" value is input to AND Gate 732 after passing through inverter 730, therefore, the signal input to AND Gate 732 is $\overline{DDI}$ having a logic "0" value. The second input to AND Gate 732 is TCA1 (PVER+TCB2+TCB3) signal 504.

Since $\overline{DDI}$ has a logic "0" value, the output of AND Gate 732 will always be a logic "0" regardless of the logic value of TCA1 (PVER+TCB2+TCB3) signal 534. Therefore, the R channel is not responsive to P-wave events.

For purposes of example in describing the logic circuitry associated with the DDI modality, the B timer will be assumed to be in State B2 for generation of a TRA signal having a logic "1" value and State B1 for generation of a TRV signal having a logic "1" value. The states of the C timer will not be in C1 for generation of either a TRA or a TRV. The state of the A timer will be as described in the text for generation of either a TRA or TRV signal having a logic "1" value.

Referring to FIG. 13, the output from AND Gate 732, which is $\overline{DDI}$. TCA1 (PVER+TCB2+TCB3) signal 644, is input to a clocked set/reset latch comprised of NOR Gate 658, NOR Gate 660, NOR Gate 662 and flip-flop 664, as a set term. Since the output of AND Gate 732 is always a logic "0" value in the DDI modality, this latch will never be set by this term to change the B timer state, and the latch formed by NOR Gate 670, NOR Gate 672 and flip-flop 676; and NOR Gate 674.

The manner in which a TRA signal having a logic "1" value is produced will be described in the following text.

Referring to FIG. 14. when the output of flip-flop 788 (the TRA signal) has a logic "1" value, an atrial pulse will be output from the apparatus.

The logic gates used that produce a TRA signal in the DDI modality, which can later result in an apparatus generated atrial pulse, are NOR Gate 736, NOR Gate 738, inverter 742, AND Gate 744 and NOR Gate 784.

Figure 11:
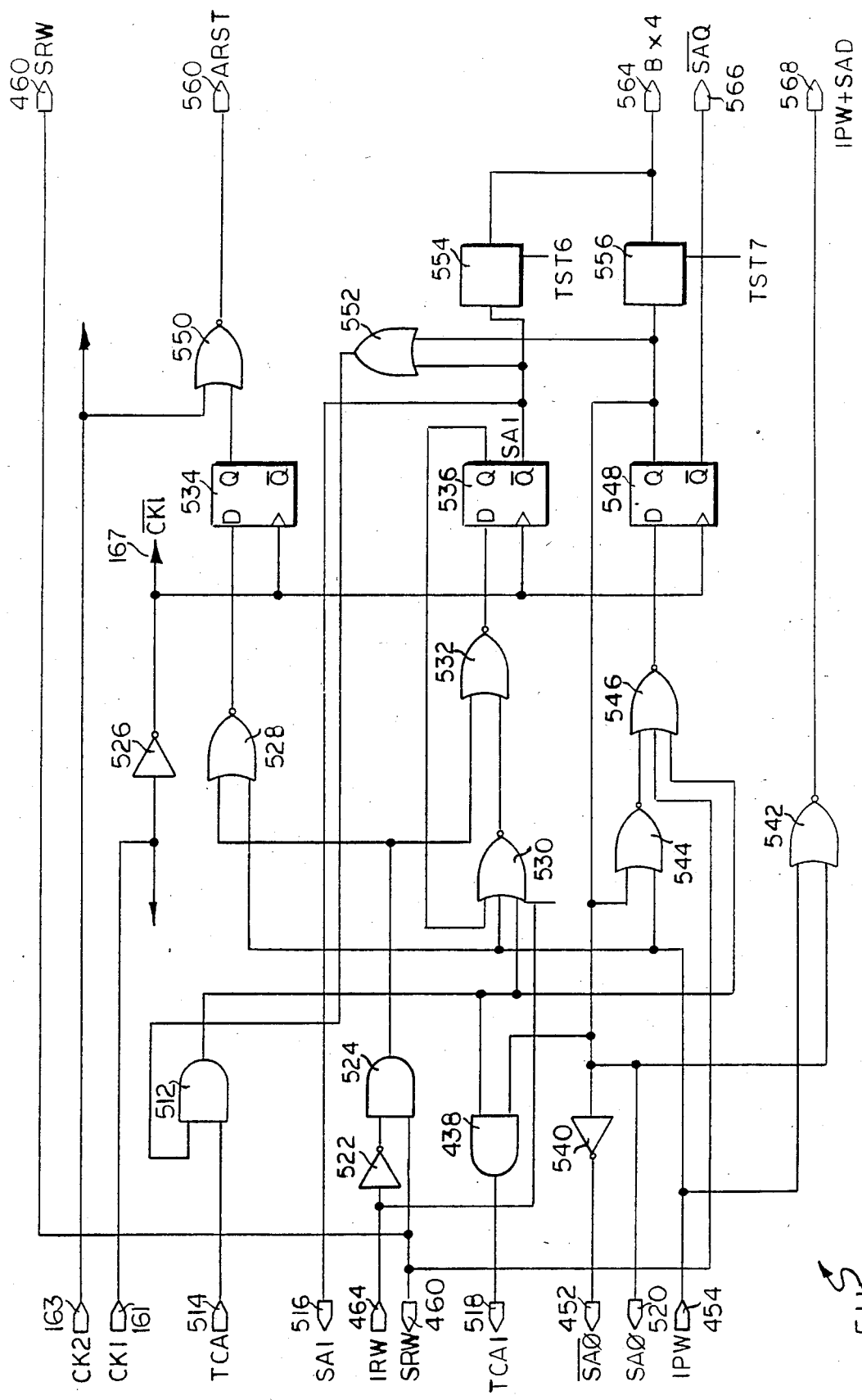
FIG. 11 shows the A-timer section of the pulse generator logic.

As previously described, when the DDI modality is programmed, DDI signal 346 has a logic "1" value. This logic value is input to inverter 730 and its compliment, a logic "0" value, is provided as an output. This logic value is input to NOR Gate 738, as a first reset term, for the set/reset latch formed by NOR Gates 736 and 738. The second reset term is the SBP signal 502. The third reset term to NOR Gate 738 is C1 signal 575. The C1 signal indicates that C-timer State C1 is operative, which is representative of both atrial and ventricular absolute refractory. The set term for the set/reset latch is SA0 signal 520, which is output from flip-flop 548 (FIG. 11). This set signal is input to NOR Gate 736.

When the latch is set, the output of NOR Gate 738 is a logic "1" value, which is input to NOR Gate 736. The other input to NOR Gate 736 is SA0 signal 520. When there is a P-wave sensed and the A timer enters State A1, SA0 signal 520 will change from a logic "0" value to a logic "1" value causing the output of NOR Gate 736 to assume a logic "0" value. This logic "0" value is input to NOR Gate 738 as the first input.

When the other three inputs to NOR Gate 738 have logic "0" values, the latch will be set and the input to AND Gate 744 will be a logic "0" value, since the logic "1" value output from NOR Gate 738 passes through inverter 742 before it is input into AND Gate 744. Assuming this condition remains, the output of AND Gate 744 will always be a logic "0" value regardless of the logic value of the other input. Therefore, a TRA will be inhibited under these conditions.

As previously described, the reset terms for the latch comprised of NOR Gate 736 and 738 are C1 signal 575, SBP signal 502 and the $\overline{DDI}$ signal. Any of these signals having a logic "1" value will reset the latch to allow generation of a TRA signal having a logic "1" value when the output of NOR Gate 784 has a logic "1" value.

The principal signal for resetting the latch is C1 signal 578. This signal will reset the latch every cycle when State C1 is initiated simultaneously with the beginning of State B2 or B3. It is only upon a blocked P state, when SBP signal 502 has a logic "1" value, that the latch will be reset. This will only take place when there is atrial activity sensed at the P-wave sensor is determined to be noise.

The following is a description of how C1 signal 578 resets the latch after a TRV or IRW signal having a logic "1" value. Following this disclosure, the SBP signal reset of the latch will be disclosed.

When TRV signal 816 has a logic "1" value or the IRW signal has a logic "1" value, and State B2 or B3 is initiated, State C1 is initiated. The A timer is in State A0 at this point, so, SA0 signal 520 has a logic "0" value which is input to NOR Gate 736. The C1 signal having a logic "1" value is input to NOR Gate 738 and causes the output of that gate to assume a logic "0" value; regardless of the logic value of other inputs. This logic "0" value is fed back as the second input to NOR Gate 736 causing it to have a logic "1" output which is input to NOR Gate 738 to hold the latch reset.

The logic "0" value output from NOR Gate 738 is input to inverter 742 and its compliment is output from the inverter. This logic "1" value of inverter 742 is input to AND Gate 744 as the first input. Therefore, C1 signal 575 will reset the latch after every ventricular event whether it is an IRW or a TRV.

The SBP signal will be used to reset the latch only during State B2 or B3, when activity is sensed at the P-wave sensor. If a PVER signal has a logic "1" value, at TCA1, SBP signal 502 will have a logic "0" value and the latch will not be reset by the SBP signal. However, when the P-wave verification test is failed during State B2 or B3 while the A timer is in State A1, SBP signal 502 will reset the latch. Upon such sensing on the P channel, SA0 signal 520, which is input to NOR Gate 736 and has an effect only after C1 has a logic "0" value. If the A timer times out of A1 and results in a valid P-wave, the logic value of SA0 will change from a logic "1" to a logic "0" value, but the output of NOR Gate 736 will remain a logic "0" value if SBP signal 502 remains a logic "0" value.

However, if the A timer times out of State A1 and does not result in a verified P-wave, but results in SBP signal 502 having a logic "1" value, indicating failure of the P-wave noise test, the output of NOR Gate 738 will change from a logic "1" value to a logic "0" value. This logic "0" value is input to inverter 742 which changes the logic "0" value to its compliment, a logic "1" value, which is input to AND Gate 744. This will also cause the output of NOR Gate 736 to have a logic "1" value which will hold the latch reset.

The following will describe the generation of logic "1" value output to NOR Gate 784, which is the second input to AND Gate 744.

The first input to NOR Gate 784 is DDD+DVI+DOO+DDI+DDX signal 352 which has a logic "1" value in the DDI modality. However, signal 352 is passed through inverter 780 before being input to NOR Gate 784, so the input logic value is a logic "0" value.

The second input to NOR Gate 784 is the output of NOR Gate 762. The output of NOR Gate 762 is derived from AND Gate 758, OR Gate 756 and AND Gate 760. The first input to AND Gate 758 is the output of NAND Gate 728. The first input to NAND Gate 728 is IPW+SA0 signal 568, output from OR Gate 542 (FIG. 11).

Referring to FIG. 11, the inputs to OR Gate 542 are SA0 signal 520 and IPW signal 454. SA0 signal 520 is output from the Q output of flip-flop 548. This signal is input as a first input to OR Gate 542. SA0 signal 520 has a logic "0" value, since it is assumed SBP signal 448 has a logic "1" value. SBP signal 448 can have a logic "1" value when the A timer is not in A1.

The second signal input to OR Gate 542 is IPW signal 454, which will have a logic "0" value when SBP signal 448 has a logic "1" value. Thereafter, the second input to OR Gate 542 is a logic "0" value. Since both inputs to OR Gate 592 are logic "0" values, the output is a logic "0" value. So, the first input to NOR Gate 728 is a logic "0" value. The other input inputs to NAND Gate 728 are tied together. This input is the $\overline{DDI}$ signal. In the DDI modality, the logic value of the inputs is a logic "0" value. Therefore, the output of NAND Gate 728 is a logic "1" value regardless of the logic value of the other input IPW+SA0 signal 568.

NAND Gate 728 is applicable only in the DDX, VDD, and DDD modalities. If the apparatus is in State A1 for the P-wave noise test and there is a time out of TCB2 or TCB3, the apparatus will be inhibited from producing an atrial pulse. This is because the output of AND Gate 758 will have a logic "0" value which will cause the output of NOR Gate 762 to assume a logic "1" value, since AND Gate 760 will have a logic "0" value if such conditions exist. This logic "1" value will be input to NOR Gate 784 causing it to have a logic "0" value output, which is input to AND Gate 744. Because of this logic "0" value input, AND Gate 744 will have a logic "0" value output which is input to the D input of flip-flop 788 and the TRA signal will have a logic "0" value, indicative of an inhibited atrial pulse.

Again referring to NAND Gate 728, the inputs have at least one logic "0" value because of the $\overline{DDI}$ signal, so the output of NAND Gate 728 is a logic "1" value, which is input to AND Gate 758 as a first input. The second input to AND Gate 758 is TCB2+TCB3 signal 472. The logic value of the signal during but prior to time out of State B2 or B3 is a logic "0" value. So the output of AND Gate 758 is a logic "0" value, which is the first input to NOR Gate 762. However, once there is a time out of State B2 or B3 the logic value of the TCB2 or TCB3 signal 472 changes from a logic "0" value to a logic "1" value which will cause the output of AND Gate 758 to change from a logic "0" to a logic "1" value. This value is input to NOR Gate 762 and causes its output to change from a logic "1" value to a logic "0" value. This logic "0" value is input to NOR Gate 784 as the second input.

Before proceeding further with the disclosure regarding the inputs to NOR Gate 784, it is noted that IPW signal 454 has been discussed briefly as an input to OR Gate 542. This signal requires a detailed explanation and will be disclosed in the following text.

Referring to FIG. 9A, IPW signal 454 is generated from the output of AND Gate 420. The first input to AND Gate 420 is $\overline{SA0}$ signal 452. The logic value of this signal is generated from the A timer State flip-flop 548 (FIG. 11). $\overline{SA0}$ signal 452 has a logic "1" value in State A0 or A2. However, it is only during States A0 that an IPW signal having a logic "1" value can be generated. This logic "1" value is input to AND Gate 420 as a first input and enables a logic "1" value IPW when SPW signal 546 has a logic "1" value. This logic circuitry also prevents an IPW signal 454 from having a logic "1" value in State A1.

The second signal input to AND Gate 420 is SPW signal 456 whose logic value is determined by the output of flip-flop 418, NOR Gate 416, OR Gate 396, NOR Gate 414, inverter 402, AND Gate 404, AND Gate 412 and NOR Gate 400. Of the above addressed gates, NOR Gates 414 and 416 form an asynchronous latch.

When there is a depolarization in the atrium or activity sensed by the P channel sensor, $\overline{AET}$/ 380 will have a logic "0" value, otherwise it will assume a logic "1" value. Assuming that there was detection of activity by the P-channel sensor, logic "0" value is input to inverter 381. A logic "1" value is output from the inverter and input to transmission gate 390. The control signal TST 7, as previously described, after passing through inverter 386 provides a logic "1" value to transmission Gate 390. This logic "1" value turns Gate 390 on and the output of transmission Gate 390 is a logic "1" value which is input to AND Gate 404 as the first input. The second input to AND Gate 404, is output of NOR Gate 400, which has a logic "1" value. If this were not the case, the latch comprised of NOR Gates 414 and 416, would be held reset disabling the generation of an IPW signal having a logic "1" value.

Since both inputs to AND Gate 404 are a logic "1" value, the output is a logic "1" value, which is input to AND Gate 412 as a first input.

The second input to AND Gate 412 is output signal 344 from OR Gate 228 (FIG. 8A). The first input to that gate is DDI signal 346 which has a logic "1" value. The second input is VDD+DDD+DDI+DDX signal which has a logic "1" value as described. Since at least one signal input to OR Gate 228 has a logic "1" value, the output is a logic "1" value.

The third input to AND Gate 412 is output signal 336, output from NOR Gate 232 (FIG. 8A). This output will have a logic "1" value when the conditions as previously described for the DDX modality exist. It is therefore when such conditions exist, signal 336 has a logic "1" value. Since all of the inputs to AND Gate 412 have logic "1" values, the output of that gate is a logic "1" value, which is input to NOR Gate 414 as a second input.

The first input to NOR Gate 414 is the output of NOR Gate 416 which is fed back to NOR Gate 414. This feedback signal will have a logic "0" value if there was no other P-waves or noise sensed on the P-channel. Therefore, it is assumed that this is the first activity sensed on the P-channel so the feedback signal has a logic "0" value. Since at least one signal input to NOR Gate 414 has a logic "1" value the output of NOR Gate 414 is a logic "0" value which is input to NOR Gate 416 as the third input.

The first input to NOR Gate 416 is the output of inverter 402 which has a logic "0" value as previously described. The second input to NOR Gate 416 is SA1 signal 450. Unless there is an R-wave noise test, the logic value of SA1 is a logic "0" value. It is only when premature noise is sensed on the R channel that SA1 signal assumes a logic "1" value, indicative of State A2. Therefore, SA1 is a logic "0" value.

The fourth input to NOR Gate 416 is the output of NOR Gate 426. The inputs to this gate are tied. The input signal to the tied inputs is the output signal from NOR Gate 232 (FIG. 8A) which signal 336. Since the output Gate 232 is a logic "1" value, the output by NOR Gate 426 is a logic "0" value.

Since all of the inputs to NOR Gate 416 are logic "0" values, the output is a logic "1" value which is input to the D input of flip-flop 418. On the next positive edge of CK1 signal 161 a logic "1" value is output from the Q output, which is SPW signal 456, and a logic "0" value from the $\overline{Q}$ output, which is $\overline{SPW}$ signal 458.

During every clock period when the apparatus is not in State B0 or C1, or asynchronously pacing; or in DOO, AOO or VOO modalities, the output of NOR Gate 232 will assume a logic "0" output for a portion of the clock period because of the changing of the logic value of the output of NAND Gate 234. This will take place in the beginning of each clock period on the edge of $\overline{CK1}$ signal 167. During this period, when the logic value of the output of NOR Gate 232 is a logic "0" value, the output of AND Gate 412 will be forced to a logic "0" value. Additionally the output of NOR Gate 232 is input to the tied inputs of NOR Gate 426, the output of NOR Gate 426 will change from a logic "0"

value to a logic "1" value. This logic "1" value is input to NOR Gate 416, resetting the asynchronous latch formed by NOR Gates 414 and 416.

Once this period has passed and the output of NAND Gate 232 returns to a logic "0" value, the output of NOR Gate 232 will assume a logic "1" value. If this situation exists and there is sensing of P-waves or noise during the sample period of A1, for the remainder of the clock period, the output of AND Gate 412 will again assume a logic "1" value which is input to NOR Gate 414 as the second input. Since the latch was reset by the outputs of NOR Gates 232 and 426, the feedback signal from NOR Gate 416 is a logic "0" value which is the second input to NOR Gate 414.

The inputs to NOR Gate 414 are a logic "1" value and a logic "0" value, so the output of that gate is a logic "0" value which is input to NOR Gate 416. Since the other inputs to NOR Gate 416 are logic "0" values, the output of NOR Gate 416 is a logic "1" value which is input to the D input of flip-flop 418. On the positive edge of CK1 signal 161, the Q output will assume a logic "1" value and the Q̄ output will assume a logic "0" value.

However, if during the 101.6 ms. of State A1, the ADET signal drops off for an entire clock period of 6.35 ms. and has a logic "1" value, the latch will remain reset. When the latch was reset by the output of NOR Gate 232, the outputs of AND Gate 404 and 412 maintained logic "0" values. Also the output of NOR Gate 426 is a logic "0" value holding the latch reset. It is this signal that is important and dominant for controlling the output of the latch, not the same input to NOR Gate 414. On the next positive edge of CK1 signal 161, the Q output, SPW signal 450, assumes a logic "0" value and the Q̄ output, SPW signal 458, assumes a logic "1" value. This SPW signal 458 having a logic "1" value for a clock period during State A1 will generate a PVER signal, having a logic "1" value.

As described, at time out of State A1, the A timer initiates State A0, unless there is sensing of noise on the R channel which initiates State A2. However in either case SA0 signal 452 will have a logic "1" value. Since both inputs to AND Gate 420 are logic "1" values, the output of that gate is IPW signal 454 having a logic "1" value. The generation of an IPW signal can take place with the first sensing of activity on the P-channel during a duty cycle. After this the logic circuitry will not allow any further sensing on the P-channel.

Now having described the generation of a logic "1" value IPW signal, a resumption of the description of the generation of second signal input to NOR Gate 762 follows.

Referring to FIG. 14, AND Gate 760 provides the second input to NOR Gate 762. The inputs to AND Gate 760 are the output of OR Gate 756 and TCN signal 701. In the presence of noise on the P or R channel, and assuming TCN signal 701 has a logic "1" value, the output of NOR Gate 762 will assume a logic "0" value.

When SBP signal 562 has a logic "1" value or SA1 signal 56 has a logic "1" value, the output of OR Gate 756 will have a logic "1" value. When the programmed TCN period is reached during State B2 or B3, TCN signal 701 assumes a logic "1" value. Therefore, both inputs to AND Gate 760 are logic "1" values. The output of this gate is a logic "1" value, which is input to NOR Gate 762. This logic "1" value will cause the output of NOR Gate 762 to assume a logic "0" value, which is input as the second input to NOR Gate 784.

Both methods of causing a logic "0" value output from NOR Gate 762 have been described. Now the third input to NOR Gate 784 will be disclosed.

The third input to NOR Gate 784 is IRW signal 464. As stated, this signal normally has a logic "0" value in State B2 or B3. The output of NOR Gate 784 will be a logic "1" value, since all of the inputs are logic "0" values. This logic "1" value is input to AND Gate 744 as the second input.

Both inputs to AND Gate 744 have a logic "1" value, therefore the output will have a logic "1" value, which is input to the D input of flip-flop 788. On the next positive clock edge of CK1 signal 167, the logic "1" value input to the D input is output from the Q output of the flip-flop and is the TRA signal.

This TRA signal having a logic "1" value can generate TRA REQ signal 808 having a logic "1" value, which produces an apparatus generated atrial pulse. Referring to FIG. 14, the output of flip-flop 788 is input to NAND Gate 790 as a first input. The second input to NAND Gate 790 is the M3 signal 362. As previously described, the M3 signal has a logic "1" value in the DDI modality. Since both inputs to NAND Gate 790 have a logic "1" value, the output is a logic "0" value. This logic "0" value output is input to NAND Gate 774. Since there is at least one logic "0" value input to NAND Gate 774, the output is a logic "1" value. The logic "1" value output from NAND Gate 774 is TRA REQ signal 808. TRA REQ signal 808, having a logic "1" value, causes an atrial pulse to be output from the apparatus.

The production of a TRV in the DDI modality follows essentially the description as set forth for production of a TRVD in the DDX modality, except there are other operative logic Gates which act on the TRVD signal having a logic "1" value to produce TRV signal 816 which can result in TRVREQ signal 810 having a logic "1" value. These logic Gates are flip-flop 768, inverter 804, and NOR Gate 806.

Referring to FIG. 14, once TRVD signal 806, output from NAND Gate 766, has a logic "1"0 value, it is input to the D input of flip-flop 678. On the next positive edge of CK1 signal 167, the Q output of flip-flop 768 assumes a logic "1" value. This output, is input to inverter 804 and its compliment is provided as an output. So, a logic "0" value is input as a first input to NOR Gate 806.

The second input to NOR Gate 806 is the RXOVER signal 358. This signal has a logic "1" value when one of the atrial pacing modalities are programmed. The DDI modality is a dual chamber modality, so, RXOVER will have a logic "0" value. Since both inputs have a logic "0" value, the output is a logic "1" value which is TRV REQ signal 810, which will cause a ventricular output pulse from the stimulator.

P-WAVE VERIFICATION

The P-wave verification logic circuitry will be described in the following test. Although there has been reference to this logic circuitry in the prior disclosure, a specific and concise description of this P-wave verification circuitry will follow. For purposes of explanation, the B timer is in State B2, the C timer is not in State C1 and the A timer proceeds from State A0 to A1 and back to A0 during the P-wave verification process.

Referring to FIG. 10, the P-wave verification section of the apparatus is generally shown at 470. Once activity is sensed by P-wave sensor, the end result is passage or failure of the P-wave verification test. This is based on the duration of the signal detected by the P-wave sensor.

Referring to FIG. 9A, when there is a sensing of an atrial signal by the P-wave sensor, a logic "0" signal is processed through the logic circuitry as previously described resulting in SPW signal 456 and IPW signal 454 having a logic "1" value. Once this has taken place, it must be determined if what was sensed are a valid P-wave or noise.

As previously stated, once IPW signal 454 assumes a logic "1" value, it will cause the A timer section of the PGSL to change from State A0 to A1. State A1 is 101.6 ms. in duration. If SPW signal 456 drops off for at least one clock period, there is a valid P-wave. However, if SPW signal 456 does not drop off for at least one entire clock period during State A1, there is failure of the P-wave verification test resulting in SBP signal 448 having a logic "1" value.

Before describing the logic circuitry for P-wave verification shown in FIG. 10, the description of the method of changing states of the A timer from A0 to A1 in the presence of a logic "1" value IPW signal will be disclosed.

Referring to FIG. 11, NOR Gate 544, NOR Gate 546 and flip-flop 548 form a clocked latch. IPW signal 454 having a logic "1" value is input to NOR Gate 544, as a first input. The second input to NOR Gate 544 is the feedback from the Q output of flip-flop 548 which is SA0 signal 520. As described, SA0 signal 520 has a logic "0" value in State A0. When IPW signal 454 having a logic "1" value is input to NOR gate 544, the output of that gate is a logic "0" value. This logic "0" value is input to NOR Gate 546 as a first input. The second input to NOR Gate 546 is SRW signal 460. This signal has a logic "0" value, because, it is assumed that there are no SRW signals indicative of premature activity at this point in the duty cycle.

The third input to NOR Gate 546 is the output of AND Gate 512. The inputs to AND Gate 512 are TCA signal 514 and the output of OR Gate 552. The output logic value of OR Gate 552 in State A0 is a logic "0" value because both SA1 signal 516 and SA0 signal 520 have logic "0" values. So, the output of AND Gate 512 is a logic "0" value regardless of the logic value of TCA signal 514. However, the second signal is TCA signal 514 which has a logic "0" value. It is only after a time out of A timer States A1 or A2 that TCA signal 514 will have a logic "1" value.

Since all of the inputs to NOR Gate 546 are logic "0" values, the output is a logic "1" value, which is input to the D input of flip-flop 548. On the next positive clock edge of CK1 signal 167, the Q output of flip-flop 548 will assume a logic "1" value. This logic "1" value is SA0 signal 520. This logic "1" is fed back to NOR Gate 544 to hold the latch set until it is reset by a logic "1" value SRW signal 460 or TCA signal 514.

Again referring to FIG. 11, a description of the logic circuitry for SA1 signal 516 follows. IPW signal 454, having a logic "1" value, is input to NOR Gate 530 as a second input. The first input to that gate is the feedback from the Q output of flip-flop 536, which is the $\overline{SA1}$ signal. In State A0, SA1 has a logic "0" value, so $\overline{SA1}$ has a logic "1" value. This logic "1" value will cause a logic "0" output from NOR Gate 530. This logic "0" value is input to NOR Gate 532 as a first input. The second input to NOR Gate 532 is the output of AND Gate 524. One of the inputs to AND Gate 524 is the SRW signal 460 which, as previously described, has a logic "0" value. Since there is at least one logic "0" value input, the output of AND Gate 524 is a logic "0" value. Both inputs to NOR Gate 532 are logic "0" values, so its output is a logic "1" value, which is input to the D input of flip-flop 536. On the next positive edge of $\overline{CK1}$ signal 167, the $\overline{Q}$ output of flip-flop 536, which is $\overline{SA1}$ signal 516, will remain a logic "0" value.

Simultaneous with the initiation of State A1 by IPW signal 454, IPW signal 454 also causes resetting of the A timer. This is accomplished through NOR Gate 528, flip-flop 534 and NOR Gate 550.

Again referring to FIG. 11, IPW signal 454 having a logic "1" value is input to NOR Gate 528 as the first input. The second input to NOR Gate 528 is the output of AND Gate 524 which is a logic "0" value, as described. Since one of the inputs is a logic "1" value, the output of NOR Gate 528 is a logic "0" value, which is input to the D input of flip-flop 534. On the next positive clock edge of $\overline{CK1}$ signal 167, the Q output assumes a logic "0" value, which is input to NOR Gate 550 as the first input. The second input is CK2 signal 163. When CK2 signal 163 has a logic "0" value, both inputs will be logic "0" values, so the output is a logic "1" value, which is ARST signal 560 that resets the A timer generally shown in FIG. 15.

Figure 15:
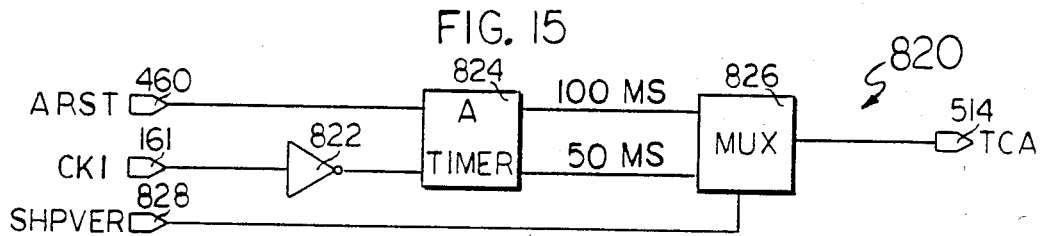
FIG. 15 shows the A-timer logic.

Referring to FIG. 15, the A timer is generally shown at 820 and consists of 15 bit binary counter 824 and MUX 826. The state logic of the A timer is shown in Table 3 above.

Binary counter 824 is designed to provide outputs every 8 clock periods or every 16 clock periods. Since each clock period is 6.35 ms, eight clock periods represents 50.8 ms., the shortened P-wave verification sample period, and 16 clock periods represent the normal P-wave verification sample period of 101.6 ms.

Control signal SHPVER 828 for the shortened P-wave verification period is output from the B counter and will be described subsequently. When the SHPVER signal 828 has a logic "1" value, the terminal count signal TCA will be associated with the 50.8 ms. output. When the SHPVER signal 828 has a logic "0" value, the terminal count signal TCA will be associated with the 101.6 ms. output.

Assuming normal operation, the TCA signal 514 will have a logic "1" value at the time out of State A1. This assumption will be used in describing the P-wave verification circuitry.

Again referring to FIG. 10, a clocked set/reset latch is formed by NOR Gate 474, NOR Gate 476 and flip-flop 478. The first input to NOR Gate 474 is the feed back PVER signal, which initially has a logic "0" value since the assumption is made that no P-waves have preceded this detection in the duty cycle. The second input to NOR Gate 474 is $\overline{SPW}$ signal 458. The third input is TCB2+TCB3 signal 472. TCB2 or TCB3 signal 472 has a logic "0" value during each of the respective states and assumes a logic "1" value at the terminal count.

When there is sensing on the P-channel that results in SPW signal 456 having a logic "1" value, $\overline{SPW}$ signal 458 has a logic "0" value. This logic "0" value is input to NOR Gate 474. If the sensed signal does not drop off for an entire clock period, during A1 following generation of a logic "1" value IPW signal, all of the inputs to NOR Gate 474 will be logic "0" values. So the output of NOR Gate 474 will be a logic "1" value. This logic "1" value is input to NOR gate 476 as a first input. The second input to NOR Gate 476 is $\overline{SA0}$ signal 510, which has a logic "0" value in State A1.

Since the inputs to NOR Gate 476 are a logic "0" value and a logic "1" value, the output is a logic "0" value, which is input to the D input to flip-flop 478. On the next positive edge of $\overline{CK1}$ signal 167, a logic "0" value is output from the Q output of flip-flop 478. This signal is the PVER signal.

As stated, the P-wave noise sample period is 101.6 ms. If the sensed signal drops off for an entire clock period, as previously described, $\overline{SPW}$ signal 458 will have a logic "1" value for the period of the signal drop off. This logic "1" value changes the output of NOR Gate 474 from a logic "1" value to a logic "0" value. This logic "0" value is input to NOR Gate 476 as the first input.

The second input to NOR Gate 476 is the $\overline{SA0}$ signal, which is State A1 has a logic "0" value. Therefore, the output of NOR Gate 476 is a logic "1" value which is input to the D input of flip-flop 476. The output from the Q output of flip-flop 478 is the PVER signal having a logic "1" value upon clocking. This is indicative of a verified P-wave, which is one of the signals that inhibits a pacer generated atrial pulse. This logic "1" value is also fed back to NOR Gate 474 and will hold the latch set until reset by $\overline{SA0}$ signal 510 at time out of State A1 and resumption of State A0.

Another feature of the apparatus is that if the main timer, the B Timer, shown in FIG. 20, times out of State B2 or B3 and the apparatus is still sampling to see if there is a verified P-wave, the TCB2+TCB3 signal 472 will change from a logic "0" to a logic "1" value. This logic "1" value has the same effect as the $\overline{SPW}$ signal changing from a logic "0" value to a logic "1" and will produce a PVER signal having a logic "1" value. Essentially, the apparatus does not treat the TCB2 or TCB3 and the sample period still running as noise, it assumes that there was a verified P-wave and inhibits atrial stimulus.

If there is a verified P-wave resulting in a PVER signal with a logic "1" value, the SBP signal 448 will have a logic "0" value subsequent to TCA1 and atrial stimulus from the apparatus is inhibited. The following is a description of the method by which the atrial stimulus is inhibited by a PVER signal having a logic "1" value.

The PVER signal having a logic "1" value is input to NOR Gate 480 as a first input. At the end of the 101.6 ms. period for P-wave sampling, signal TCA1 508 changes from a logic "0" to logic "1" and is input to NAND Gate 486. The output of the gate is then a logic "0" value. This logic "0" value is input to NOR Gate 480 as the second input. Since the inputs to NOR Gate 480 are a logic "0" value and a logic "1" value, the output of NOR Gate 480 is a logic "0" value, which is input to NOR Gate 481 as the second input. NOR Gate 481, with NOR Gate 496 and flip-flop 498 form a clocked latch.

The first input to NOR Gate 481 is the feedback of the output of flip-flop 498, which normally has a logic "0" value unless there has been a failure of the P-wave test during the previous duty cycle. Since both inputs to NOR Gate 481 are logic "0" values, the output is a logic "1" value, which is input to NOR Gate 496 as the first input.

Since one of the inputs to NOR Gate 496 is a logic "1" value, the output is a logic "0" value, regardless of the logic value of the other input. This logic "0" value is input to the D input of flip-flop 498 and on the next positive clock edge of $\overline{CK1}$ signal 167, the output is a logic "0" value, which is the SBP signal indicating that there was not failure of the P-wave verification test.

In the situation when the $\overline{SPW}$ signal has a logic "0" value for the entire 101.6 ms. period of A timer State A1, the Q output of flip flop 478, which is the PVER signal, will have a logic "0" value, which is indicative of a failure of the P-wave verification test. This will mean what was sensed on the P-channel was considered noise. This logic "0" value is input to NOR Gate 480. As stated, when there is a time out of the A1 State, the output of NAND Gate 486 is a logic "0" value. Since both inputs to NAND Gate 486 have a logic "0" value, the output of NOR Gate 480 is a logic "1" value, which is input to NOR Gate 481. Since the feedback logic value from flip-flop 498 as stated is a logic "0" value, which is input to NOR Gate 481, the two inputs to NOR Gate 481 are a logic "0" value and a logic "1" value. The output logic value of NOR Gate 481 is a logic "0" value, which is input to NOR Gate 496 as a first input.

The second input to NOR Gate 496 is TRVD+IRW signal 506. This signal, unless there is premature activity present, is a logic "0" value. Since both inputs are logic "0" values, the output of NOR Gate 496 is a logic "1" value, which is input to the D input of flip-flop 498. On the next positive clock edge of $\overline{CK1}$ signal 167, the Q output of flip-flop 498 assumes a logic "1" value, which is the SBP signal 448, indicative of a blocked P State and failure of the P-wave verification test. Also, there will be no more sensing for P-waves during that duty cycle.

SBP signal 448 is input to NOR Gate 738 (FIG. 14). When this signal has a logic "1" value, it holds the latch formed by NOR Gate 736 and 738 reset. Upon a logic "1" value output of NOR Gate 784, AND Gate 744 will have a logic "1" value output, which is input to the D input of flip-flop 788. Upon the next positive edge of $\overline{CK1}$ 162, a TRA signal having a logic "1" value will be generated.

C-TIMER DESCRIPTION

In the course of describing the DDI modality, DDX modality and the P-wave verification logic circuitry the A timer section and B timer section of the PGSL have been disclosed. However, the C timer section of the PGSL was not disclosed. Therefore, the following is a description of the C timer section of the PGSL.

The C timer section of the PGSL is generally shown at 570 in FIG. 12. The state flip-flops 604 and 606 output signals SC0 and SC1, respectively. These signals dictate the C timer state. The logic values for SC0 and SC1 for the states of the C timer are shown in the following table:

TABLE 4

| C Counter State | SC1 | SC0 |
|---|---|---|
| C0 | 0 | 0 |
| C1 | 0 | 1 |
| C2 | 1 | 1 |
| C3 | 1 | 0 |

Once in a specific C timer state, a TCC signal 632 having a logic "1" value will cause the continuous C timer to change states and advance to the next state except for advancing out of State C0 which is unlimited in duration. For purposes of the explanation of the C timer section of the PGSL, it is assumed that the C timer is in State C1, the absolute refractory period and TCC1 has been reached resulting in TCC signal 632 having a logic "1" value. Immediately preceeding TCC1, the state flip-flops were such that, SC1 signal 628 had a logic "0" value and SC0 signal 626 had a logic "1" value. After TCC1, the state flip-flops will be changed such that SC1 signal 628 will have a logic "1" value and SC0 signal 626 will have a logic "1" value. The following is a description of such state change.

TCC signal 632 having a logic "1" value is input, as the second input to AND Gate 584. The first input to AND Gate 584 is the output of NAND Gate 602 after the signal is processed by inverter 582. The output of NAND Gate 602 is $\overline{C1}$ signal 340.

The first input to NAND Gate 602 is SC0 signal 626 which has a logic "1" value as previously described. The second input is the $\overline{Q}$ output of state flip-flop 606. The Q output of flip-flop 606 is SC1 signal 628 which has a logic "0" value, so the logic value of the $\overline{Q}$ output is a logic "1" value. Since both inputs are logic "1" values, the output of NAND Gate 602 is a logic "0" value which is input to inverter 582. The compliment of the input is output from inverter 582, so a logic "1" value is input to AND Gate 584. Both inputs to AND Gate 584 are logic "1" values, so the output is a logic "1" value, which is input to NOR Gate 592 as the second input.

NOR Gate 592, AND Gate 594, NOR Gate 596 and flip-flop 606 form a clocked set/reset latch. The first input to NOR Gate 592 is a feedback signal from the Q output of flip-flops 606 which is described as a logic "0" value. Since the inputs to NOR Gate 592 are a logic "0" value and a logic "1" value, the output is a logic "0" value, which is the first input to NOR Gate 596. The second input to NOR Gate 596 is IRW+TRVD signal 572 which has a logic "0" value in State C1 because both the R and P channels are refractory during State C1.

The third input to NOR Gate 596 is the output of AND Gate 594. The first signal input to AND Gate 594 is the Q output of flip-flop 606 which as described has a logic "0" value. The second signal input to AND Gate 594 is the Q output of flip-flop 604, which has a logic "0" value since the $\overline{Q}$ output, which is SC0 signal 626, has a logic "1" value. The third signal input is TCC signal 632 which has a logic "1" value. Since at least one input to AND Gate 594 has a logic "0" value, the output of AND Gate 594 is a logic "0" value which is input to NOR Gate 596.

Since all of the inputs to NOR Gate 596 are logic "0" values, the output is a logic "1" value. This value is input to the D input of flip-flops 606 and on the next positive clock edge of $\overline{CK1}$, signal 167, the Q output, which is SC1 signal 628, will assume a logic "1" value.

TCC signal 632 also is input to AND Gate 580. AND Gate 580 along with the latch formed by NOR Gate 598, NOR Gate 600, and flip-flop 604 determine SC0 signal 626. TCC signal 632 having a logic "1" value is input to AND Gate 580 as a first input. The second input is the output of NOR Gate 578.

The first input to NOR Gate 578 is the $\overline{Q}$ output of flip-flop 606, which has a logic "0" value. Since one input is a logic "1" value, the output of NOR Gate 578 is a logic "0" value, which is input to AND Gate 580 as the second input.

Both inputs to AND Gate 580 are not logic "1" values, so the output is a logic "0" value which is input to NOR Gate 598 as a first input. The second input to that gate is the Q output of flip-flop 604 which has a logic "0" value. Since both inputs are logic "0" values, the output of NOR Gate 598 is a logic "1" value. This logic "1" value is input to NOR Gate 600 as the first input. The second input is IRW+TRVD signal 572 which as described in State C1 has a logic "0" value. Since the inputs to NOR Gate 600 are a logic "1" value and logic "0" value, the output is a logic "0" value that is input to the D input of flip-flop 604. On the next positive clock edge of $\overline{CK1}$ signal 167, a logic "0" value is output from the Q output and SC0 signal 626 output from the $\overline{Q}$ output of that flip-flop has a logic "1" value.

The logic values of both SC1 signal 628 and SC0 signal 626 are logic "1" values which are indicative of C timer State C2 being set following TCC1.

B-TIMER DESCRIPTION

Figure 19:
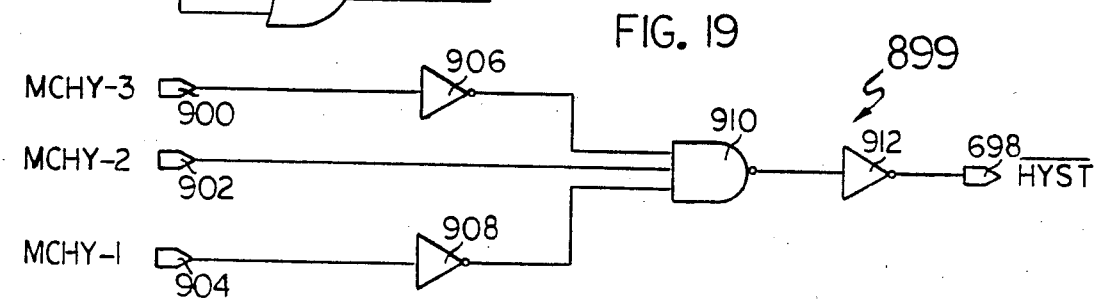
FIG. 19 shows the hysteresis logic in the B-timer.

The main timer of the apparatus, the B timer, is shown in FIGS. 16, 17, 18, 19 and 20A and B. The major portions of the logic circuitry for the timer are shown generally at 920 and 921 in FIG. 20A and B, respectively. The logic circuitry shown generally at 829 of FIG. 16; generally at 837 of FIG. 17; generally at 879 of FIG. 18 and generally at 899 of FIG. 19, are portions of the B timer circuitry. The B timer is preloadable to 0, 50.8 ms., 101.6 ms. or the A-V delay dependent on the control signals AVLD signal 722 and BPLCK signal 718.

Referring to FIG. 13, the control signals AVLD signal 722 and BPLCK signal 718 are generated from the outputs of AND Gate 686 and NOR Gate 684, respectively.

The first input to AND Gate 686 is DDD+DVI+DOO+DDI+DDX signal 352, which as described in a dual chamber mode has a logic "1" value. The second input is SB1 signal output from the $\overline{Q}$ output of flip-flop 676. The SB1 signal will have a logic "1" value in the B2 or B3 States. Therefore, AVLD signal 722 can have a logic "1" value only during States B2 or B3. When these events occur, the preloaded A-V delay will be provided upon clocking of the B timer counters by BPLCK signal 718. In situations when AVLD signal 722 is a logic "0" value (during B timer State B0 and B1) and there is clocking of the B timer counters by BPLCK signal 718, the preload value for the AV delay will be 50.8 ms. if the actual programmed value of A-V delay is less than 100 ms.; and 101.6 ms. if the actual programmed value of A-V delay is more than 100 ms. This will be described in the disclosure in conjunction with the description of FIGS. 16, 17, 18, 19 20A and 20B.

BPLCK signal 718 is generated from the output NOR Gate 684. The first input to NOR Gate 684 is $\overline{CK2}$ signal 169. The second input to NOR Gate 684 is the Q output of flip-flop 678. In order for NOR Gate 684 to have a logic "1" value output both inputs must be a logic "0" value. The $\overline{CK2}$ signal will have a logic "0" value until the positive going edge. The Q output of flip-flop 678 will be a logic "0" value when a logic "0" value is input to the D input of flip-flop 678 when it is clocked.

The output of NOR Gate 674 is input to the D input of flip-flop 678. The inputs to NOR Gate 674 are, previously described signals, TRVD+IRW signal 572, $\overline{DDI}$ TCA1 (PVER+TCB2+TCB3) signal 644, and TRAD signal 646. These signals normally have logic "0" values except at the happening of a TRA, TRV, verified P-wave (PVER) or an inhibited R-wave (IRW).

Whenever one of these events take place, at least one of the input logic values will have a logic "1" value, which causes the output of NOR Gate 674 to assume a logic "0" value. This in turn produces a logic "0" value input to the D input to flip-flop 678 for sampling during the next clocking of the flip-flop. On such clocking the output of NOR Gate 684 assumes a logic "1" value, when $\overline{CK2}$ signal 169 has a logic "0" value.

Referring to FIG. 20A, BPLCK signal 718 is input to the preset enable input of UP counters 834 (FIG. 16), 978, 982, 986, 990 and 994 of the B timer. When these counters are enabled by BPLCK signal 718, the preset input values are output from the Q outputs of the respective counters. The preset values loaded into the counters are determined by the programmed value for the A-V delay period in memory.

Figure 17:
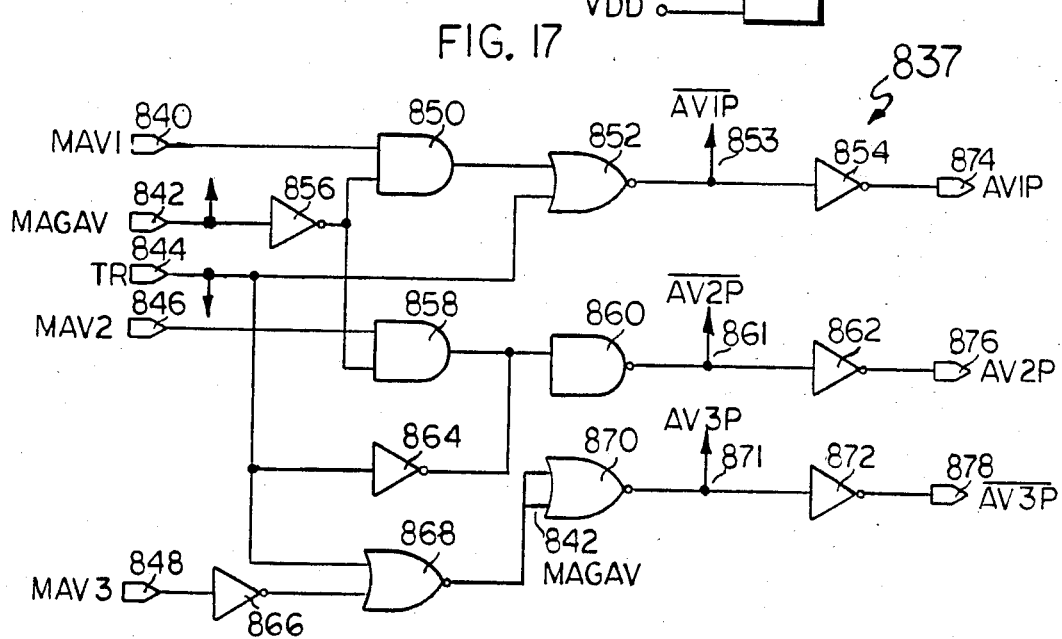
FIG. 17 shows the logic for input from memory to the B-timer.

Referring to FIG. 17, the memory parameters for A-V delay are MAV-1 signal 840, MAV-2 signal 846 and MAV-3 signal 848. For simplicity of explanation, MAV-1 signal 840 has a logic "0" value; MAV-2 signal 846 has a logic "0" value; and MAV-3 signal 848 has a logic "0" value, which is indicative of a programmed A-V delay of 215 ms.

The logic "0" value of MAV-1 signal 840 is input to AND Gate 850. The second input to AND Gate 850 is MAGAV signal 842 after it passes through inverter 856. Unless a magnet is used to close the reed switch 2 (FIG. 1), the logic value of this signal is a logic "0" value. Therefore, the inputs to AND Gate 850 are a logic "0" and "1" value, so the output of this Gate is a logic "0" value, which is input as a first input to NOR Gate 852.

The second input to NOR Gate 852 is TR signal 844. This signal is indicative of a special temporary rate of 30 bpm (beats per minute) ordered by a physician. In all cases, except for this one case, TR signal 844 has a logic "0" value. Since both inputs have a logic "0" value, the output of NOR Gate 852 is a logic "1" value, which is $\overline{AV1P}$ signal 853. This signal is processed by inverter 854. This resultant signal is AV1P signal 874 having a logic "0" value.

MAV-2 signal 846 has a logic "0" value, as previously described. This logic "0" value is input to AND Gate 858 as a first input. The second input to AND Gate 858 is MAGAV signal 942 after passing through inverter 150. As described, the MAGAV signal 842 is a logic "0" value, therefore, a logic "1" value is input as a second input to AND Gate 858. The inputs to AND Gate 858 are a logic "0" value and a logic "1" value, so the output of this Gate is a logic "0" value, which is input to NAND Gate 860 as the first input.

The second input to NAND Gate 860 is TR signal 844 after it passes through inverter 864. TR signal 844, as previously described has a logic "0" value, so a logic "1" value will be input to NAND Gate 860. Since all of the inputs to NAND Gate 860 are not logic "1" values, the output of NAND Gate 860 is a logic "1" value.

The output of NAND Gate 860 is an $\overline{AV2P}$ signal 861. This signal is processed by inverter 862, and provides AV2P signal 876 having a logic "0" value.

MAV-3 signal 848 having a logic "0" value is input to NOR Gate 868 after passing through inverter 866. Therefore, a logic "1" value is input to NOR Gate 868 as the second input. The first input to NOR Gate 868 is TR signal 844, which as previously described has a logic "0" value. The inputs to NOR Gate 868 are a logic "1" value and a logic "0" value, so, the output of this Gate is a logic "0" value. This output is input, as a first input, to OR Gate 870. The second input to OR Gate 870 is MAGAV signal 842, which as described has a logic "0" value. Since both inputs to OR Gate 870 are logic "0" values, the output of OR Gate 870 is a logic "0" value. The output of OR Gate 870 is AV3P signal 871. This signal is processed by inverter 872 and the resultant signal is $\overline{AV3P}$ signal 878 having a logic "1" value.

AV1P signal 853; AV1P signal 874; $\overline{AV2P}$ signal 861; AV2P signal 876, AV3P signal 871; and $\overline{AV3P}$ signal 878 are input to FIG. 20 in various places. These signals will determine the terminal count on the B timer.

Referring to FIG. 19, the logic Gates for generating $\overline{HYST}$ signal 698 are generally shown at 899. This will have a logic "0" value when hysteresis is programmed. The period of hysteresis is timed out by B timer State B3. MCHY 1, 2 and 3 signals, 904, 902 and 900 respectively, are programmed into memory for the period of hysteresis. Hysteresis is only for single chamber operations. For purposes of explanation, the programmed period of hysteresis is 1625 ms. For this period, MCHY-1 signal 904 has a logic "0" value; MCHY-2 signal 902 has a logic "0" value; and MCHY-3 signal 900 has a logic "0" value. The three signals are input to NAND Gate 910. However, MCHY-1 signal 904 passes through inverter 908 and MCHY-3 signal 900 passes through inverter 906 before being input to NAND Gate 910. Therefore, MCHY-1 signal 904 and MCHY-3 signal 900 have their compliments input to NAND Gate 910. Since at least one input to NAND Gate 910 has a logic "0" value, the output of NAND Gate 910 is a logic "1" value. This logic "1" value output is processed by inverter 912 and the resultant output is a logic "0" value, which is $\overline{HYST}$ signal 698 and indicative of hysteresis being operative. However, under normal circumstances when basic pacing is being accomplished, the $\overline{HYST}$ signal 698 will be a logic "1" value indicating that hysteresis is not programmed.

Figure 16:
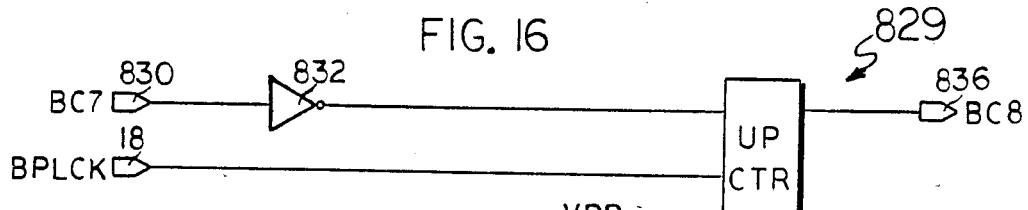
FIG. 16 shows a portion of B-timer logic.
Figure 20B:
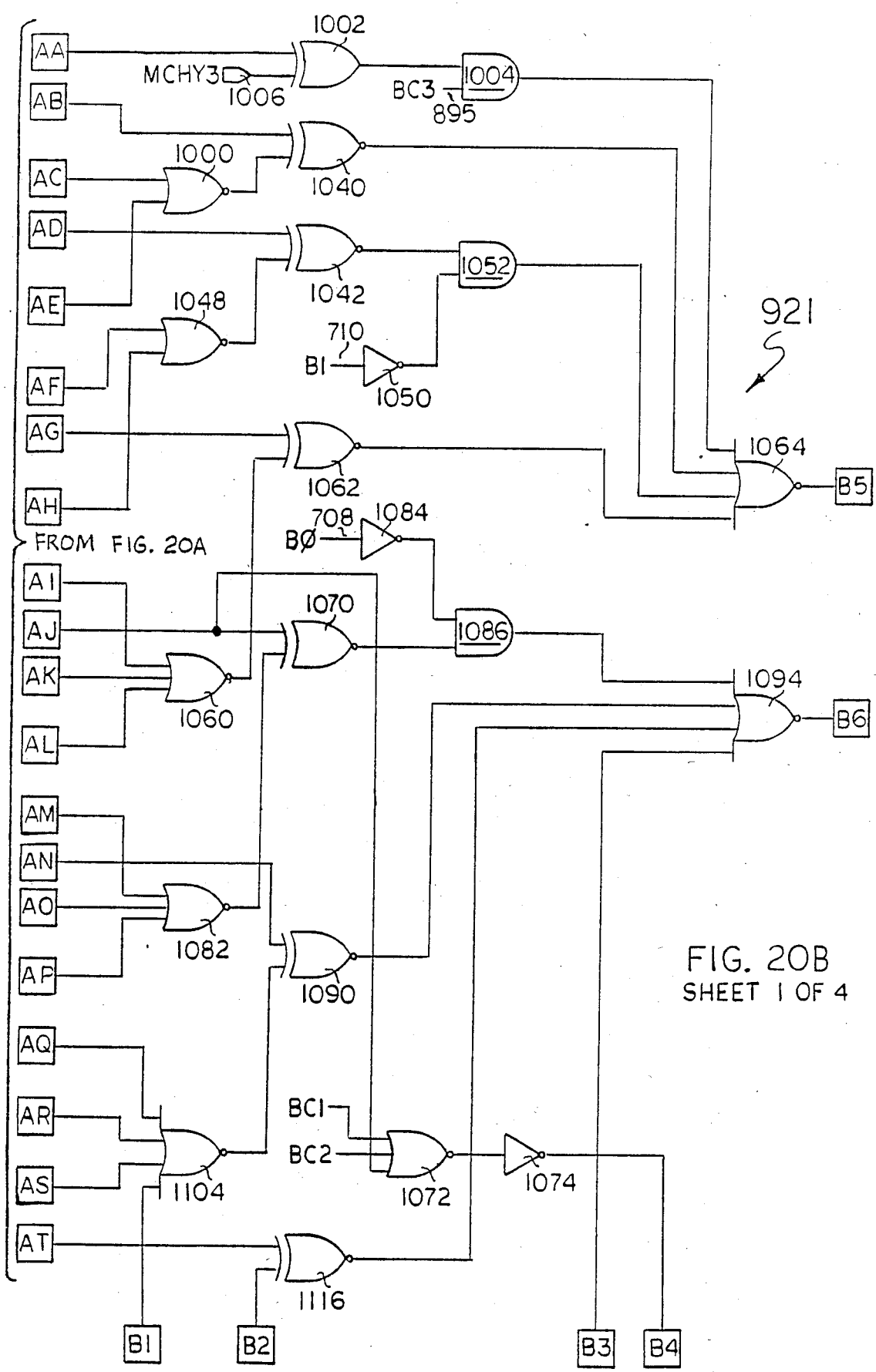
FIG. 20B shows the B-timer logic less the logic circuits of FIGS. 17, 18 and 19.
Figure 20B:
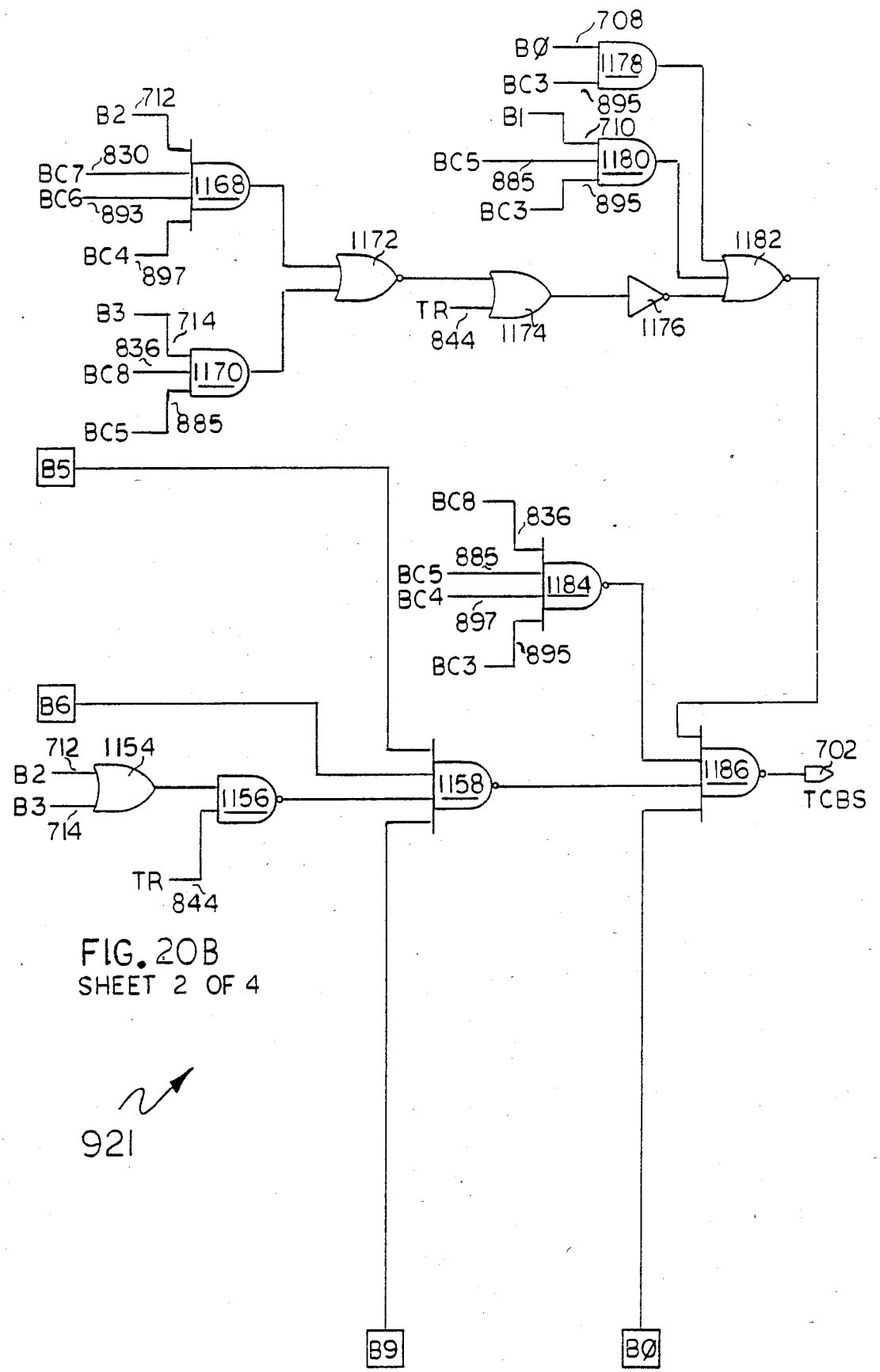
Figure 20B:
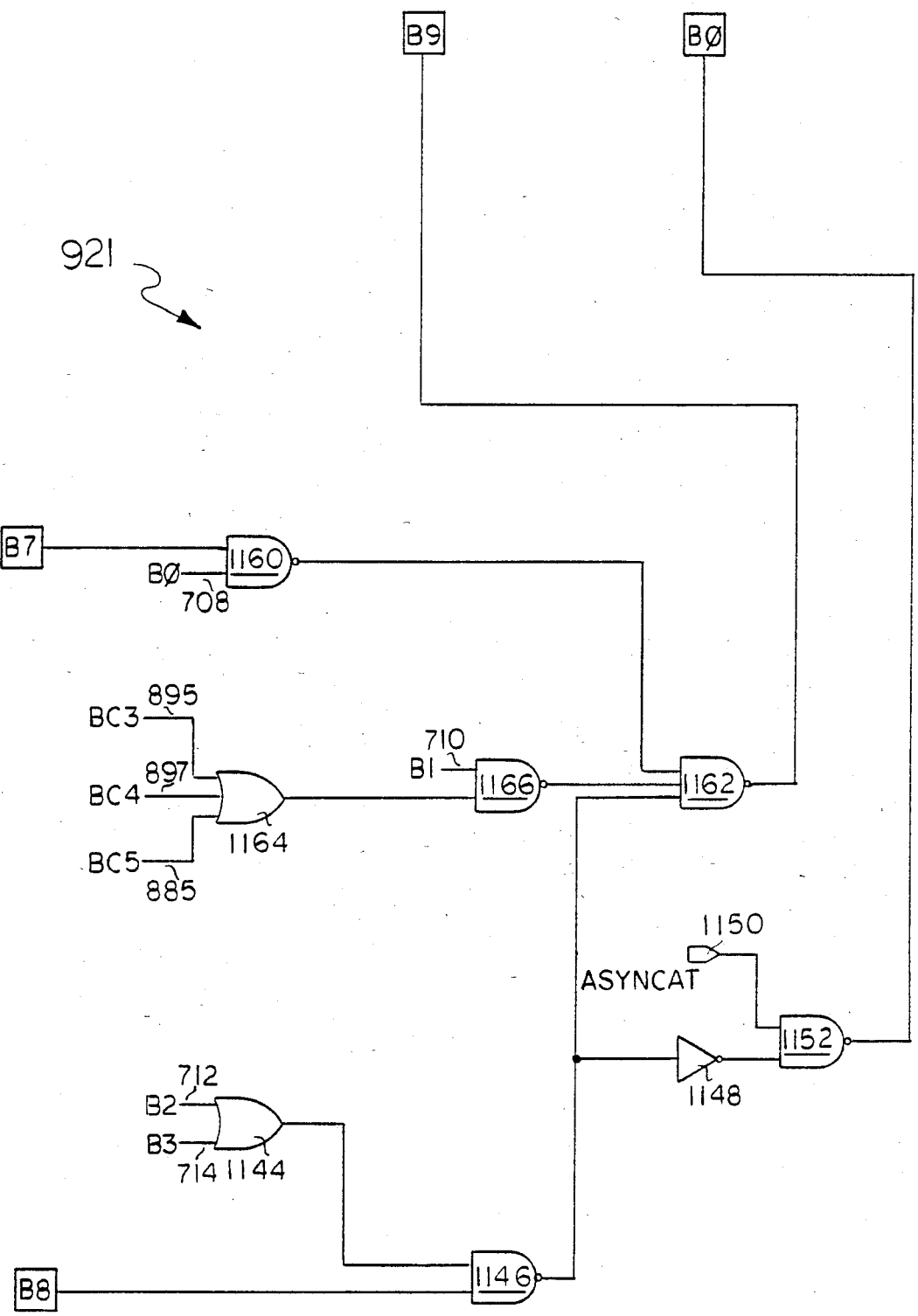
Figure 21A:
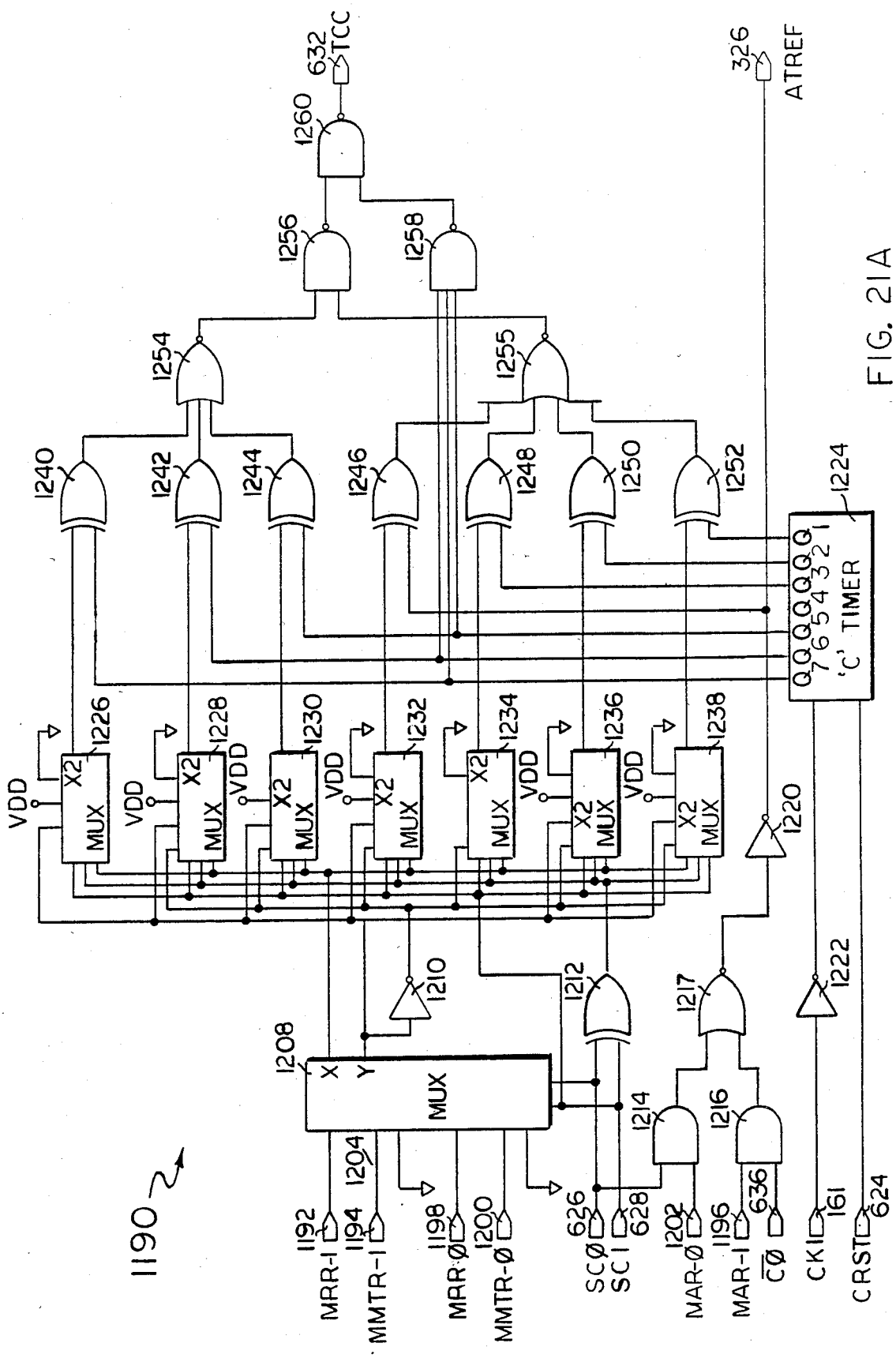
FIG. 21A shows the C-timer logic.

Referring to FIGS. 20A and 20B, the main portions of the B timer are shown generally at 920. The main operative sections of the B timer are UP counter 978, 982, 986, 990, 994 and 834 (FIG. 16). These counters function as a continuous counter for counting out B timer States B0, B1, B2 (or B3). These counters along with the associated logic circuitry generate TCBS signal 702, the terminal count of the B timer, which is input to PGSL logic circuitry in FIG. 13. First the preload section of the B timer will be described and then the remaining logic circuitry of the B timer will be described.

The preload logic values are input to the respective up counters. The UP counters are connected such that the Q output of one counter is used to clock the next counter. After initiation of the count, UP counter 994 has a logic "1" value every 6.35 ms., UP counter 990 has a logic "1" value every 12.7 ms., UP counter 986 has a logic "1" value every 25.4 ms.; UP counter 982 has a logic "1" value every 50.8 ms.; UP counter 978 has a logic "1" value every 101.6 ms. at the BC4 signal 897 output, every 203.2 ms. at BC5 signal output 887, every 406.4 ms. at BC6 signal output 893, and every 812.8 ms. at BC7 signal output 830. The BC8 signal 836 output from UP counter 834 has a logic "1" value every 1625.6 ms. (FIG. 16).

Each counter has BPLCK signal 718 input to the preset enable input. When the BPLCK signal 718 has a logic "1" value, the preset value will be output from the respective counter A regardless of the count generated by the counters.

For purposes of description of the preload portion of the B timer, it is assumed that the B timer is in State B2, that AVLD signal 722 is a logic "1" value and $\overline{AVLD}$ signal 723 is a logic "0" value.

The preload value for UP counter 994 is generated from the output of NOR Gate 946. There are two inputs to NOR Gate 946. The first is $\overline{AVLD}$ signal 723 and the second is $\overline{FASTEN}$ signal 954. $\overline{AVLD}$ signal 723 has a logic "0" value as described.

The second signal is $\overline{FASTEN}$ signal 954. This signal will have a logic "0" value only when the apparatus paces at a rate 11% faster than the basic programmed rate so the signal has a logic "1" value.

Since the inputs to NOR Gate 946 are a logic "0" value and a logic "1" value, the output of NOR Gate 946 is a logic "0" value, which is input to UP counter 994 as the preload value.

The preload value for UP counter 990 is generated from the output of NOR Gate 944. The inputs to NOR Gate 944 are $\overline{AVLD}$ signal 723 which has a logic "0" value and $\overline{FASTEN}$ signal 954 after passing through inverter 948. Since the signal passes through inverter 948, the compliment of $\overline{FASTEN}$ signal 954 is provided as the second input to NOR Gate 944. Both inputs to NOR Gate 944 are logic "0" values, so the output is a logic "1" value which is input to UP counter 990 as the preload value.

The preload value input to UP counter 986 is generated from the output of NOR Gate 942. The inputs to NOR Gate 942 are $\overline{AV1P}$ signal 853 and $\overline{AVLD}$ signal 723. As previously described, $\overline{AV1P}$ signal 853 has a logic "1" value and $\overline{AVLD}$ signal 723 has a logic "0" value. Since the inputs signals are a logic "1" value and a logic "0" value, the output of NOR Gate 942 is a logic "0" value, which is input to UP counter 986 as the preload value.

The preload value input to UP counter 982 is the output of NAND Gate 940. The inputs to NAND Gate 940 are the output of OR Gate 934 and the output of NAND Gate 937. The first input to OR Gate 934 is $\overline{AVLD}$ signal 723 having a logic "0" value. The second input to OR Gate 934 is $\overline{AV2P}$ signal 861, which is previously described was a logic "1" value. Since the inputs are a logic "0" value and a logic "1" value, the output of OR Gate 934 is a logic "1" value, which is input as the first input to NAND Gate 940.

There are three inputs to NAND Gate 937. The inputs are B1 signal 710, $\overline{AV3P}$ Signal 878, and $\overline{AV2P}$ signal 861 after passing through inverter 936. B1 signal 710 has a logic "0" value because, as stated, State B2 is being assumed. $\overline{AV3P}$ signal, as stated, has a logic "1" value. $\overline{AV2P}$ signal 861 is input to NAND Gate 937 after passing through inverter 936. As stated, AV2P has a logic "1" value, so the input to NAND Gate 937 is a logic "0" value. At least one of the inputs to NAND Gate 937 is a logic "0" value, so, the output of NAND Gate 937 is a logic "1" value, which is input to NAND Gate 940 as a second input.

Both inputs to NAND Gate 940 are logic "1" values so the output of NAND Gate is a logic "0" value, which is the preload value for UP counter 982.

There are four preload values input to UP counter 978. The first preload value is input to the counter at $P_1$, which equates to 16 clock periods for the overall binary counter. The second is input at $P_2$, which equates to 32 clock periods for the overall binary counter. The third and fourth are grounded and are the $P_3$ and $P_4$ inputs, respectively. The third and fourth input of $P_3$ and $P_4$ represent 64 and 128 clock periods, respectively.

The preload value of the first input, $P_1$, is determined by the output of NAND Gate 928. The inputs to NAND Gate 928 are the outputs of OR Gate 926 and NAND Gate 932. The inputs to OR Gate 926 are $\overline{AVLD}$ signal 723 having a logic "0" value and $\overline{AV3P}$ signal 878 having a logic "1" value. Since one of the inputs has a logic "1" value, the output of OR Gate 926 is a logic "1" value which is input to NAND Gate 928 as the first input.

NAND Gate 932 has two inputs. The first is B1 signal 710, which has a logic "0" value, and the second is the output of OR Gate 930. The inputs to OR Gate 930 is AV3P signal 871 having a logic "0" value and $\overline{AV2P}$ signal 861 having a logic "1" value. Since the logic value inputs to OR Gate 930 are a logic "1" value and a logic " " value, the output logic value is a logic "1" value, which is the second input to NAND Gate 932.

The inputs to NAND Gate 932 are a logic "0" value and a logic "1" value, so the output of that Gate is a logic "1" value, which is input to NAND Gate 928 as its second input. The two inputs to NAND Gate 928 have logic "1" values, so, the output of NAND Gate 928 is a logic "0" value, which is the preload value for the $P_1$ input to UP counter 978.

The preload value for the second input, $P_2$, to UP counter 978 is the output of NOR Gate 924. The three inputs to NOR Gate 924 are $\overline{AVLD}$ signal 723 having a logic "0" value; AV2P signal 876 having a logic "0" value; and AV3P signal 871 having a logic "0" value. Since all of the inputs have a logic "0" value, the output of that Gate is a logic "1" value, which is the preload value for the $P_2$ input of UP counter 978.

The preload values loaded in the UP counters are output from the counters upon the timing out of State B2 or B3, when BPLCK signal has a logic "1" value. BPLCK signal 718 will have a logic "1" value one clock period (6.35 ms.) after a verified P-wave. Therefore, the count will begin at the preload value not at zero. The preload value will cause the count to start at State B1 not State B0.

UP counters 986, 990 and 994 can be reset when the output of NOR Gate 976 assumes a logic "1" value. In the reset condition, the Q outputs of each counter will assume a logic "0" value.

There are two inputs to NOR Gate 976. The first input is $\overline{FASTEN}$ signal 954 which, as described, has a logic "1" value. The second input is generated from the output of NAND Gate 972.

The output of NAND Gate 972 is determined by NAND Gate 970, AND Gate 974, inverters 968, 960 and 962, and NAND Gate 1120. NAND Gate 970 and 972 form a latch.

When the counters have counted out 38.1 ms. (or 6 clocks) $\overline{BC0}$ signal will have a logic "1" value, BC1 signal 889 will have a logic "1" value (the output of UP counter 990); and BC2 signal 891 will have a logic "1" value (the output of UP counter 986). These logic "1" values are input to NAND Gate 1120. When all of the inputs are a logic "1" value, the output of NAND Gate 1120 is a logic "0" value which is input to NAND Gate 970 as the first input.

The second input to NAND Gate 970 is the output of NAND Gate 972, which is in a feedback loop from NAND Gate 972. To arrive at a value for the output of NAND Gate 972, the signal processing of inverters 950, 960 and 962; and AND Gate 974 must be described.

AND Gate 974 has two inputs. The first is BPLCK signal 718 after it passes through inverter 968. Therefore when BPLCK signal has a logic "0" value, a logic "1" value is input to AND Gate 974. Therefore, under these conditions the preloading of the counters will have no affect on counters 986, 990 and 994.

The second input to AND Gate 974 is CK1 signal 161 after passing through inverters 950, 960 and 962. Since the CK1 signal passes through the three inverters, there is a time delay for the signal and a resulting logic value change. On the negative going edge of CK1, the output of inverter 962 will assume a logic "1" value which is input to AND Gate 974 as the second input. When both inputs have a logic "1" value, the output of the gate is a logic "1" value which is input to NAND Gate 972.

The other input to NAND Gate 972 is the output of NAND Gate 970. As previously stated, the output of NAND Gate 1120 is a logic "0" value which is input to NAND Gate 970. This is true only at the 6 clock periods count. When this logic "0" value is input to NAND Gate 970, the output of that Gate is a logic "1" value regardless of the logic value of the other input. This logic "1" value output is input to NAND Gate 972. Both inputs to NAND Gate 972 are logic "1" values which causes the output of NAND Gate 972 to assume a logic "0" value, which is input to NOR Gate 976 as the second input.

The inputs to NOR Gate 976 are a logic "0" value and a logic "1" value, so the output is a logic "0" value output. Therefore, under these conditions when $\overline{\text{FAS TEN}}$ signal 954 assumes a logic "0" value counters 994, 990, and 986 will be reset.

The clock signal for clocking the entire binary counter consisting of UP counters 994, 990, 986, 978, and 834 is the output of NOR Gate 952. There are two inputs to NOR Gate 952. The first is CK1 signal 161 after passing through inverter 950 and the second is the Q output of J-K flip-flop 966. On every positive edge of CK1 signal 161, a logic "0" value signal will be input to NOR Gate 952 because of inverter 950.

The Q output of J-K flip-flop 966 will assume a logic "0" value when the J input of that flip-flop is loaded with a logic "0" value because the K input is connected to Vdd having a logic "1" value.

The J input is loaded by the output of NOR Gate 958. The inputs to NOR Gate 958 are $\overline{\text{SLOEN}}$ signal 956, which has a logic "1" value, and the output of NAND Gate 1120. Since the $\overline{\text{SLOEN}}$ signal 956 has a logic "1" value normally, the output of NOR Gate 958 will assume a logic "0" value output.

NOR Gate 958 has a logic "0" value output, which is input to the J input of flip-flop 966. When the clock signal value is on the positive edge, the Q output will assume the value of the J input because the J input and K are complements. Therefore on each clocking of flip-flop 966, a logic "0" value is output from the Q output and input to NOR Gate 952. Clock signal 161 will arrive at NOR Gate 952 delayed a time period consistent with processing by the inverters 950, 960 and 962. On the positive edge of CK1 signal 161, a logic "1" value will be output by NOR Gate 952 to clock the series of counters.

The following is a description of the B timer for generating a terminal count on the timer. For purposes of example, the period of State B0, the blanking period, is 12.7 ms.; State B1, the AV delay period, is 215 ms.; State B2, the basic period, is 812.5 ms. ±0 and hysteresis is 1625 ms. ±0. Therefore, the logic values programmed in memory are as shown in the following table:

TABLE 5

| Signal | Logic Value |
|---|---|
| MBLK-0 | 1 |
| MBLK-1 | 0 |
| $\overline{\text{AVIP}}$ | 0 |
| AVIP | 1 |
| $\overline{\text{AV2P}}$ | 0 |
| AV2P | 1 |
| $\overline{\text{AV3P}}$ | 0 |
| AV3P | 1 |
| MCBP-0 | 0 |
| MCBP-1 | 0 |
| MCBP-2 | 0 |
| MCBP-3 | 0 |
| MFBP-0 | 0 |
| MFBP-1 | 0 |
| MFBP-2 | 0 |
| MCHY-0 | 0 |
| MCHY-1 | 0 |
| MCHY-2 | 0 |
| MCHY-3 | 0 |
| MFHY-0 | 0 |
| MFHY-1 | 0 |
| MFHY-2 | 0 |
| MFPY-3 | 0 |

Referring to FIGS. 20A and B and assuming normal operating conditions, at the terminal count of State B0 (TCB0), BC1 signal 889 has a logic "1" value indicative of 12.7 ms. No other counter output will have a logic "1" value output from its Q output. This logic "1" value is output to various places in the logic circuitry.

BC0 signal 887 is input, as a first input, to XNOR Gate 1134. The second input to that Gate is the output of NOR Gate 1132. The first input to NOR Gate 1132 is the output of AND Gate 1124. The inputs to AND Gate 1124 are B2 signal 712, having a logic "0" value in State B0 and MFBP-1 signal 1036 having a logic "0" value. Since both inputs to AND Gate 1124 have logic "0" values, the output of that Gate is a logic "0" value which is input as the first input to NOR Gate 1132.

The second input to NOR Gate 1132 is the output of AND Gate 1126. The first input to that AND Gate 1126 is B3 signal 714 having a logic "0" value in State B0. The second input to AND Gate 1126 is MFHY-0 signal 1038 which has a logic "0" value. Since both inputs to AND Gate 1126 are logic "0" values, the output is a logic "0" value which is input to NOR Gate 1132 as the second input.

The third input is B1 signal 710 which has a logic "0" value in State B0. Since all of the inputs to NOR Gate 1132 are logic "0" values, the output logic value is a logic "1" value which is input to NOR Gate 1134 as the second input.

The inputs to XNOR Gate 1134 are a logic "1" value and logic "0" value. The output of that Gate is a logic "0" value, which is input to AND Gate 1136. Since this input to AND Gate 1136 is a logic "0" value, the output of AND Gate is a logic "0" value, regardless of the logic values of the other input. This logic "0" value output from AND Gate 1136 is input to NOR Gate 1094 as the fourth input.

The third input to NOR Gate 1094 is the output of XNOR Gate 1116. The first input to that Gate is BC1 signal 889 which has a logic "1" value as stated. The second input is the output of NOR Gate 1114. The inputs to NOR Gate 1114 are the outputs of AND Gates 1108, 1110 and 1118.

The inputs to AND Gate 1108 are B2 signal 712 having a logic "0" value in State B0 and MFBP-2 signal 1030 which has a logic "0" value. Since both inputs are logic "0" values, the output is a logic "0" value that is input to NOR Gate 1114 as the second input.

The inputs to AND Gate 1110 are B3 signal 714 having a logic "0" value in State B0 and MFHY-1 signal 1032 having a logic "0" value. Both inputs are logic "0" values, so the output is a logic "0" values, which is input as the third input to NOR Gate 1114.

The first input to NOR Gate 1114 is the output of AND Gate 1118. The inputs to this Gate are B0 signal 708 having a logic "1" value and MBLK-0 signal 1034 having a logic "1" value. Since both inputs on a logic "1" value, the output logic value is a logic "1" value, which is input as the first input to NOR Gate 1114.

The inputs to NOR Gate 1114 are two logic "0" values and a logic "1" value, so, the output of that Gate is a logic "0" value which is input to XNOR Gate 1116 as the second input. Since the inputs to XNOR Gate 1116 are a logic "1" value and "0" value, the output logic value of this Gate is a logic "0" value, which is input to NOR Gate 1094 as the third input.

The second input to NOR Gate 1094 is the output of AND Gate 1086. The first input to that Gate is B0 signal 708 after it passes through inverter 1084. The B0 signal has a logic "1" value, so the logic value input to AND Gate 1086 is a logic "0" value. Since the first input to AND Gate 1086 is a logic "0" value, the output logic value of that Gate is a logic "0" value regardless of the logic value of the other input.

The first input to NOR Gate 1094 is the output of XNOR Gate 1090. The first input to XNOR Gate 1090 is BC2 signal 891 having a logic "0" value. The second input is the output of NOR Gate 1104. NOR Gate 1104 has four inputs.

The first input to NOR Gate 1104 is the output of AND Gate 1096. The inputs to AND Gate 1096 are B1 signal 710 having a logic "0" value and AVIP signal 874 has a logic "0" value, so the output of that Gate is a logic "0" value.

The second input to NOR Gate 1104 is the output of AND Gate 1098. The inputs to AND Gate 1098 are B2 signal 712 having a logic "0" value and MFBP-3 signal 1024 having a logic "0" value, so the output of this Gate is a logic "0" value.

The third input to NOR Gate 1104 is the output of AND Gate 1100. The inputs to this Gate are B3 signal 714 having a logic "0" value and MFHY-2 signal 1026 having a logic "0" value. So, the output logic value of this Gate is a logic "0" value.

The fourth input to NOR Gate 1104 is the output of AND Gate 1106. The inputs to this gate are B0 signal 708 having a logic "1" value and MBLK-1 signal 1028 having a logic "0" value. Since one input has a logic "0" value, the output logic value of the Gate is a logic "0" value which is input to NOR Gate 1104 as the fourth input. Since all of the inputs to NOR Gate 1104 are logic "0" values, the output logic value of NOR Gate 1104 is a logic "1" value which is input as the second input as XNOR Gate 1090.

The two inputs to XNOR Gate 1090 are logic "1" and "0" values, so the output is a logic "0" value which is input as the first input to NOR Gate 1094.

All of the inputs to NOR Gate 1094 are logic "0" values, so, the output is a logic "1" value, which is input to NAND Gate 1158 as the third input.

The first input to NAND Gate 1158 is the output of NAND Gate 1156. The inputs to that NAND Gate are the output of OR Gate 1154 and TR signal 844. The logic value of TR signal 844 is a logic "0" value as previously described. The inputs to OR Gate 1154 are B2 signal 712 and B3 signal 714 which each have a logic "0" value at TCB0, so the output of OR Gate 1154 is a logic "0" value. Since both inputs to NAND Gate 1156 have a logic "0" value, the output of that Gate is a logic "1" value, which is input to NAND Gate 1158 as the first input.

The second input to NAND Gate 1158 is the output of NOR Gate 1064. This Gate has four inputs, the output of AND Gate 1004; the output of XNOR Gate 1040; the output of AND Gate 1052; and the output of XNOR Gate 1062.

The inputs to AND Gate 1004 are the output of XOR Gate 1002 and BC3 signal 895. At a 12.7 ms. count, BC3 signal 895 has a logic "0" value and this value is input to AND Gate 1004 as the second input. The inputs to XNOR Gate 1002 are BC7 signal 830, which has a logic "0" value at the 12.7 ms. count, and MCHY-3 signal 1006, which has a logic "0" value as indicated in Table 5 above. Therefore, the output of XOR Gate 1002 is a logic "0" value, which is input to AND Gate 1004. Both inputs to AND Gate 1004 are logic "0" values, so the output of that Gate is a logic "0" value which is input to NOR Gate 1064 as its first input.

The inputs to XNOR Gate 1040 are BC6 signal 893, having a logic "0" value at a 12.7 ms. count, and the output of NOR Gate 1000. The inputs to NOR Gate 1000 are the outputs of AND Gates 996 and 998. The inputs to AND Gate 996 are B2 signal 712, having a logic "0" value at TCB0, and MCBP-3 having a logic "0" value as indicated in Table 5. So, the output of AND Gate 996 is a logic "0" value, which is input to NOR Gate 1000 as the first input.

The first input to AND Gate 998 is B3 signal 714, which has a logic "0" value at TCB0 and the second input is MCHY-2 signal 1010, which has a logic "0" value, as indicated in Table 5. Therefore, the output of AND Gate 998 is a logic "0" value, which is input to NOR Gate 1000 as the second input.

Since both inputs to NOR Gate 1000 are logic "0" values, the output of that Gate is a logic "1" value, which is input to XNOR Gate 1040. The two inputs to XNOR Gate 1040 are a logic "1" value and a logic "0" value, so the output of that Gate is a logic "0" value, which is input to NOR Gate 1064 as the second input.

The third input to NOR Gate 1064 is the output of AND Gate 1052 which has inputs from XNOR Gate 1042 and inverter 1050. The inputs to XNOR Gate 1042 are BC5 signal 887, which has a logic "0" value at the 12.7 ms. count, and the output of NOR Gate 1048. The inputs to NOR Gate 1048 are the outputs of AND Gates 1044 and 1046.

The inputs to AND Gate 1044 are B2 signal 712, which has a logic "0" value at TCB0, and MCBP-2 signal 1012, which has a logic "0" value as indicated in Table 5 above. The output of AND Gate 1044 is a logic "0" value, which is input to NOR Gate 1048. The inputs to AND Gate 1046 are B3 signal 714, which has a logic "0" value at TCB0, and MCHY-1 signal 1014, which has a logic "0" value, as indicated in Table 5 above. The output of AND Gate 1046 is a logic "0" value, which is input to NOR Gate 1048 as the second input. Since both inputs to NOR Gate 1048 are logic "0" values, the output is a logic "1" value, which is input to XNOR Gate 1042 as a second input.

The two inputs to XNOR Gate 1042 are a logic "0" value and a logic "1" value. Therefore, the output of XNOR Gate 1042 is a logic "0" value, which is input to AND Gate 1052 as a first input.

The second input to AND Gate 1052 is the output of inverter 1050. The input to inverter 1050 is B1 signal 710, which has a logic "0" value at TCB0. Therefore, the output of inverter 1050 is a logic "1" value, which is input to AND Gate 1052.

The inputs to AND Gate 1052 are a logic "0" value and a logic "1" value. These inputs will cause a logic "0" value output from AND Gate 1052, which is input to NOR Gate 1064 as the third input.

The fourth input to NOR Gate 1064 is the output of XNOR Gate 1062. The inputs to XNOR Gates 1062 are BC4 signal 897, which is a logic "0" value at the 12.7 ms. count, and the output of NOR Gate 1060. The inputs to NOR Gate 1060 are the outputs of AND Gate 1054, 1056 and 1058.

The inputs to AND Gate 1054 are B1 signal 710 having a logic "0" value and AV3P signal having a logic "0" value, as indicated above. The output of AND Gate 1054 is a logic "0" value, which is input to NOR Gate 1060 as the first input.

The inputs to AND Gate 1056 are B2 signal 712, which has a logic "0" value at TCB0, and MCBP-1 signal 1016, which has a logic "0" value, as indicated above. The output of AND Gate 1056 is a logic "0" value, which is input to NOR Gate 1060 as a second input.

The inputs to AND Gate 1058 are B3 signal 714 which has a logic "0" value at TCB0, and MCHY-0 signal 1018, which has a logic "0" value, as indicated above. Both inputs to AND Gate 1058 are logic "0" values, so the output is a logic "0" value, which is input to NOR Gate 1060 as the third input.

The three inputs to NOR Gate 1060 are logic "0" values, so the output is a logic "1" value, which is input to XNOR Gate 1062 as the second input. The inputs to XNOR Gate 1062 are a logic "1" value and a logic "0" value, so, the output is a logic "0" value, which is input to NOR Gate 1064 as the fourth input.

All of the inputs to NOR Gate 1064 have a logic "0" value, so the output is a logic "1" value. This logic "1" value is input to NAND Gate 1158 as the second input.

The fourth input to NAND Gate 1158 is the output of NAND Gate 1162. The inputs to NAND Gate 1162 are the outputs of NAND Gate 1160, the output of NAND Gate 1166 and the output of NAND Gate 1146.

The inputs to NAND Gate 1160 are B0 signal 708, which has a logic "1" value at TCB0, and the output of inverter 1074. The signal input to inverter 1074 is the output of NOR Gate 1072. NOR Gate 1072 has three inputs, BC1 signal 889, having a logic "1" value; BC2 signal 891 having a logic "0" value; and BC3 signal 895 having a logic "0" signal at a 12.7 ms. count. The output of NOR Gate 1072 is a logic "0" value, which is input to inverter 1074. The inverter provides the compliment of the input signal as an output, so, a logic "1" value is output from inverter 1074 and input to NAND Gate 1160. Both inputs to NAND Gate 1160 have a logic "1" value, so, the output is a logic "0" value, which is input to NAND Gate 1162 as a first input.

The inputs to NAND Gate 1166 are B1 signal 710, which has a logic "0" value at TCB0, and the output of OR Gate 1164. The inputs to OR Gate 1164 are BC3 signal 895, BC4 signal 897 and BC5 signal 885, which all have a logic "0" value at the 12.7 ms. count. Therefore, the output of OR Gate 1164 is a logic "0" value. The inputs to NAND Gate 1166 are both logic "0" values, so, the output is a logic "1" value, which is input NAND Gate 1162 as the second input.

The inputs to NAND Gate 1146 are the output of OR Gates 1144 and 1142. The inputs to OR Gate 1144 are B2 signal 712 and B3 signal 714 which both have a logic "0" value at TCB0, so, the output of that Gate is at logic "0" value which is input to NAND Gate 1146 as the first input.

The inputs to OR Gate 1142 are BC8 signal 836, having a logic "0" value at the 12.7 ms. count, BC7 signal 830, having a logic "0" value at the 12.7 ms. count, and the output of AND Gate 1140. The inputs to AND Gate 1140 are BC6 signal 893 having a logic "0" value at 12.7 ms. and the output of OR Gate 1138. The inputs to OR Gate 1138 are BC5 signal 885, having a logic "0" value at the 12.7 ms. count, and BC4 signal 897, having a logic "0" value at the 12.7 ms. count. The inputs to OR Gate 1138 are logic "0" values, so the output of that Gate is a logic "0" value, which is input as the second input to AND Gate 1140.

The inputs to AND Gate 1140 are both logic "0" values, so, the output of AND Gate 1140 is a logic "0" value, which is input to OR Gate 1142 as the third input. Since all of the inputs to OR Gate 1142 are logic "0" values, the output is a logic "0" value, which is input to NAND Gate 1146 as the second input. With both inputs to NAND Gate 1146 being logic "0" values, the output of that Gate is a logic "1" value, which is input to NAND Gate 1162 as its third input.

The inputs to NAND Gate 1162 are two logic "1" values and a logic "0" value, so the output logic value of that Gate is a logic "1" value, which is input to as the fourth input to NAND Gate 1158.

The inputs to NAND Gate 1158 are, a first input of a logic "1" value from the output of NAND Gate 1156, a second input of a logic "1" value from the output of NOR Gate 1064, a third input of a logic "1" value from the output of NOR Gate 1094 and a fourth input of a logic "1" value from the output of NAND Gate 1162. Since all of the inputs have a logic "1" value, the output of NAND Gate 1158 is a logic "0" value, which is input to NAND Gate 1186 as the third input.

The first input to NAND Gate 1186 is the output of NOR Gate 1182. There are three inputs to NOR Gate 1182. The first is the output from AND Gate 1178 which AND Gate has inputs of B0 signal 708, having a logic "1" value, and BC3 signal 895 having a logic "0" value at the 12.7 ms. count. So, the output of AND Gate 1178 is a logic "0" value. The second input to NOR Gate 1182 is the output of AND Gate 1180. The inputs to AND Gate 1180 are B1 signal 710, which has logic "0" values at TCB0, BC5 signal 885, and BC3 signal 895, which both have a logic "0" value at the 12.7 ms. count. Therefore, the output of AND Gate 1180 is a logic "0" value, which is input as the second input to NOR Gate 1182.

The third input to NOR Gate 1182 is generated from AND Gates 1168 and 1170; NOR Gate 1172; OR Gate 1174 and inverter 1176. The inputs to AND Gate 1168 are B2 signal 712, having a logic "0" value at TCB0; BC7 signal 830, BC6 signal 893, and BC4 signal 897, which all have logic "0" values at the 12.7 ms. count. All of the inputs to AND Gate 1168 are logic "0" values, so, the output of the Gate is a logic "0" value, which is input to NOR Gate 1172 as a first input.

The inputs to AND Gate 1170 are B3 signal 714 which has a logic "0" value, as described; BC8 signal 836 and BC5 signal 885 each having logic "0" values as described. Therefore, the output of AND Gate 1170 is a logic "0" value, which is input to NOR Gate 1172 as the second input.

Both inputs to NOR Gate 1172 are logic "0" values, so, the output of that Gate is a logic "1" value which is input to OR Gate 1174 as a first input. The second input to OR Gate 1174 is TR signal 844, which has a logic "0" value, as previously described.

The inputs to OR Gate 1174 are a logic "1" value and a logic "0" value, so, the output is a logic "1" value, which is input to inverter 1176, which provides as an output the compliment of the input. Therefore, a logic "0" value is output from inverter 1176 and this value is input to NOR Gate 1182 as the third input.

All of the inputs to NOR Gate 1182 are logic "0" values, so, the output is a logic "1" value which is input to NAND Gate 1186 as the first input.

The second input to NAND Gate 1186 is the output of NAND Gate 1184. The inputs to NAND Gate 1184 are BC8 signal 836, BC5 signal 885, BC4 signal 897 and BC3 signal 895 which all have logic "0" values at the 12.7 ms. count. Since all of the inputs to NAND Gate 1184 have a logic "0" value, the output of that Gate is a logic "1" value, which is input to NAND Gate 1186 as the second input.

The fourth input to NAND Gate 1186 is the output of NAND Gate 1152. The inputs to that Gate are ASYN-CAT signal 1150 which has a logic "0" value and the output of NAND Gate 1146 after passing through inverter 1148, so, the second input to NAND Gate 1152 is a logic "0" value. Since both inputs are logic "0" values, the output of NAND Gate 1152 is a logic "1" value, which is input to NAND Gate 1186 as the fourth input.

As described the first, second, and fourth inputs to NAND Gate 1186 are logic "1" values and the third input is a logic "0" value. Since one input is a logic "0" value the output of NAND Gate 1186 is a logic "1" value, which is TCBS signal 702. This TCBS signal, indicating terminal count TCB0, will cause the State to change from B0 to B1 in the PGSL. However, the count on the UP counters of the B timer will continue throughout the duty cycle.

Following the B0 State, the B1 State is initiated. This state is the AV delay period. As indicated for purposes of example an A-V delay of 215 ms. was chosen. The count on the counter will be such that BC5 signal 887 and BC1 signal 889 will assume logic "1" values. When the count on the timer reaches 215 ms., the output of NAND Gate 1186 will be a logic "1" value indicating TCBS signal 702 has reached a terminal count for the B1 State. The same is true for State B2 or B3, however, when the terminal count is reached on the counter it will be the end of the duty cycle of the B timer.

Referring to FIG. 20A and B, the B timer also generates SHPVER signal 828 used to determine whether a shortened period for testing for verified P-waves is to be used (FIG. 15). SHPVER signal 828 is the output of NOR Gate 964. The inputs to NOR Gate 964 are $\overline{AV2P}$ signal 861, AV3P signal 871 and $\overline{SA0}$ signal 452. When the A timer is in State A1 and the AV delay is less than 100 ms., $\overline{SA0}$ has a logic "0" value, $\overline{AV2P}$ has a logic "0" value and AV3P has a logic "0" value. This will cause NOR Gate 964 to have a logic "1" output, which is SHPVER signal 828 for shortening the P verification sample period from 101.6 ms. to 50.8 ms.

FURTHER C-TIMER DESCRIPTION

The C timer logic circuitry is generally shown at 1190 in FIG. 21 A. The C timer is used for timing out the absolute refractory period, relative refractory period and the maximum track rate for the apparatus. This timer is also used for determining the length of the atrial refractory period which can be set to C1; or C1+C2; or C1+C2+C3. These parameters are stored in memory and accessed by the C timer. The C timer is a continuous timer. C0 is the holding state for the C timer when not in States C1, C2 or C3. The C1 State is the absolute refractory period and is fixed at 150 ms. The C2 State is the relative refractory period which is programmable 250, 325, 394 or 470 ms. State C3 is the maximum tracking which is programmable to 90, 110, 130 or 150 ppm. Maximum tracking guarantees that no TRV will follow another or follow a valid "R" wave by less than the programmed interval of the C3 State.

For purposes of description, an absolute refractory period of 150 ms., a relative refractory period of 325 ms., and a maximum tracking of 90 ppm. or 666 ms. will be used to describe the logic circuits of the C timer. The following table indicates the logic values for the relative refractory period and maximum tracking parameters.

TABLE 6A

| Parameter | Logic Value |
|---|---|
| MRR-0 | 1 |
| MRR-1 | 0 |
| MMTR-0 | 1 |
| MMTR-1 | 1 |

The above logic values are input from memory to C timer. These values are input as MRR-1 signal 1192, MMTR-1 signal 1194, MRR-0 signal 1198, and MMTR-0 signal 1200. The control signals for MUX 1208 are SC0 signal 626 and SC1 signal 628.

The C timer has MUX switches 1226, 1228, 1230, 1232, 1234, 1236 and 1238 which are for determining the logic sequence for reaching a terminal count on the timer. The respective MUX switch outputs are determined by their control signals. These control signals are the X output of MUX 1208, the output of XOR Gate 1212 and SC1 signal 628.

The respective MUX provide outputs to respective XOR Gates 1240, 1242, 1244, 1248, 1250 and 1252 as first inputs. The second inputs to these XOR Gates are the respective outputs of 7 bit binary counter 1224. These inputs combined with the remainder of the circuitry to provide the appropriate terminal counts of the C timer.

Assuming the logic values in memory in Table 6 above, a description of the logic circuitry will follow using these values. Further, for example purposes, the C timer is in State C1 and the change of state to C2 will be described when a TCC1 has been reached to describe the operation of the C timer logic circuitry.

Once MUX 1208 is loaded with the above state logic values, the timer is ready to count out the C States when required. When there has been a TRV or IRW, the C counter will be reset by CRST signal 624 having a logic "1" value. Simultaneous with this, the C1 State will be initiated and SC1 signal 628 will have a logic "0" value and SC0 signal 626 will have a logic "1" value. Since the absolute refractory period has a value of 150 ms., this period will time out in 24 clock periods. When 150 ms. have passed, the Q5, and Q4 outputs of binary counter 1224 will assume a logic "1" values, which are input to XOR Gate 1244, and XOR Gate 1246 as second inputs, respectively.

The first input to XOR Gate 1244 is the output of MUX 1230. In State C1 at TCC1, SC0 signal 626 has a logic "1" value and SC1 signal 628 has a logic "0" value. These signals are input to the control inputs of MUX 1208. These control signals cause the two grounded inputs to MUX 1208 to be output from the X and Y outputs of the MUX, respectively. The X output having a logic "0" value is input to the seven MUX switches as the first control signal.

The second control signal for the seven MUX switches is the output of XOR Gate 1212. The inputs to that Gate are SC1 signal 628 and SC0 signal 626. Since these signals have different logic values, the output of XOR Gate 1212 is a logic "1" value, which is input as the second control signal for the MUX switches.

The third control signal is SC1 signal 628. The logic value of this signal is a logic "0" value in State C1 at TCC1.

When the control signals having the above described logic values are input to MUX switches 1226, 1228, 1230, 1232, 1234, 1236 and 1238, the X2 input logic value is output from each MUX.

For MUX 1230 the X2 input is connected to $V_{dd}$, so, the logic value output from that MUX is a logic "1" value. This value is input to XOR Gate 1244 as the first input.

Both inputs to XOR Gate 1244 are logic "1" values so the output logic value of XOR Gate 1246 is a logic "0" value, which is input to NOR Gate 1254 as a third input.

The first input to NOR Gate 1254 is the output of XOR Gate 1240. The inputs to XOR Gate 1240 are the output of MUX 1226 and the Q7 output of counter 1224. The X2 input is grounded so the output logic value is a logic "0" value, which is the first input to XOR Gate 1240. The Q7 output of binary counter 1224 is a logic "0" value at 150 ms. Since both inputs are a logic "0" value, the output is a logic "0" value which is input to NOR Gate 1254 as the first input.

The second input to NOR Gate 1254 is the output of XOR Gate 1242. The inputs to that Gate are the Q6 output of binary counter 1224, which is a logic "0" value at 150 ms. and the X2 input from MUX 1228. The X2 input is grounded, so it has a logic "0" value. Since both inputs are logic "0" values, the output of XOR Gate 1242 is a logic "0" value which is input as the second input to NOR Gate 1254.

All of the inputs to NOR Gate 1254 are logic "0" values, so, the output of that Gate is a logic "1" value which is input to NAND Gate 1256 as a first input. The second input to NAND Gate 1256 is the output of NOR Gate 1255. The inputs to NOR Gate 1255 are the output of XOR Gates 1246, 1248, 1250 and 1252.

The inputs to XOR Gate 1246 are the X2 input to MUX 1232, which is a logic "1" value, and the Q4 output of binary counter 1224, which is a logic "1" value at 150 ms. The output of XOR Gate 1246 is therefore a logic "0" value, which is input to NOR Gate 1255 as the first input.

The second input to NOR Gate 1255 is output of XOR Gate 1248. The inputs to that Gate are the X2 input, which has a logic "0" value; and the Q3 output of binary counter 1224, which has a logic "0" value at 150 ms. Since both inputs to XOR Gate 1248 are logic "0" values, the output is a logic "0" value, which is input to NOR Gate 1255 as the second input.

The third input to NOR Gate 1255 is the output of XOR Gate 1250. The inputs to that Gate are the output of MUX 1236 and the Q2 output of binary counter 1224, which is a logic "0" value at 150 ms. The output of MUX 1250 is the X2 input to that MUX, which is connected to the Y output of MUX 1208 having a logic "0" value. Both inputs to NOR Gate 1250 are logic "0" values, so the output of that Gate is a logic "0" value, which is input as the third input to NOR Gate 1255.

The fourth input to NOR Gate 1255 is the output of XOR Gate 1252. The inputs to that Gate are the output of MUX 1238 and the Q1 output of binary counter 1224, which has a logic "0" value at 150 ms. The output of MUX 1238 has the logic value of the X2 input, which is connected to the Y output of MUX 1208. This logic value is a logic "0" value. Since both of the inputs to XOR Gate 1252 are logic "0" values, the output of that Gate is a logic "0" value, which is input to NOR Gate 1255 as the fourth input.

All of the inputs to NOR Gate 1255 are logic "0" values, so, the output is a logic "1" value which is input to NAND Gate 1256 as the second input. Both inputs to NAND Gate 1256 are logic "1" values, so, the output is a logic "0" value, which is input to NAND Gate 1260 as a first input.

The second input to NAND Gate 1260 is the output of NAND Gate 1258. The inputs to NAND Gate are the Q5, Q6 and Q7 outputs of binary counter 1224 representing 16, 32 and 64 clock periods for a total of 112 clock periods. When this number of clock periods (or 711.20 ms.) have passed since resetting of the timer, all of the inputs will assume a logic "1" value. At that time, the output of NAND Gate 1258 will assume a logic "0" value which will be input to NAND Gate 1260 to cause TCC signal 632 to assume a logic "1" value indicative of the maximum time out of the C timer. At all other times, the output of NAND Gate 1258 will have a logic "1" value.

When the C timer has timed out for 150 ms., while in State C1, the inputs to NAND Gate 1260 are a logic "0" value and a logic "1" value. This will cause the output of NAND Gate 1260 to assume a logic "1" value for TCC signal 632 indicative of a terminal count of State C1, TCC1. This logic "1" value is input to the PGSL, to change the C State. This same process of generating a terminal count is utilized for generating a terminal count for the C2 State, the relative refractory period, the C3 State, and the maximum tracking rate.

Again referring to FIG. 21A, the C timer also generates ATREF signal 326 used in the DDX modality. The logic gates for generating the ATREF signal are AND Gates 1214 and 1216; NOR Gate 1217 and inverter 1220. ATREF signal 326 will have a logic "1" value output, when AND Gate 1214 has a logic "1" value output or when AND Gate 1216 has a logic "1" value output. First AND Gate 1214 will be discussed and then AND Gate 1216. The following table sets forth the period of atrial refractory:

TABLE 7

| MAR-1 | MAR-0 | Atrial Refractory Period |
|---|---|---|
| 0 | 0 | C1 |
| 0 | 1 | C1 + C2 |
| 1 | 0 | C1 + C2 + C3 |

TABLE 7-continued

| MAR-1 | MAR-0 | Atrial Refractory Period |
|-------|-------|--------------------------|
| 1     | 1     | C1 + C2 + C3             |

The inputs to AND Gate 1214 are SC0 signal 626 and MAR-0 signal 1202. In order for this Gate to assume a logic "1" value output, both SC0 signal 626 and MAR-0 signal 1202 must have a logic "1" value. SC0 signal 626 assumes a logic "1" value only during the C1 and C2 States. MAR-0 signal 1202 has a logic "1" value as indicated in Table 7. For purposes of example, it will be assumed that MAR-0 signal 1202 is a logic "0" value and MAR-1 signal 1196 is a logic "1" value meaning the atrial refractory period is C1+C2+C3.

At TCC1, SC0 signal 626 has a logic "0" value which is input to AND Gate 1214 as a first input. MAR-0 signal 1202 has a logic "0" value as indicated, so the output of AND Gate 1214 is a logic "0" value which is input to NOR Gate 1217 as a first input. The inputs to AND Gate 1216 are MAR-1 signal 1196 and $\overline{C0}$ signal 636. The output of AND Gate 1216 will assume a logic "1" value when both inputs are a logic "1" value. MAR-1 signal has a logic "1" value, as indicated in Table 7. $\overline{C0}$ signal will assume a logic "1" value when the C timer is in C States C1, C2 or C3. Since the C timer is at TCC1, the logic value of $\overline{C0}$ signal 636 is a logic "1" value. Since the inputs to AND Gate 1216 are both logic "1" values the output is a logic "1" value, which in input to NOR Gate 1217 as the second input. Since the inputs to NOR Gate 1217 are a logic "0" value and a logic "1" value, the output of that gate is a logic "0" value which is input to inverter 1220. The compliment of the input is output from inverter 1220, so, a logic "1" value ATREF signal 326 is output from the inverter. This will mean ATREF signal 326 will have a logic "1" value for States C1, C2 and C3.

MARKER CHANNELS

The novel marker channels are used to telemeter from the apparatus specific events which take place in the heart as viewed by the apparatus. The markers assist in determining when the antitachycardia modalities will interact with the apparatus to put out a stimulating pulse to break the tachycardia.

Figure 22:
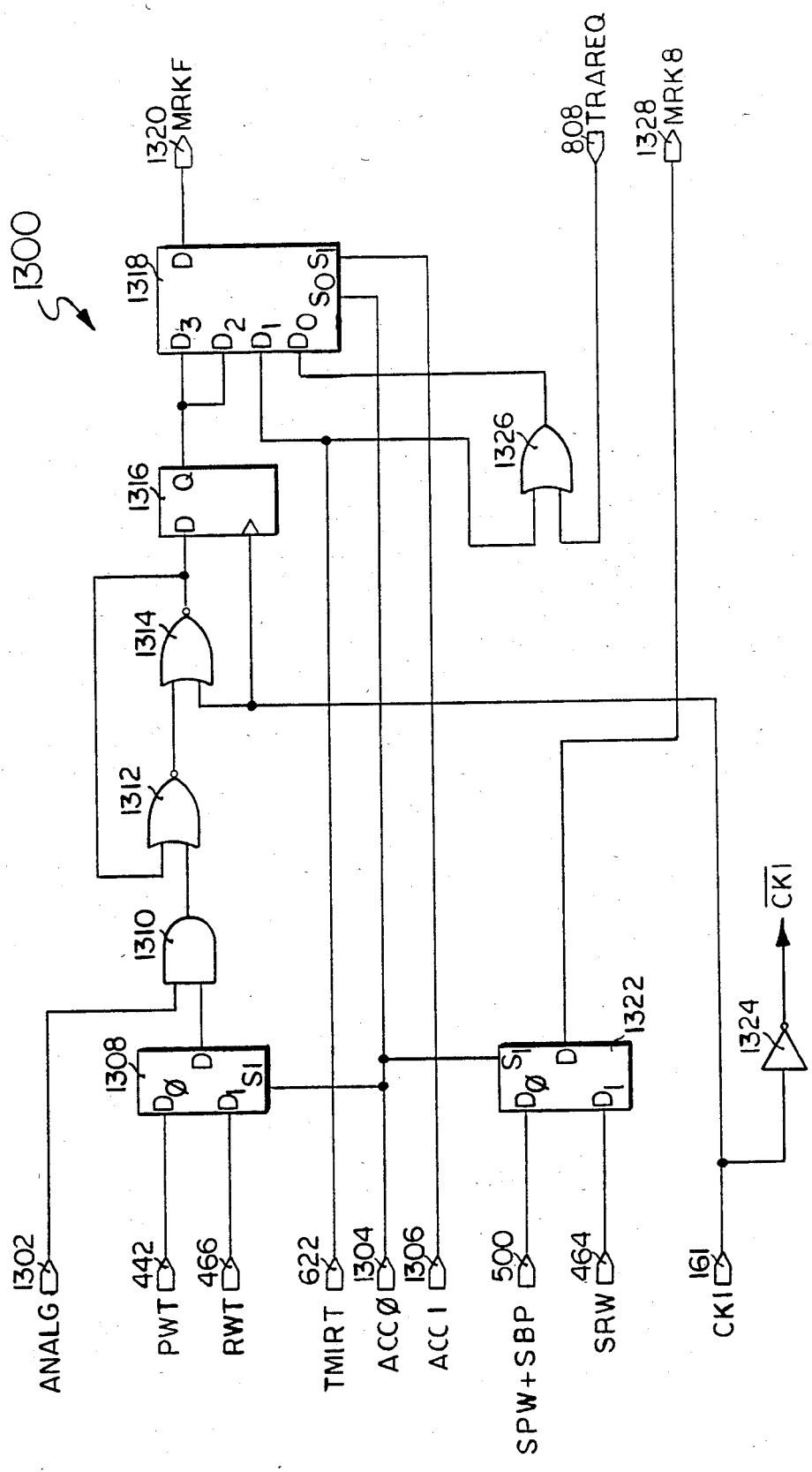
FIG. 22 shows the logic for generation of Markers F and 8.

Referring to FIG. 22, the specific markers, MRK 8 signal, 1328 and MRK F signal, 1320 are generated. The distinction between MRK 8 signal 1328 and MRK F signal 1320 is that the amplitude of MRK F telemetered signals is $V_{dd}$ and the amplitude of a MRK 8 telemetered signals is $V_{REF}$, which is $\frac{1}{3}$ the amplitude of $V_{dd}$.

The marker events themselves are also distinguishable by their duration, as indicated in Table 8, which table sets forth the signals telemetered from the stimulator via the marker channels.

TABLE 8

| Marker Channel | Signal | Amplitude | Duration |
|---|---|---|---|
| I. Section 8 | | | |
| MRK 8 | IPW | $V_{REF}$ | <100 ms. |
| MRK 8 | SBP | $V_{REF}$ | >100 ms. |
| MRK F | TRA | $V_{dd}$ | 6.35 ms. |
| MRK F | TRV | $V_{dd}$ | 19.05 ms. |
| MRK F | IRW | $V_{dd}$ | 12.7 ms. |
| II. Section 9 | | | |
| MRK F | TRA/TRV | $V_{dd}$ | 19.05 ms. |
| MRK F | IRW/IPW | $V_{dd}$ | 12.7 ms. |
| MRK 8 | R-WAVE NOISE | $V_{REF}$ | Continuous until TCA2 or end of pacer cycle |

TABLE 8-continued

| Marker Channel | Signal | Amplitude | Duration |
|---|---|---|---|

The duration of the telemetered marker signals is dependent on the A, B, C timers and the PGSL logic circuitry. The output chip logic (not shown) determines the amplitude of the signal output by the apparatus indicative of the signals shown in Table 8. During portions of analog telemetry of which markers are a part as will be described, the apparatus paces asynchronously.

Referring to FIGS. 22, 23, 24, 25 and 26, generally shown at 1300, 1350, 1450, 1500 and 1540, respectively, the novel marker channels will be described.

These are two discrete analog sequences which are telemetered from the apparatus. The first involves Sections 1 through 8 of analog telemetry and the second are Sections 9 through F of analog telemetry. The apparatus paces asynchronously during Section 1–7. Markers are associated with section 8, 9, A, B, C and D of analog telemetry (C and D are for ECG telemetry). This telemetering is controlled by the analog counter shown in FIG. 23, which will be described subsequently.

Referring to FIG. 22, there are three MUXs responsible for the input of R and P channel signals. MUX 1308 has PWT signal 442 and RWT signal 466 input to the $D_0$ and $D_1$ inputs, respectively. MUX 1322 has SPW+SBP signal 500 and SRW signal 464 input to the $D_0$ and $D_1$ inputs, respectively. MUX 1318 receives inputs from flip-flop 1316, OR Gate 1326 and TMIRT signal 622. The control signal for determining which input will be output from the respective MUX is ACC0 signal 1304 and ACC1 1306. These signals are the output of flip-flop 1374 and flip-flop 1376, respectively (FIG. 23) and will be described subsequently.

The two input signals to MUX 1308 are generated from FIG. 9A upon sensed activity on the P or R channel.

ACC0 signal 1304 has a logic "0" value until the Section 1-8 analog sequence is entered. So, the $D_0$ input is output by the MUX. However, ACC0 signal 1304 will have a logic "1" value as soon as the analog sequence is commenced which will output the $D_1$ input from the MUX. The control of analog telemetry of the marker channels is caused by a specific command to the apparatus in the form of a RF data signal transmitted from an external device (not shown).

The generation of the MRK F signal 1320 will be disclosed first, then the generation of MRK 8 signal 808 will be disclosed.

The logic gates used to generate MRK F signal 1320 are MUX 1308, AND Gate 1310, NOR Gates 1312 and 1314, flip-flop 1316, OR Gate 1326 and MUX 1318. The logic gate used to generate MRK 8 signal 1328 is MUX 1322.

AND Gate 1310 has two inputs. The first is ANALG signal 1302 and the second is the output of MUX 1308. The output from MUX 1308 is determined by ACC0 signal 1304.

For purposes of explaining the operation of the logic circuitry it is initially assumed that an R-wave has been sensed. Therefore, upon the sensing of an R-wave, the logic "1" value for RWT signal 466 is output from MUX 1308 only when ACC0 signal 1304 has a logic "1" value. For marking to take place the apparatus must be in marker Section 9, because marker Section 1 is for analog measurements and not marking. This logic "1" value is input to AND Gate 1310. The output of AND Gate 1310 will have a logic "1" value when ANALG signal 1302 also has a logic "1" value. This output is input to the latch comprising of NOR Gates 1312 and 1314.

The logic "1" value input to NOR Gate 1312 will cause the output to assume a logic "0" value regardless of the logic value of the other input. The second input to NOR Gate 1312 is the feedback from the output of NOR Gate 1314 which initially has a logic "0" value.

The output of NOR Gate 1312 having a logic "0" value is input to NOR Gate 1314 as a first input. The second input to NOR Gate 1314 is the CK1 signal 161. On the negative edge of the CK1 signal the output of NOR Gate 1314 will assume a logic "1" value which is input to the D input of flip-flop 1316.

On the next clock pulse, the logic "1" value into the D input flip-flop 1316, is output from the Q output of that flip-flop. This logic "1" value is then input to the $D_2$ and $D_3$ inputs of MUX 1318.

The input to the $D_1$ input to MUX 1318 is TMIRT signal 662. TMIRT signal 622 is generated in FIG. 12. Various signals are input MUX 1318 via TMIRT signal 622 through the $D_1$ and $D_0$ input to the MUX. All of these signals will be described in the following text.

Referring to FIG. 12, when IRW+TRVD signal 572 has a logic "1" value, because of a logic "1" value IRW signal, this logic value is input to the D input of flip-flop 608. On the next clock, the $\overline{Q}$ output will assume a logic "0" value, which is input to NAND Gate 612, causing its output to assume a logic "1" value. Also, during the clocking of flip-flop 608, the logic "1" value output from the Q output of that flip-flop is input to the D input of flip-flop 610. On the next clock, the $\overline{Q}$ output of flip-flop 610 assumes a logic "1" value and the $\overline{Q}$ output of flip-flop 610 assumes a logic "0" value. Therefore, TMIRT signal 622 will remain a logic "1" value for 12.7 ms. or 2 clock periods when IRW+TRVD is a logic "1" value because of a logic "1" value IRW signal.

Again referring to FIG. 22, the input to the $D_0$ input to MUX 1318 is the output of OR Gate 1326. The inputs to OR Gate 1326 are TRAREQ signal 808 and TMIRT signal 622. The TRAREQ signal 808 is generated in FIG. 14.

Referring to FIG. 14, the TRAREQ signal 808 is generated from the output of NAND Gate 774. Since the TRA signal will have a logic "1" value for one clock of 6.35 ms., TRAREQ signal 808 will have a logic "1" value for the same amount of time. This logic "1" value is input to OR Gate 1326 as stated and will cause the output of OR Gate 1326 to have a logic "1" value for that period of time. This will be input to the $D_0$ input of MUX 1318.

The TMIRT signal 622 is also an input to OR Gate 1326, as stated. TMIRT signal 622 in this case is used for determining the marker duration of a TRV signal with a logic "1" value.

Referring to FIGS. 12 and 14, the method of generating the duration of the TRV signal will be described. One clock prior to the clocking of a TRV signal, the logic "1" value output NAND Gate 766, which is TRVD signal 807, is input to OR Gate 654 (FIG. 13) causing its output to assume a logic "1" value. This output is IRW+TRVD signal 572, which is input to the D input of flip-flop 608. On the next clock, the $\overline{Q}$ output flip-flop 608 assumes a logic "0" value which is input to NAND Gate 612 causing its output to assume a logic "1" value. Also, the Q output of flip-flop 608, having a logic "1" value is input to the D input of flip-flop 610.

Referring to FIG. 14, when flip-flop 768 is clocked under these conditions, the Q output of the flip-flop assumes a logic "1" value which is input to the D input of flip-flop 792.

On the next clock, the $\overline{Q}$ of flip-flop 610 (FIG. 12) will assume a logic "0" value and will cause the output of NAND Gate 612 to remain at a logic "1" value. Simultaneous with this clock, the Q of flip-flop 792 outputs a logic "1" value which is input to the D input of flip-flop 794. On the next clock, the $\overline{Q}$ output, signal 574, of flip-flop 794 assumes a logic "0" value, which is input to NAND Gate 612. This logic "0" value maintains the output of NAND Gate 612 at a logic "1" value. However, on the next clock the logic "0" value is cleared out and all of the inputs to NAND Gate 612 are logic "1" values. So, for marker purposes the TMIRT signal for a TRV has a logic "1" value for 19.05 ms. or 3 clocks. This will be input to MUX 1318 through OR Gate 1326 and the $D_0$ input.

The control signals which determines which of the inputs are output from MUX 1318 are ACC0 signal 1304 and ACC1 signal 1306. The generation of these signals will be described in the following text.

Figure 23:
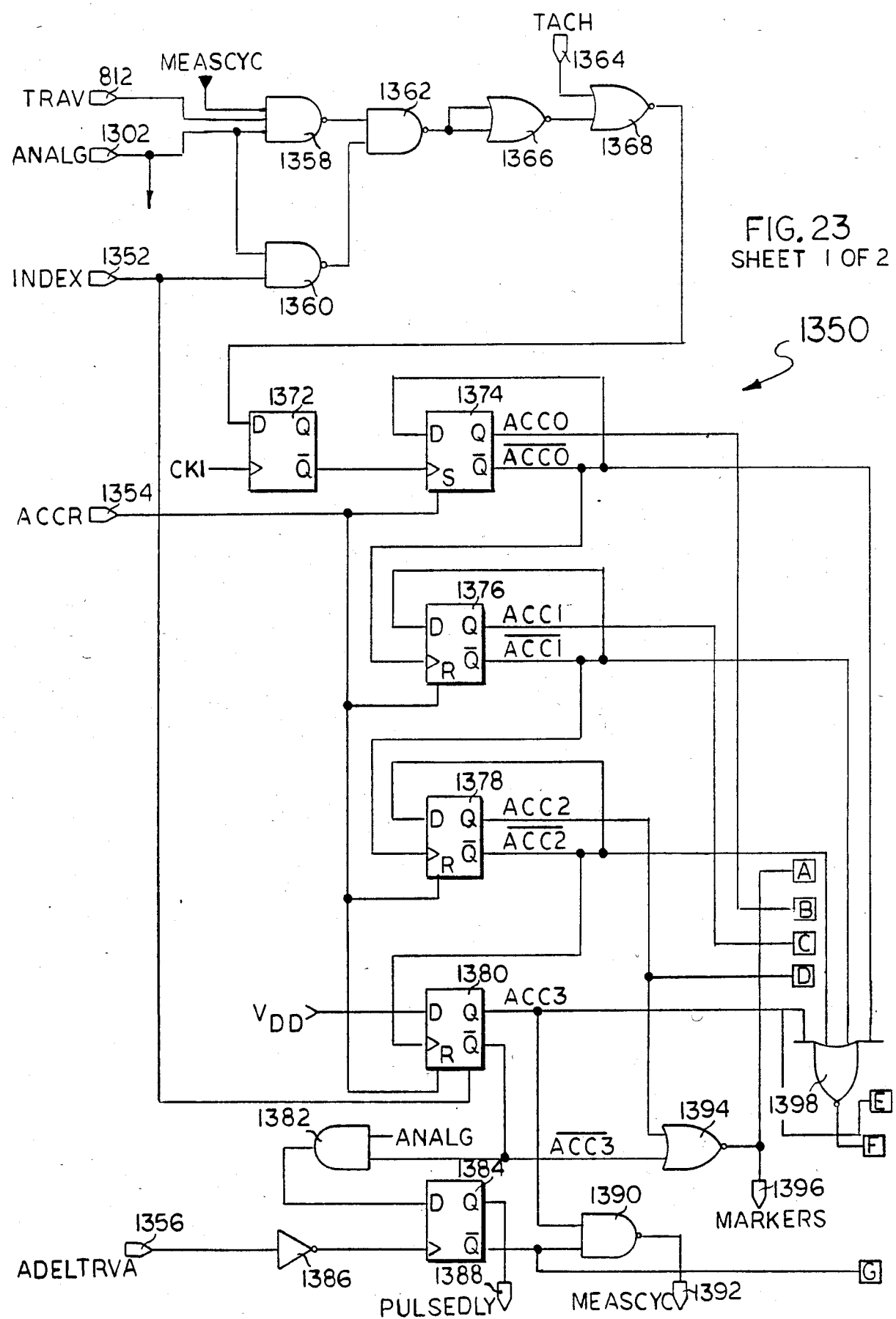
FIG. 23 shows the logic for the analog section counter.
Figure 23:
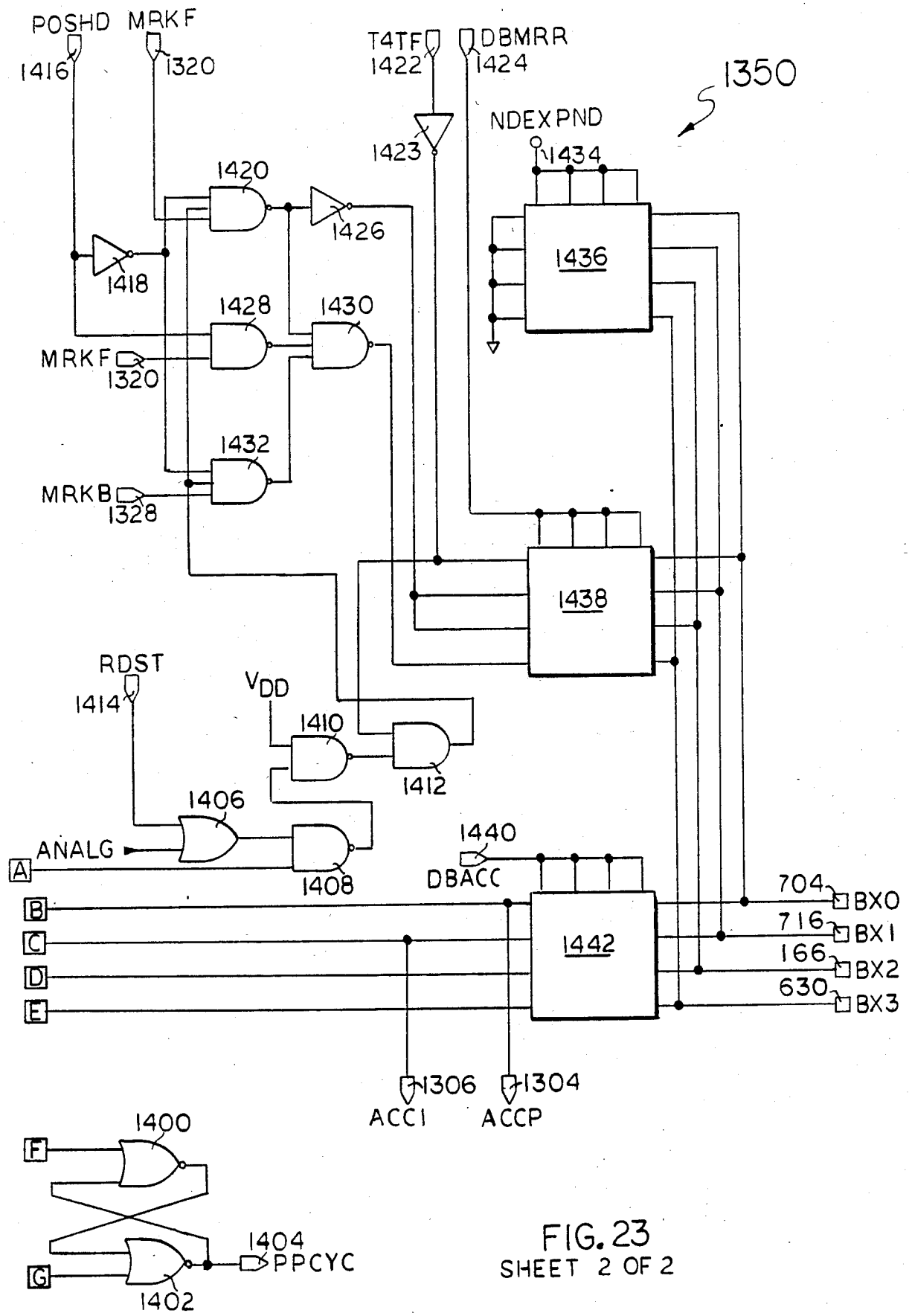

Referring to FIG. 23, the analog counter logic section of communications State Sequencer 8 (FIG. 1) is shown generally at 1350. When ANALG signal 1302 has a logic "1" value, analog telemetry is commanded. This ANALG signal is input to NAND Gates 1358 and 1360.

Taking first NAND Gate 1360, it has one input other than ANALG signal 1302. This input is INDEX signal 1352. The INDEX signal is used to index the counter through analog sections 9, A, B, C, D, E, F and wrap the counter around Section 8. The description will first be limited to Sections 1–8 of analog telemetry then sections 9–F.

INDEX signal 1352 has a logic "0" value when in sections 1–8, which when input to NAND Gate 1360 will cause its output to assume a logic "1" value, regardless of the logic value of ANALG signal 1302. This logic "0" value output is input as the first input to NAND Gate 1362.

The second input to NAND Gate 1362 is the output of NAND Gate 1358. As described, the first input is the ANALG signal with a logic "1" value. The second input is TRAV signal 812 generated in FIG. 14. This signal will have a logic "1" value on the clocking of a logic "1" value TRA or TRV signal. The third signal is the MEASCYC signal 1391, which is the output of NAND Gate 1390.

NAND Gate 1390 has two inputs. These inputs are the Q output of flip-flop 1380 and the $\overline{Q}$ output of flip-flop 1384. The D input to flip-flop 1384 is loaded with the output of AND Gate 1382. The inputs to AND Gate 1382 are ANALG signal 1302 having a logic "1" value, as stated, and the $\overline{Q}$ output of flip-flop 1380. The $\overline{Q}$ output of flip-flop 1380, which is the second input to AND Gate 1382 has a logic "1" value. At the beginning of the analog telemetry cycle, ACCR signal 1354 will reset the analog counter flip-flops 1376, 1378 and 1380. So, the $\overline{Q}$ output of flip-flop 1380 will assume a logic "1" value. Since both inputs to AND Gate 1382 are logic "1" values, the output is a logic "1" value which is input to the D input of flip-flop 1384. Until flip-flop 1384 is clocked by the $\overline{\text{ADELTRVA}}$ signal the Q output assumes a logic "0" value and the $\overline{Q}$ output assumes a logic "1" value.

The signal which clocks flip-flop 1384 is $\overline{ADELT}$ $\overline{RVA}$ signal 1356 after it passes through inverter 1386. The logic circuitry for the generation of the signal is shown in FIG. 24.

Figure 24:
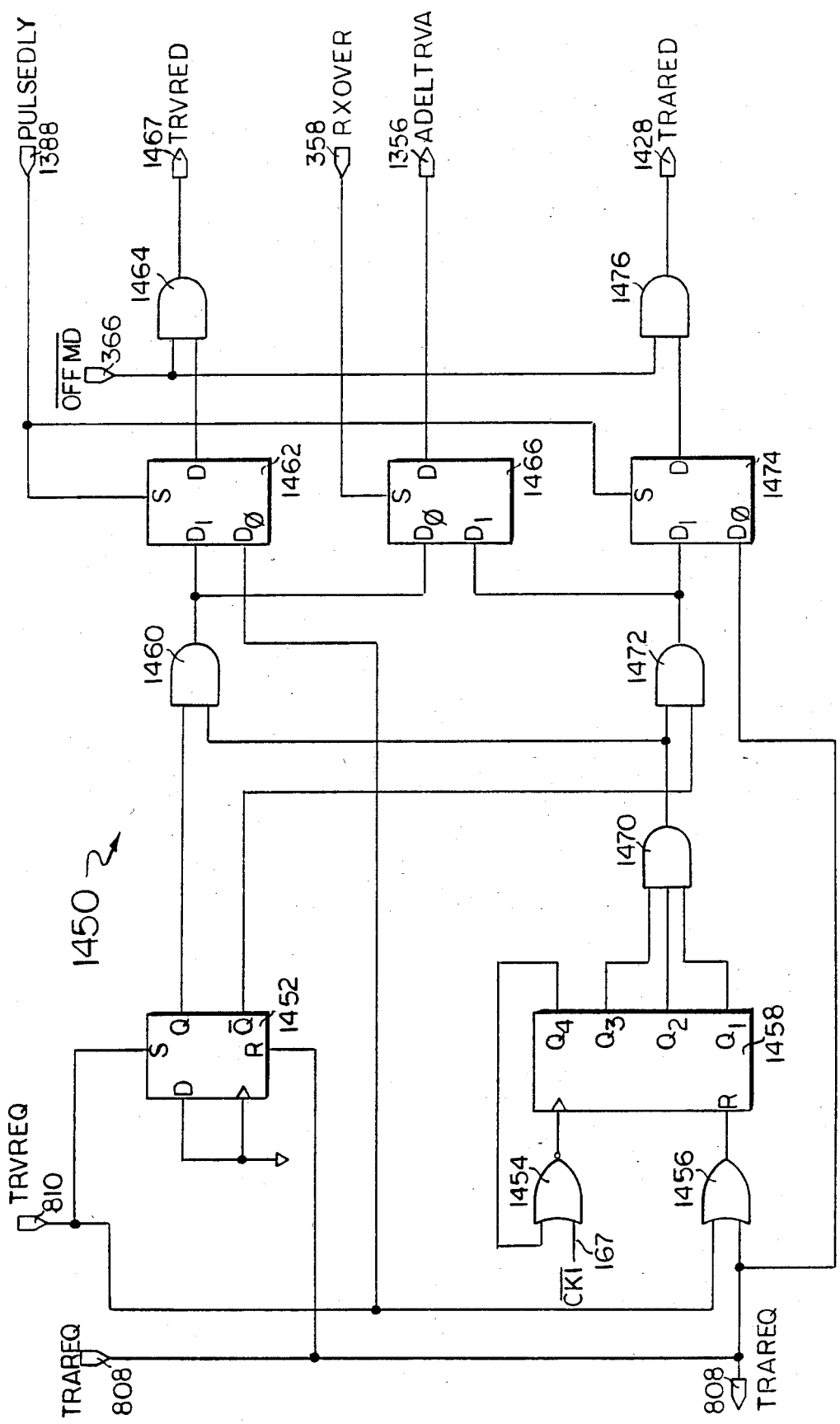
FIG. 24 shows the logic for generation of the ADELTRVA signal for use in FIG. 23.

Referring to FIG. 24, ADELTRVA signal 1356 is output from MUX 1466. First the logic circuitry will be described in regard to TRVREQ signal 810 having a logic "1" value and then TRAREQ signal 808 having a logic "1" value.

When TRVREQ signal 810 has a logic "1" value, it will set flip-flop 1452. Once set, the Q output of flip-flop 1452 will assume a logic "1" value and the $\overline{Q}$ output a logic "0" value. The Q output of flip-flop 1452 is input to AND Gate 1460 as a first input. The second input to AND Gate 1460 is the output AND Gate 1470. The gates that determine the output of AND Gate 1470 are OR Gates 1456, NOR Gates 1454 and binary counter 1458.

At the point in the pacer cycle when TRVREQ signal 810 has a logic "1" value, TRAREQ signal 808 normally has a logic "0" value so a "0" value will be assumed. Therefore, inputs to OR Gate 1456 are a logic "1" value and a logic "0" value. Since at least one of the inputs has a logic "1" value, the output of OR Gate 1456 is a logic "1" value which resets binary counter 1458. Therefore, on every TRAREQ signal 800 or TRAREQ signal 810 having a logic "1" value, the output of OR Gate 1456 is a logic "1" value, which resets binary counter 1458.

The signal for clocking the binary counter 1458 is the output of NOR Gate 1454. The inputs to NOR Gate 1454 are $\overline{CK1}$ signal 167 and the feedback signal from the Q4 output of binary counter 1458. Since counter 1458 is a binary counter, the Q4 output will not assume a logic "1" value for 8 clock periods after reset. Until 8 clock periods have been passed, the Q4 output will have a logic "0" value. During the first seven clock periods when the $\overline{Q4}$ output is a logic "0" value, on every positive edge $\overline{CK1}$ signal 167, the output of NOR Gate 1454 will assume a logic "0" value and on the negative edge the output will assume a logic "1" value. Therefore, normal clocking of the binary counter will take place until the eighth clock period after reset, when the Q4 output assumes a logic "1" value, which will hold the output at a logic "0" value. This effectively blocks any additional clocking of the counter until reset.

The three inputs to AND Gate 1470 are the Q1, Q2 and Q3 outputs of binary counter 1458. When each of these outputs have a logic "1" value, AND Gate 1470 has a logic "1" output. Therefore, after seven clock periods the Q1–Q3 outputs will all have logic "1" values which causes AND Gate 1470 to have a logic "1" output for one clock period.

The output of AND Gate 1470 is input to AND Gate 1460. Since both outputs are logic "1" values, the output of AND Gate 1460 is a logic "1" value, which is input to the $D_0$ input of MUX 1466. The signal input to the $D_0$ input will be output from the D output of MUX 1466 unless RXOVER signal 358 has a logic "1" value. When RXOVER signal 358 has a logic "1" value, it will set MUX 1466 and the logic value input to the $D_1$ input will be output from the D output of the MUX. Since it is assumed that one of the atrial modalities is not being used, RXOVER signal 358 has a logic "0" value, so the $D_0$ input is output from MUX 1466 as ADELTRVA signal 1356. Therefore, the ADELTRVA signal will follow 44.45 ms. after generation of the TRV REQ signal.

TRAREQ signal 808 assumes a logic "1" value, when there has been a TRA signal having a logic "1" value or when the TRV has a logic "1" value that was crossed over to the TRAREQ line by RXOVER signal 350 having a logic "1" value. If a TRAREQ signal 808 has a logic "1" value, the output of OR Gate 1456 is a logic value "1" which resets binary counter 1458 as stated and resets flip-flop 1452.

When this takes place, the $\overline{Q}$ output of flip-flop 1452 assumes a logic "1" value and the Q output assumes a logic "0" value. This logic "1" value from the $\overline{Q}$ output is input to AND Gate 1472 as the second input. The first input to AND Gate 1472 is the output of AND Gate 1470, which, as described, will not have a logic "1" value output until 44.45 ms. after MUX 1458.

Once 44.45 ms. has elapsed, AND Gate 1470 has a logic "1" value output, which is input to AND Gate 1472. Since both inputs to AND Gate 1472 are logic "1" values, the output is a logic "1" value which is input to the $D_1$ input of MUX 1466. However, in order for the $D_1$ input to be output from the D output of MUX 1466, the set term RXOVER 358 must have a logic "1" value. In order for RXOVER signal 358 to have a logic "1" value one of the atrial modalities must be programmed. So unless this is the case, TRAREQ 808 will not be used to produce ADELTRVA signal 1356 having a logic "1" value.

Referring to FIG. 23, the ADELTRVA signal 1356 will clock flip-flop 1384 after 50.8 ms., as previously described. This signal is input to inverter 1386 before being input to the clock input of flip-flop 1384. During the first six periods after reset, ADELTRVA signal 1356 has a logic "0" value which provides a logic "1" is input to the clock input of flip-flop 1384 because of inverter 1386. On the seventh clock ADELTRVA signal 1356 assumes a logic "1" value. This means that a logic "0" value is input to the clock input. On the following clock, the logic "0" value will transition to a logic "1" value. So, on the edge of this change the flip-flop is clocked.

Upon clocking of the flip-flop the Q output of this flip-flop assumes a logic "1" value, which is PULSEDLY signal 1388. This signal will delay the output of pulses from the simulator by 50.8 ms. subsequent to a TRA or TRV resulting in a TRAREQ or TRVREQ. This period of 50.8 is for analog telemetry from the apparatus.

The $\overline{Q}$ output of flip-flop 1384 is input to NAND Gate 1390. The other input to NAND Gate 1390 is the Q output of flip-flop 1380. At the beginning of the analog telemetry flip-flop 1380 is reset by ACCR signal 1354. Until the flip-flop is either clocked or set the output logic values of the Q and $\overline{Q}$ output will remain in a reset condition. Therefore, the Q output is a logic "0" value which is input to NOR Gate 1390. The output of NAND Gate 1390 is a logic "1" value, which is MEAS-CYC signal 1392, since the inputs are a logic "1" value and a logic "0" value. The MEASCYC signal 1392 is input to NAND Gate 1358 as its first input.

MEASCYC signal 1392 will have a logic "0" value after 50.8 have passed and flip-flop 1384 has been clocked. This is the only time when both inputs to AND Gate 1390 have logic "1" values. At that point, the Q output of flip-flop 1380 will assume a logic "1" value because the D input to flip-flop 1380 is connected to $V_{dd}$ having a logic "1" value when clocked. The second input, which is $\overline{Q}$ output of flip flop 1384, will be a logic "1" value. On clocking of flip flop 1380, the $\overline{Q}$ output of flip-flop 1380 is a logic "0" value. This means that both inputs to AND Gate 1382 are not logic "1" values so input to the D input of flip-flop 1384 is a logic "0" value. On clocking of flip-flop 1384, the $\overline{Q}$ output will assume a logic "1" value, which is input to NAND Gate 1390. MEASCYC signals 1392 will be a logic "0" value. This takes place only when section 8 is reached or the counter is in Sections 9–F.

Again referring to NAND Gate 1358 and assuming MEASCYC signal 1392 is a logic "1" value, all of the inputs to NAND Gate 1358 have logic "1" values, so the output of that Gate is a logic "0" value which is input to NAND Gate 1362 as the first input. The second input, as previously described is the output of NAND Gate 1360 which has a logic "1" value. Since the inputs to NAND Gate 1362 are a logic "1" value and a logic "0" value, the output is a logic "1" value, which is input to the tied input of NOR Gate 1366. The output logic value of NAND Gate 1362 is a logic "1" value, the output of NOR Gate 1366 is a logic "0" value, which is input to NOR Gate 1368 as the second input.

The first input is TACH signal 1364. Since one of the anti-tachycardia modalities are not being used, TACH signal 1364 has a logic "0" value. Both inputs to NOR Gate 1368 are logic "0" values, so the output is a logic "1" value which is input to the D input of flip-flop 1372 which initiates clocking of the analog counter flip-flops.

The signal which normally causes clocking of the analog counter is TRAV signal 812 which has a logic "1" value every pacer cycle because the pacer paces asynchronously in this part of the telemetry sequence. On each logic "1" value of TRAV signal 812, once MEASCYC signal assumes a logic "1" value in Section 8, the output of NAND Gate 1358 will assume a logic "0" value. This logic "0" value is input to NAND Gate 1362 causing its output to assume a logic "1" value. This logic "1" value is input to the tied inputs of NOR Gate 1366 causing its output to assume a logic "0" value, which is input to NOR Gate 1368 as the second input. The first input is TACH signal 1364 which has a logic "0" value, so the output of NOR Gate 1368 is a logic "1" value, which is input to the D input of flip flop 1372. On the first clock after TRAV signal 812 has a logic "1" value, the Q output of flip-flop 1372 assumes a logic "1" value. This logic value is input to the clock input of flip-flop 1374. It is to be noted that for the analog count the ACC0 signal is the LSB and the ACC3 signal is the MSB. Since ACCR signal 1354 sets flip-flop 1374 and resets flip-flops 1376, 1378 and 1380 at the end of each cycle, the counter counts from Section 1.

On the clocking of flip-flop 1372, the Q output of that flip-flop is a logic "1" value as stated. On the positive edge of the change from logic "0" to a logic "1" value, flip-flop 1374 is clocked. A logic "0" value is input to D input of flip-flop 1374, because ACCR signal 1354 set the flip-flop 1374, so the $\overline{Q}$ output, which is fed back to the D input of the flip-flop, is a logic "0" value. The Q output of flip-flop 1374 is ACC0 signal 1304.

Since flip-flop 1374 was set, as described, the $\overline{Q}$ output having a logic "0" value is also input to the clock input of flip-flop 1376. Upon the clocking of flip-flop 1374, the $\overline{Q}$ output of that flip-flop will change from a logic "0" value to a logic "1" value, which will clock 1376 on the positive edge.

The $\overline{Q}$ output of flip-flop 1376 is fed back to the D input of that flip-flop. Since flip-flop 1376 was reset by ACCR signal 1354, a logic "1" value was input to the D input. On the clocking of flip-flop 1376, the Q output changes from a logic "0" output to a logic "1" value output which signal is ACC1 signal 1306.

It is ACC0 signal 1304 and ACC1 signal 1306 that are the control signals for determining which input to MUX 1318 (FIG. 22) will be output from the MUX as MRK F signal 1320. Before clocking, but after resetting of flip-flop 1374 and resetting of flip-flop 1376, ACC0 signal 1304 has a logic "1" value and the ACC1 signal 1306 has a logic "0" value.

Referring to FIG. 22, at the beginning of analog telemetry cycle. ACC0 signal 1384 has a logic "1" value which sets MUX 1308 and 1322. Therefore, the $D_1$ inputs are output from the respective MUX.

The ACC0 signal is also input to the MUX 1318, as one of the control signals. The second control signal for MUX 1318 is the ACC1 signal 1306, which has a logic value of "0" prior to clocking.

During analog telemetry of Sections 1 through 8, the stimulator will pace asynchronously at the basic rate. A TRV signal, which results in TRAV signal 812, causing clocking of the analog section flip-flops marks the end of each cycle.

When the analog counter reaches Section 8, both the ACC0 signal 1304 and the ACC1 signal 1306 have a logic "0" value. When this is the case, the $D_0$ input to each MUX is output from the respective MUX. (MUX 1308, MUX 1322, and MUX 1318)

The first seven sections of analog telemetry involve telemetering of internal measurements of the apparatus. During this period MEASCYC signal 1392 will have a logic "1" value. So it is only when TRAV signal 812 has a logic "1" value, that there be a logic "1" input to the D input to flip-flop 1372 to cause clocking. Because of asynchronous pacing during this part of analog telemetry, this will take place once per cycle when TRV signal with a logic "1" value occurs.

Referring to FIG. 23, upon entering of Section 8, flip-flop 1380 is clocked. Upon this clocking, the $\overline{Q}$ output changes from a logic "1" value to a logic "0" value. This logic "0" value is input to AND Gate 1382. This will cause the output of AND Gate 1382 to assume a logic "0" value. This logic "0" value is input to the D input of flip-flop 1384. After clocking of flip-flop 1384, the MEASCYC signal 1391 will change to a logic "0" value, which freezes the analog counter at Section 8 unless the counter is reset or indexing takes place.

Referring to FIG. 22, when the analog count is in Section 8, the markers channel will mark any events during the pacer cycle indicated in Table 8. In Section 8, ACC0 signal 1304 and ACC1 signal 1306 both have logic "0" values. This will mean that the $D_0$ input is output from MUX 1318 as MRK F signal 1320. The signal input of MUX 1318 is the output of OR Gate 1326. The inputs to OR Gate 1326 is TMIRT signal 622 and TRAREQ signal 808 as previously stated.

TMIRT signal 622 has a logic "1" value for a set time period after an IRW or TRV signal having a logic "1" value. When this happens, the output of OR Gate 1326 will assume a logic "1" value output which is input to the $D_0$ input of MUX 1318. This will cause MRK F signal 1320 to assume a logic "1" value and the appropriate analog value telemetered from the apparatus.

A TRA signal having a logic "1" value when input to OR Gate 1326 will cause its output to assume a logic "1" value. This logic "1" value is input to the $D_0$ input MUX 1318. This signal is MRK F signal 1320 and is telemetered from the apparatus.

Referring to FIG. 22, the only remaining signals which are detected and marked are SPW+SBP signal 500 and SRW signal 464. These signals when they have a logic "1" value, can result in MRK 8 signal 1328 having a logic "1" value. During Section 8, as stated, ACC0 signal 1304 has a logic "0" value. Therefore, the $D_0$ input to MUX 1322, which receives SPW+SBP signal 500, is provided as the output of the MUX. Although SPW+SBP signal 500 is being described, the description will also apply if SRW signal 464 is the signal output of MUX 1322 as MRK 8 signal 1328.

When an electrical activity is sensed on the P-channel, the logic value of SPW+SBP signal 500 will have a logic "1" value. If the activity on the P channel remains continuously for more than the 101.8 ms period of State A1, it is noise and no valid P-wave is was detected and SBP signal 448 will have a logic "1" value. This logic "1" value signal will be output from MUX 1322 as MRK 8 signal 1328.

Once telemetering has been accomplished, Section 8 is terminated by changing the logic value of ANALG signal 1302 from a logic "0" to a logic "1" and turning off the RF. At this point the apparatus will return to programmed pacing modality.

Figures 25, 26:
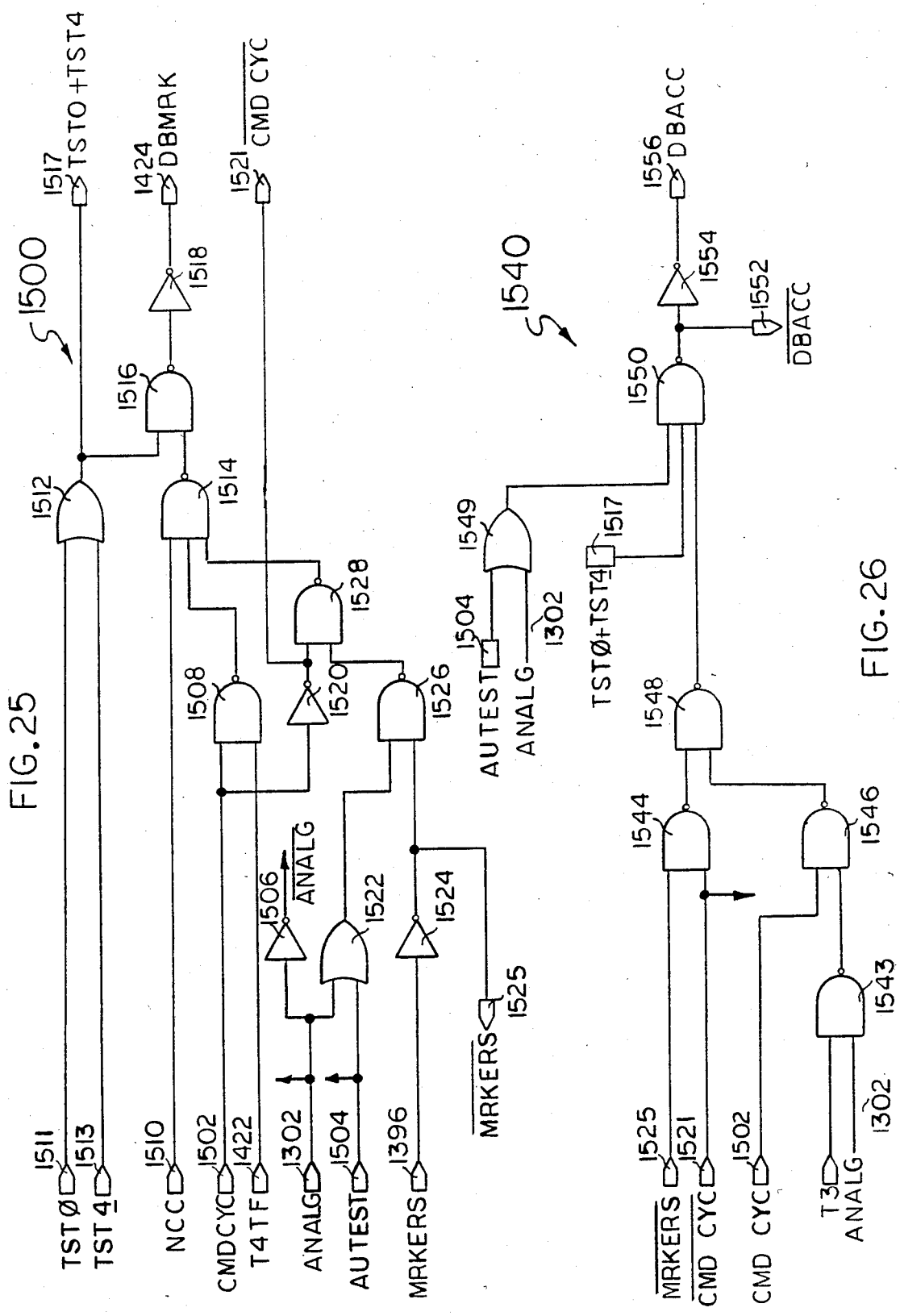
FIG. 25 shows the logic for generation of the DBMRK signal.
FIG. 26 shows the logic for generation of the DBACC signal.

When the analog section counter counts from Section 7 to Section 8, all of the flip-flops on the counter are clocked. Once in Section 8, in order for the markers to be telemetered, they must be put on an external bus comprised of external bus lines BX0; 704; BX1, 716; BX2, 160; and BX3, 630. These lines are used to transport the signals to a voltage controlled oscillator (VCO) (not shown) for telemetering. The logic circuitry for putting MRK F signal 1320 and MRK 8 signal 1328 on the external bus is shown in FIGS. 23, 25 and 26 and will be disclosed subsequently.

In order for markers to be put on the external bus, the analog count must be in Sections 8, 9, A, or B of analog telemetry.

For purposes of example, it is assumed the apparatus is in Section 8. Therefore, the method of putting MRK F signal 1320 and MRK 8 signal 1328 on the external bus will be disclosed.

Referring to FIG. 23, NOR Gate 1394 receives inputs from the Q output of flip-flop 1378 and the $\overline{Q}$ output of flip-flop 1380. In Section 8, the Q output of flip-flop 1378 has a logic "0" value and the $\overline{Q}$ output of flip-flop 1380 has a logic "0" value. Since both inputs have logic "0" values, the output of NOR Gate 1394 is a logic "1" value, which is MRKERS signal 1396. This signal is indicative of being in one of the MRKERS sections 8, 9, A or B.

Referring to FIG. 25, the external bus control signal DBMRK signal 1424, for putting markers on the bus, is shown generally at 1500. MRKERS signal 1396 is input to NAND Gate 1526 after passing through inverter 1524. Therefore, when the MRKERS signal 1396 has a logic "1" value in Section 8, a logic "0" value is input to NAND Gate 1526.

The second input to NAND Gate 1526 is the output of OR Gate 1522. The inputs to OR Gate 1522 are AUTEST signal 1504 and ANALG signal 1302. Since the apparatus is in Section 8 of the analog telemetry sequence, the ANALG signal 1302 has a logic "1" value and AUTEST signal 1504 has a logic "0" value because the ANALG and AUTEST cannot take place simultaneously. Therefore, the output of OR Gate 1522 is a logic "1" value which is input to NAND Gate 1526 as the first input.

The inputs to NAND Gate 1526 are a logic "1" value and a logic "0" value, so, the output of that Gate is a logic "1" value, which is input to NAND Gate 1528. The second input to NAND Gate 1528 is the CMDCYC signal 1502 after it passes through inverter 1520.

The CMDCYC signal 1502 has a logic "1" value during analog telemetry only when there is indexing. Since there is no indexing in Section 8, the CMDCYC signal has a logic "0" value. The output of NAND Gate 1528 is a logic "0" value because both inputs are logic "1" values. This logic "0" value is input to NAND Gate 1514 as the third input. The first input to NAND Gate 1514 is the NCC signal 1510 and the second inputs to the output of NAND Gate 1508.

The inputs to NAND Gate 1508 is CMDCYC signal 1502 which has a logic "0" value as previously described and T4TF signal 1422. T4TF signal 1422 is an output from the T counter (not shown). When the CMDCYC is a logic value "0", the T4TF signal has a logic "0" value. Since both of the inputs to NAND Gate 1508 are logic "0" values, the output of NAND Gate 1508 is a logic "1" value which is input to NAND Gate 1514 as the second input.

The first input to NAND Gate 1514 is the NCC signal 1510. This signal during analog telemetry is a logic "1" value. Since at least one input to NAND Gate 1514 is a logic "0" value, the output of NAND Gate 1514 is a logic "1" value, which is input to NAND Gate 1516 as a second input.

The first input to NAND Gate 1516 as the output of OR Gate 1512. The inputs to OR Gate 1512 are TST 0 signal 1511 and TST 4 signal 1513.

During analog telemetry the apparatus is pacing normally and is in the normal test state. Therefore, the TST 0 signal 1511 will have a logic "1" value. Since one of the inputs to OR Gate 1512 is a logic "1" value, the output of OR Gate 1512 is a logic "1" value which is input to NAND Gate 1516 as a first input.

Since both inputs to NAND Gate 1516 are logic "1" values, the output of NAND Gate 1516 is a logic "0" value, which is input to inverter 1518. The output of inverter 1518 is the compliment of the input, so the output is a logic "1" value, which is DBMRK signal 1424 for putting MRK F signal 1320 or MRK 8 signal 1328 on the external bus for telemetering from apparatus.

During analog telemetry when MRK F signal 1320 or MRK 8 signal 1328 are not being put on the external bus, because DBMRK signal 1424 does not have a logic "1" value, the analog section count is put on the external bus for telemetering from the apparatus. The signal for putting the analog count on the bus is DBACC signal 1556. This signal must have a logic "1" value to put the analog information on the data bus. The logic circuitry for the generation of DBACC signal 1556 is shown generally at 1540 in FIG. 26.

Referring to FIG. 26, when markers are not being used (i.e., not in sections 8, 9, A or B) $\overline{\text{MRKERS}}$ signal 1525 has a logic "1" value. This is indicative of the analog section being put on the bus. This logic "1" value for $\overline{\text{MRKERS}}$ signal 1556 is input to Gate 1544 as a first input. The second input to NAND Gate 1544 is $\overline{\text{CMDCYC}}$ signal 1521. The signal during analog telemetry without indexing is a logic "1" value. Since the inputs to NAND Gate 1544 are a logic "1" value and a logic "0" value, the output of NAND Gate 1544 is a logic "1", which is input to NAND Gate 1548 as the first input.

The second input to NAND Gate 1548 is the output of NAND Gate 1546. The inputs to NAND Gate 1546 are the outputs of AND Gate 1543 and CMDCYC signal 1502. The inputs to AND Gate 1543 are ANALG signal 1302 and T3 signal 1542 from the T counter (not shown). The ANALG signal has a logic "1" value as described. The T3 input has a logic value of "1" three clocks after resetting of the T counter. The counter is reset 3 clock periods after the first positive edge of RF data. This is the same RF signal used to initiate the analog sequence.

T3 signal 1542 is a logic "0" value until the T counter (not shown) counts out as described. Since one of the inputs to AND Gate 1543 is a logic "0" value, the output is a logic "0" value that is input to NAND Gate 1546 as the first input. The second input to NAND Gate 1546 is the CMDCYC signal 1502, which as described, has a logic "0" value. Both inputs to NAND Gate 1546 are logic "0" values, so, the output is a logic "1" value, which is input to NAND Gate 1548 as the second input.

Since both inputs to NAND Gate 1548 are logic "1" values, so, the output is a logic "0" value, which is input to NAND Gate 1550 as the third input. The second input to NAND Gate 1550 is TST 0+TST 4 signal 1517, which as described has a logic "1" value. The first input to NAND Gate 1550 is the output of OR Gate 1549, which has inputs of AUTEST signal 1504 and ANALG signal 1302. As described the AUTEST signal 1504 has a logic "0" value and the ANALG signal 1302 has a logic "1" value. Since one of the inputs has a logic value, the output of OR Gate 1549 is a logic "1" value.

All of the inputs to NAND Gate 1550 are logic "1" values, so, the output will be a logic "0" value. This value is input to inverter 1554. Inverter 1554 provides the compliment of the input as the output, so, the output is a logic "1" value, which is the DBACC signal 1556 for putting the analog sections on the external bus. The DBACC signal will have a logic "1" value during analog telemetry only when DBMRK sigal 1424 has a logic "0" value.

Referring to FIG. 23, in order to reach marker Section 9, Section A or Section B, INDEX signal 1352 must be used. The logic circuitry for the generation of INDEX signal 1352 is shown in FIGS. 27, 28 and 29.

Figure 29:
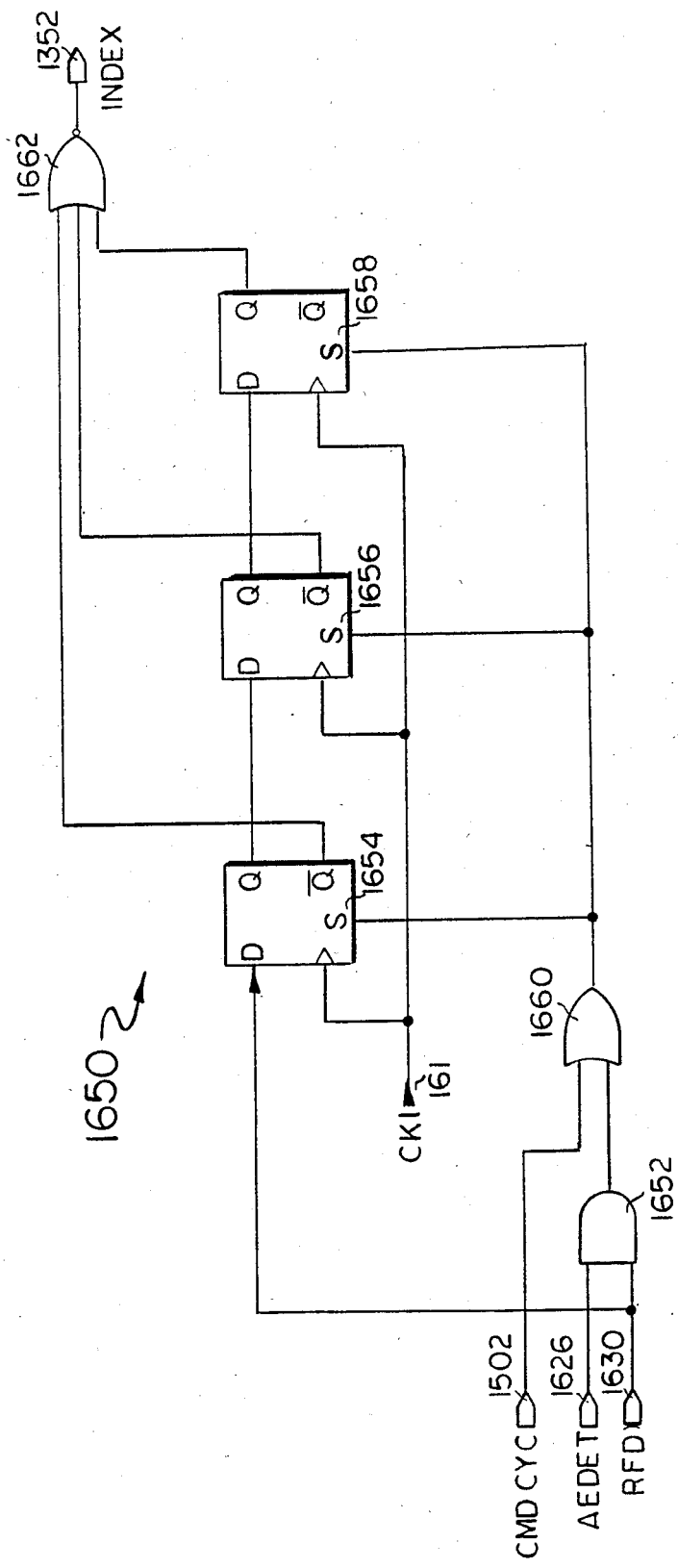
FIG. 29 shows the logic for generation of the INDEX signal for use in antitachycardia and analog sections for Markers.

In FIG. 29 three signals are used to generate INDEX signal 1352. These signals are AEDET signal 1626, RFD signal 1630 and CMDCYC signal 1502. Prior to describing the generation of INDEX signal 1352, the generation of AEDET signal 1626, and RFD signal 1630 will be described.

The CMDCYC signal 1502, as described previously, during telemetry of the marker sections has a logic "0" value. Therefore, the first input to OR Gate 1660 is a logic "0" value.

Figure 27:
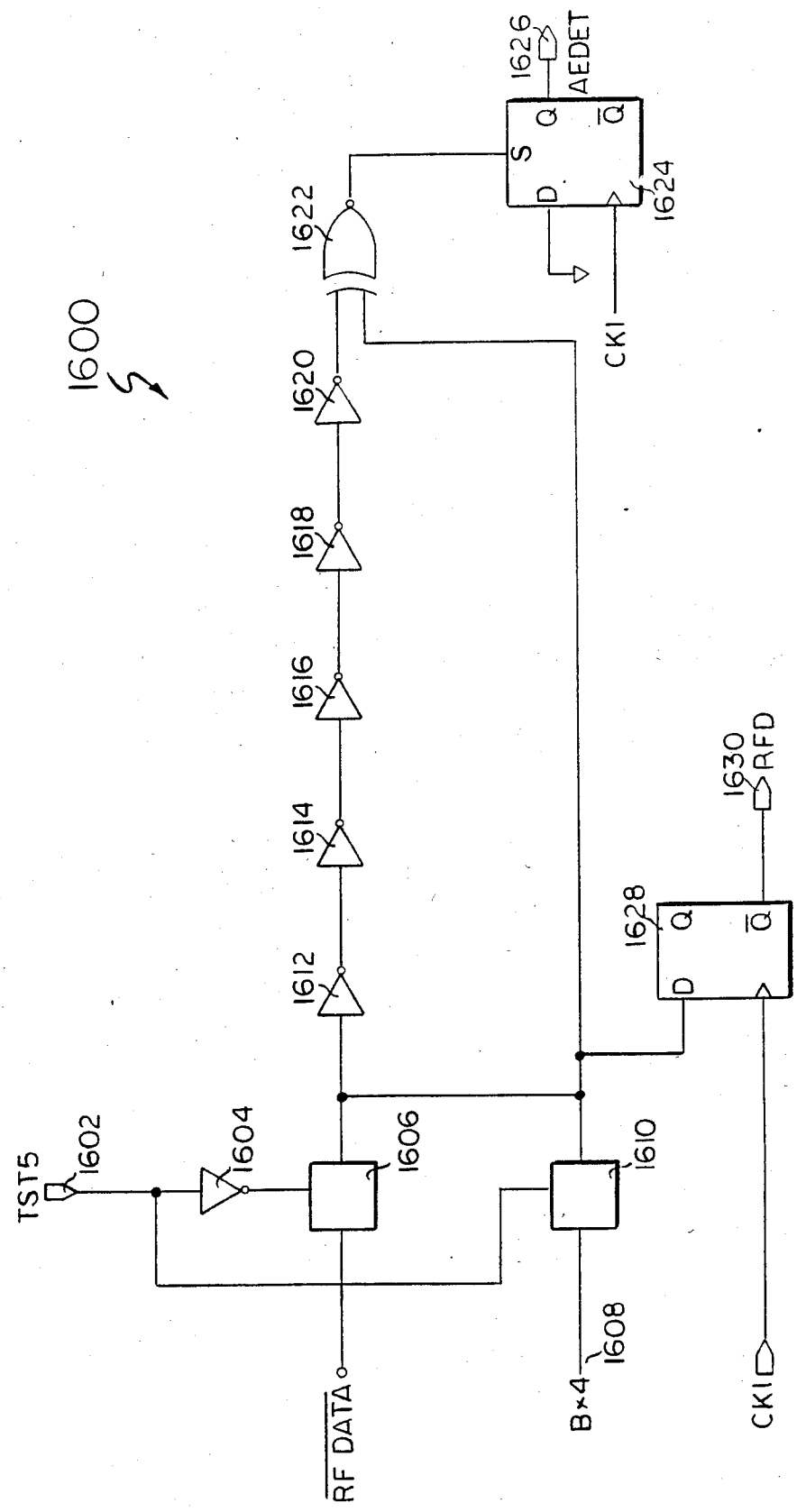
FIG. 27 shows the logic for generation of the RFD and AEDET signals.
Figure 28:
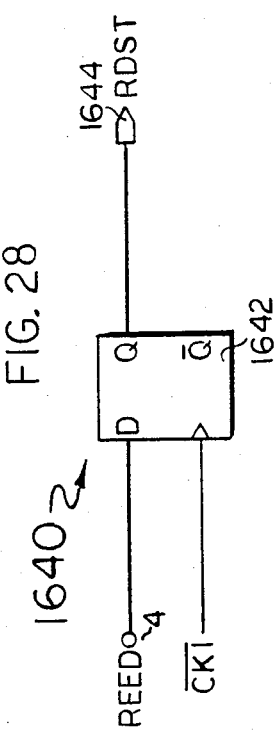
FIG. 28 shows the logic for generation of the RDST signal.

Referring to FIG. 27, the logic circuitry for the generation of RFD signal 1630 and AEDET 1626 are shown generally at 1600. When RF is turned on, $\overline{\text{RFDATA}}$ signal 2, having a logic "0" value, is input to transmission gate 1606. The control signal for transmission gate 1606 is TST 5 signal 1602. As described, during telemetry the test state the stimulator is in is TST 0. This logic "0" value of TST 5 signal 1602 is input to inverter 1604, so the output of the invertor is a logic "1" value. This logic "1" value turns transmission gate 1606 on and allows the logic "0" value of $\overline{\text{RFDATA}}$ signal 2 to be input to the D input of flip-flop 1628, to the plurality of inverters, and to XNOR Gate 1622.

When $\overline{\text{RFDATA}}$ signal is on, the logic value of the signal is "0". This logic value is input to the D input of flip-flop 1628. Flip-flop 1628 is used to synchronize the RF data signals with CK1 signal 161 and invert $\overline{\text{RFDATA}}$ signal 2. On clocking of flip-flop 1628, the compliment of the signal input to the D input will be output from the $\overline{\text{Q}}$ output of the flip-flop as RFD signal 1630.

AEDET 1626 is also dependent on $\overline{\text{RFDATA}}$ signal 2. $\overline{\text{RFDATA}}$ signal 2 is input to inverters 1612, 1614, 1616, 1618 and 1620. After $\overline{\text{RFDATA}}$ signal 2 is processed by the inverters, the opposite logic value is output by inverter 1620 as was input to inverter 1612. The signal output by invertor 1620 is input to XNOR Gate 1622 as a first input. The second input to XNOR Gate 1622 is $\overline{\text{RFDATA}}$ signal 2 which is not processed by the five inverters.

Since the first input to XNOR Gate 1622 is processed by the five inverters 1612, 1614, 1616, 1618 and 1620, its arrival at XNOR Gate 1622 is delayed. This delay in arrival of the first input to XNOR Gate 1622 will cause the inputs to XNOR Gate 1622 to be the same logic value until the delayed input arrives. This will mean XNOR Gate 1622 will have a logic "1" value output which will set flip flop 1624 for the remainder of the clock period in which there was a transition of the logic state of $\overline{\text{RFDATA}}$ signal 2. This logic "1" value will set flip-flop 1624 for a duration of the clock period when the termination took place and will be cleared out by the next clocking of the flip-flop.

Again referring to FIG. 29, the setting of flip-flop 1654, 1656 and 1658 will be described. AEDET signal 1626 and RFD signal 1630 are input to AND Gate 1652. When RFD signal 1630 and AEDET signal 1626 both have a logic "1" value, the output of AND Gate 1652 will assume a logic "1" value. This logic "1" value is input to OR Gate 1660, which will cause a logic "1" value output the OR Gate. This output is input to flip-flop 1654, 1656 and 1658 as a set term which will set the three flip-flops. Also when CMDCYC signal 1502 is a logic "1" value, it will cause setting of the three flip-flops.

INDEX signal 1352 is output from NOR Gate 1662. NOR Gate 1662 receives inputs from the three flip-flops. The inputs to NOR Gate 1662 are the $\overline{\text{Q}}$ output of flip-flop 1654, the $\overline{\text{Q}}$ output of flip-flop 1656 and the Q output of flip-flop 1658. INDEX signal 1352 is needed for reaching section 9 and subsequent sections of the Section 9 through E sequence. The output of NOR Gate 1662 will have a logic "1" value only when the $\overline{\text{Q}}$ output of flip-flop 1654 has a logic "0" value, the $\overline{\text{Q}}$ output of flip-flop 1656 has a logic "0" value and the Q output of flip-flop 1658 has a logic "0" value. The method of attaining these logic values will now be described.

When RF is turned off, RFD signal 1630 will have a logic "1" value for the remainder of the clock period when this event took place because the turning off of RF is asynchronous with the clock. AEDET signal 1626 has a logic "1" value during this same clock period because it detects the transition of the signal. When both RFD signal 1630 and AEDET signal 1626 have logic "1" values, flip-flops 1654, 1656 and 1658 will be set via AND Gate 1652 and OR Gate 1660. At this point INDEX signal 1352 will have a logic "0" value.

In order to achieve a logic "1" value for INDEX signal 1352, RF must first be turned off for a period of 8–42 ms and then back on. This is necessary to clear the set state of the flip-flops.

In order to produce INDEX signal 1352 with a logic "1" value, the timing of the generation of the RFD signal 1630 and AEDET signal 1626 when the RF is turned back on must be analyzed in greater detail. As previously stated, flip-flop 1628 synchronizes $\overline{\text{RFDATA}}$ signal 2 with the CK1 signal 161 and inverts the $\overline{\text{RFDATA}}$ signal 2. Therefore, RFD signal 1630 will always be synchronous with CK1. However, this is not true of AEDET signal 1626.

The AEDET signal 1626 will be generated by the asynchronous action of turning off or on RFDATA signal 2. The logic value of $\overline{\text{RFDATA}}$ signal 2 is transmitted through transmission Gate 1606 and input as the second input to XNOR Gate 1622. The first input to XNOR Gate 1622 is the inverted $\overline{\text{RFDATA}}$ signal 2 after passing through the five inverters 1612, 1614, 1616, 1618, and 1620. This will cause a time delay in the arrival of the second input signal to XNOR Gate 1622 as stated. Since the previous inverted logic value of the $\overline{\text{RFDATA}}$ signal 2 is still operative as the first input to XNOR Gate 1622, when the second input arrives at the gate, the output of the gate will be a logic "1" value, because both inputs have the same logic value. The duration of this logic "1" value from XNOR Gate 1622 will be until the arrival of the new first input signal due to the logic value change of RFDATA signal 2 after the time delay caused by the inverters.

This logic "1" value output is input to the set input of flip-flop 1624 and sets the flip-flop. Therefore, the Q output assumes a logic "1" value. This value is input to AND Gate 1652 (FIG. 29). The logic "1" value output of flip-flop 1624 will end at the beginning of the clock period after the flip-flop is set.

When RF is turned on after at least 8 ms., XNOR Gate 1622 will have a logic "1" value output, which will set flip-flop 1624, causing AEDET signal 1626 to have a logic "1" value for the clock period in which it was generated. This is because the activity of AEDET signal 1626 is asynchronous with CK1 signal 161. During the clock period RFD signal 1630 will have a logic "0" value. This logic "0" value is loaded into the D input of flip-flop 1654. However, flip-flops 1654, 1656 or 1658 will not be set because AND Gate 1652 has a logic "0" output. On the next clock, the RFD signal, which is output from the $\overline{Q}$ output of flip-flop 1628, assumes a logic "1" value and is synchronized with the clock. Simultaneously with the clocking of flip-flop 1628, flip-flop 1654 is clocked with a logic "0" value input to its D input.

Referring to FIG. 29, on the clocking of flip-flops 1628 and 1654, RFD signal having a logic "1" value and AEDET signal 1626 having a logic "0" value, are input to AND Gate 1652. Since there are logic "0" and "1" values input to the AND Gate, the output is a logic "0" value, which "0" value is input to OR Gate 1660. The other input to OR Gate 1660 is the CMDCYC signal 1502, which as described, is also a logic "0" value. Hence, again flip-flops 1654, 1656 or 1658 will not be set.

The three flip-flops, which ultimately determined INDEX signal 1352, will be set when there is noise in the RF data signal 2. This set of the flip-flops in the presence of noise in the RFD signal will be described before resuming the description of the generation of a logic "1" value INDEX signal.

If noise continues in the $\overline{\text{RFDATA}}$ signal 2 during off period, it will cause a logic "0" value input during the 8 ms. off period. So, RFD signal 1630 and AEDET signal 1626 will be logic "1" values at the same time (or point of clocking), thus causing a logic "1" value to be output of AND Gate 1652. This logic "1" value will be input to OR Gate 1660 and cause a logic "1" value output, which is input to the set inputs of flip-flops 1654, 1656 and 1658. This will set the three flip-flops and cause the inputs to NOR Gate 1662 to be a logic "0" value from flip-flop 1654; a logic "0" value from flip-flop 1656; and a logic "1" value from flip-flop 1658. Therefore, the output of NOR Gate 1662 will be a logic "0" value and cause blocking of INDEX signal 1352 in the presence of noise.

When there is no noise in the $\overline{\text{RFDATA}}$ signal 2 during the off period and the RF signal is turned on again, RFD signal 1630 will assume a logic "1" value. RFD signal 1620 with a logic "1" value is loaded into the D input of flip-flop 1654. Simultaneous with the clocking of the RFD signal, the logic "0" value previously input to the D input of flip-flop 1654 is clocked from the Q output of flip-flop 1654 and this is input to the D input of flip-flop 1656. RFD signal 1630 now having a logic "1" value is loaded into the D input of flip-flop 1654.

On the next clocking, the logic "0" value input to the D input of flip-flop 1656 is clocked and the Q output assumes a logic "0" value, which is loaded into the D input of flip-flop 1658. The logic "1" value input to the D input of flip-flop 1654 is clocked and the Q output of that flip-flop assumes a logic "1" value and is loaded into the D input of flip-flop 1656. The logic "1" value of the RFD signal 1630 is loaded into the D input of flip-flop 1654.

On the third clocking after the RF is turned on, the logic "0" value loaded into the D input of flip-flop 1658 is output from the Q output of that flip-flop and is input to a first input to NOR Gate 1662. The logic "1" value input to the D input of flip-flop 1656 is output from the Q output of the flip-flop. The $\overline{Q}$ output of flip-flop 1656 assumes a logic "0" value, when the Q output assumes a logic "1" value output. The $\overline{Q}$ output of flip-flop 1656 having a logic "0" value is input to NOR Gate 1662 as the second input. The logic "1" value input to the D input of flip-flop 1654 is output from the Q output of that flip-flop and the $\overline{Q}$ output assumes a logic "0" value. The logic "0" value of the $\overline{Q}$ output is input to NOR Gate 1662 as the third input.

Therefore, the third clock pulse after the RF is turned on all of the inputs to NOR Gate 1662 will be a logic "0" value, which causes the output of NOR Gate 1662 to assume a logic "1" value, which is INDEX signal 1352.

Once INDEX signal 1352 having a logic "1" value is generated, CMDCYC signal will assume a logic "1" value and set all of three flip-flops. This condition will hold the flip-flops set until that signal is cleared out by the RF being turned off.

Referring to FIG. 23, when INDEX signal 1352 has a logic "1" value, it will set flip-flop 1380. INDEX signal 1352 is also the second input to NAND Gate 1360 as previously described. Once the apparatus is advanced to Section 8 the apparatus no longer paces asynchronously as in Sections 1–7 but operates in the programmed pacing modality.

The first input to NAND Gate 1360 is ANALG signal 1302, which as described, has a logic "1" value during analog telemetry. Since both of the inputs to NAND Gate 1360 are a logic "1" value, the output is a logic "0" value, which is input to NAND Gate 1362 as the second input.

The first input to NAND Gate 1362 is the output of NAND Gate 1358. The output of NAND Gate 1358 is a logic "1" value during Section 8 because MEASCYC signal 1392 is a logic "0" value. Since the inputs to NAND Gate 1362 are a logic "1" and a logic "0" value, the output is a logic "1" value, which is input to the tied inputs of NOR Gate 1366, causing its output to assume a logic "0" value. This logic "0" value is input to NOR Gate 1368 as the second input. The first input is TACH Signal 1364 which has a logic "0" value. Since both inputs are logic "0" values, the output is a logic "1" value which is input to the D input of flip-flop 1372. On the next clock, this logic "1" value is clocked and the Q output of that flip-flop assumes a logic "1" value. This logic value is input to clock input of flip-flop 1374 which causes clocking of it on the same clock, therefore, advancing the analog counter to Section 9.

Referring to FIG. 22, in Section 9, ACC0 signal 1304 has a logic "1" value and ACC1 signal 1306 has a logic "0" value. These values, which are input to the control inputs to MUX 1318, cause the input $D_1$ to be output from the MUX. Also, since ACC0 signal 1304 has a logic "1" value it will set MUX 1308 and MUX 1322. This will cause the $D_1$ input to both MUX to be output from the respective MUX.

In the dual chamber modes of operation, TRV signals and IRW signals will be input to MUX 1318 through TMIRT signal 622. These signals will be telemetered as MRK F. IPW signals and TRA signals will not be telemetered unless the apparatus is operating in a single chamber atrial modality.

Because ACC0 signal 1304 is a logic "1" value, MUX 1322 is set as stated. When the SRW signal has logic "1" value, it is input to the $D_1$ input of MUX 1322. SRW signal 464 will be telemetered as MRK 8 signal 1328 from the apparatus. The signal is telemetered at the $V_{ref}$ amplitude and has a duration of the sensed R-wave.

Again referring to FIG. 23, when the analog counter is in Section 9, the inputs to NOR Gate 1394 are the ACC2 signal output from the Q output of flip-flop 1378 and the $\overline{Q}$ output of flip-flops 1380. Since both of these inputs are logic "0" values the output is a logic "1" value. Therefore, the MRKERS signal 1396 has a logic "1" value.

MRK 8 signal 1328 and MRK F signal 1320 can only be put on the external bus of the apparatus for telemetering from the apparatus when DBMRK signal 1424 has a logic "1" value which is input to control input of QUAD transmission gate 1438.

The remaining marker sections for telemetering from the stimulator are Sections A and B. When the stimulator is indexed, a second and subsequent a third time, sections A and B are entered, respectively. In Section A, ACC0 signal changes from a logic "1" value to a logic "0" value, and the ACC1 signal changes from a logic "0" value to a logic "1" value. These signals are input to FIG. 22 as control inputs to MUX 1318 and causes the $D_2$ input to be output from the MUX. As stated ACC0 signal 1304 has a logic "0" value, so the $D_0$ inputs of MUX 1308 and 1302 are connected to the respective D outputs.

When in Section B, ACC0 signal 1304 has a logic "1" value and ACC1 signal 1306 has a logic "1" value. When these signals are input as control signals to MUX 1318, they cause input $D_3$ to be output from that MUX. Also, MUX 1308 and 1322 are set and their respective $D_1$ inputs are output from each MUX.

Referring to FIG. 22, when PWT signal 442 or a RWT signal 466 are sensed in Sections A and B, respectively, they cause the output of MUX 1308 to have a logic "1" value, which is input to AND Gate 1310. During analog telemetry, ANALG signal has a logic "1" value, so the output of AND Gate 1310 will be a logic "1" value. This logic "1" value output is input as a second input to NOR Gate 1312 of asynchronous latch consisting of NOR Gate 1312 and NOR Gate 1314. The first input to NOR Gate 1312 is the feedback from the output of NOR Gate 1314, which is initially a logic "0" value. When the inputs are a logic "1" and a logic "0" value, the output of NOR Gate 1312 is a logic "0" value, which is input to NOR Gate 1314 as a first input. The second input to NOR Gate 1314 is CK1 signal 161. When the logic value of CK1 signal 161 is a logic "0" the output of NOR Gate 1314 is a logic "1" value which is input to the D input flip-flop 1316. This logic "1" value is also fed back to the input of NOR Gate 1312 as stated. On the next clock pulse the logic "1" value will be input to the $D_2$ and $D_3$ inputs of MUX 1318 and dependent on the section, (Section A or B) the output from the MUX will be connected to one of the outputs.

When the apparatus is in Section 8 or A, the output of MUX 1322 assumes the logic value of SPW+SBP signal 500. When it is in Section 9 or B, the output of MUX 1322 assumes the logic value of SRW signal 464. The signals which are output from the D output of MUX 1322 are MRK 8 signal 1328. These signals will be generated only when the refractory periods of the B and C timers permit. However, if SPW+SBP 500 or SRW 464 signal take place at the proper time, they could be telemetered as the MRK 8 signal 1328 in competition with the MRK F signal 1320.

PWT signal 442 and RWT signal 460, which result in MRK F signal 1320 are delayed by one clock period by flip-flop 1316. Since SPW signal 500 and SRW signal 464 are delayed by flip-flops 418 and 432 (FIG. 9), respectively after sensing, both MRK F signal 1320 and MRK 8 signal 1328 will be generated on the same clocking. The logic is set up so that MRK F signal 1320 will dominate MRK 8 signal 1328 when the apparatus is in Sections A or B. Therefore, PWT signal 442 and RWT signal 466 which make up MRK F signal 1320 will dominate the SPW+SBP signal 500 or SRW signal 464 when they are clocked at the same time.

When it is determined that analog telemetry is no longer desired, the ANALG signa 1302 has a logic "0" value, telemetry from the apparatus is ceased and RF is turned off.

ANTITACHCARDIA MODES

The apparatus of invention incorporates temporary antitachycardia modalities to break tachycardias. These modalities are directed to preventing tachycardias in either the atrium or ventricle. The antitachycardia modalities are used in conjunction with the marker channels to break tachycardias.

When the antitachycardia modalities are programmed, they are not self-actuating or automatically operable in the event of an atrial or ventricular tachycardia. These modalities are set in the programming and are operable upon activation by an external device (not shown). The device, which activates the antitachycardia modalities, is the general programming device for the apparatus. However, in any case, the antitachycardia modalities must have been programmed in the stimulator.

The triggering mechanism for the antitachycardia modes is an RF burst for a measured period of time followed by an off period. Once triggered, the stimulator will provide a pacer derived pulse each time there is the generation of TACH-TRIG signal 162 (FIG. 8). This signal will provide an apparatus output to the atrium or ventricle dependent on the modality programmed.

When one of the antitachycardia modalities are desired to be used, the stimulator ANALG signal 1356 has a logic "1" value. In most cases the analog counter is indexed to Section C or D which provides ECG (electrocardiogram) signals from the P and R-wave channels of the apparatus. Once one of the ECG sections for analog telemetry have been entered, the antitachycardia command is given to the pacer by an external device (not shown). The external device provides the antitachycardia commands via $\overline{\text{RFDATA}}$ signal 2 in a command format. The stimulator will pace the appropriate chamber in accordance with the command format.

The RF burst which is used for generation of the pacing pulse must be 25 to 42 ms wide and then must be at least an 8 ms. of off period between bursts. These bursts must occur at the basic rate or more often. If they do not, the temporary antitachycardia modality will be dropped and the previous modality will be resumed.

The operative portions of the digital logic for the antitachycardia modalities are shown in FIGS. 8A, 8B, 14, 27, 28, 29 and 30. There are two antitachycardia modalities. The two are the ATACH and VTACH, previously described.

Whenever the antitachycardia modality to be used, it must be programmed into memory. The programming for the antitachycardia modalities allow for either doctor or patient activated antitachycardia operation.

Figure 30:
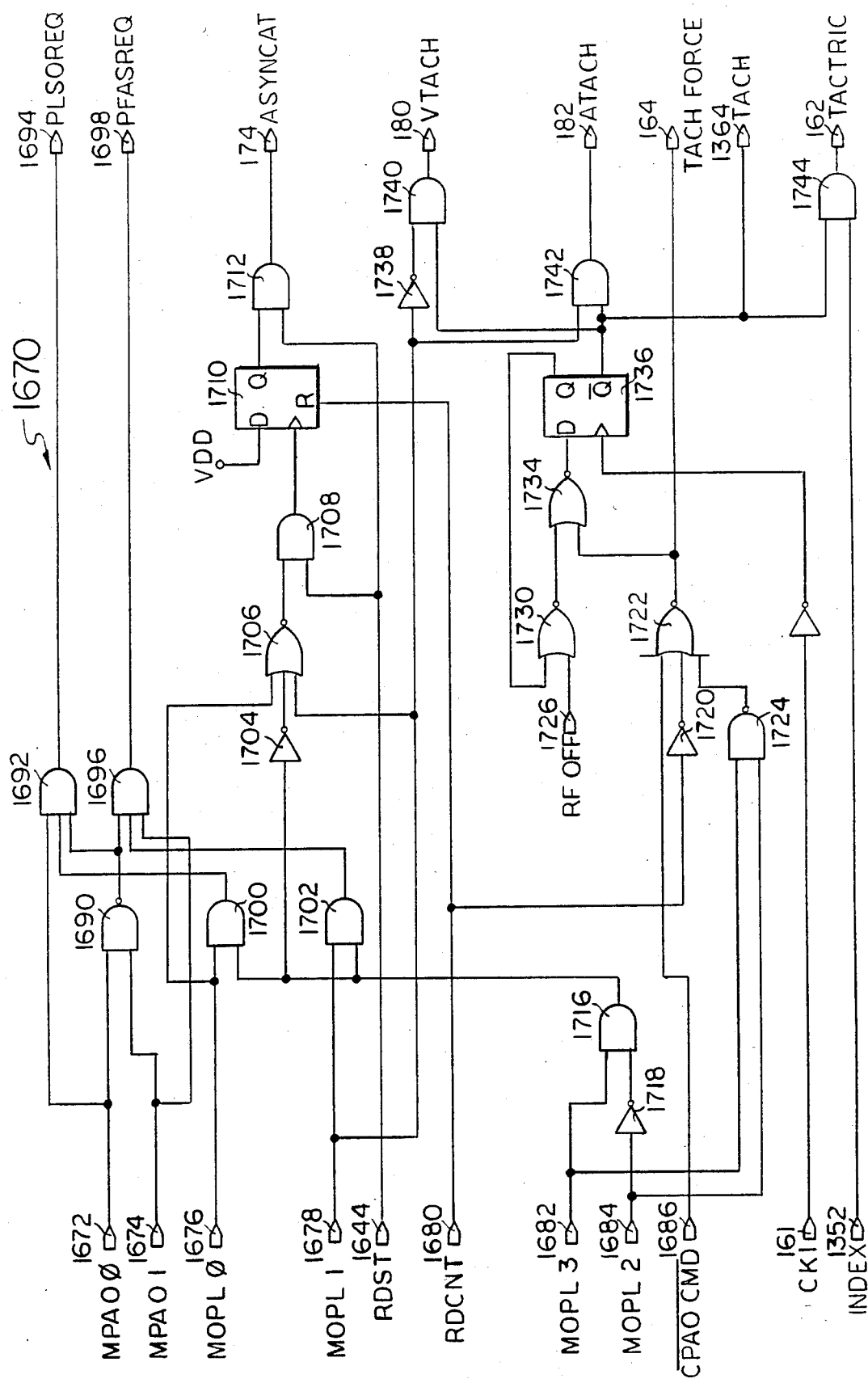
FIG. 30 shows the logic for generation of the signals for use in the antitachycardia modalities.

Referring to FIG. 30 generally shown at 170, the antitachycardia modalities are operative through the memory cells having MPAO 0-1 logic values and MOPL0-3 logic values. In order to be able to enter the antitachycardia modalities MPAO-0 signal 1672 must have a logic "1" value, MPAO-1 signal 1674 must have a logic "1" value, MOPL-0 signal 1676 can be either logic "1" or "0" value; MOPL-1 signal 1678 must be a logic "1" value for RF activated atrial antitachycardia and logic "0" value for RF activated ventricular antitachycardia; MOPL-2 signal 1684 must be a logic "1" value for both RF atrial and ventricular antitachycardia; and MOPL-3 signal 1682 must be a logic "1" value for both atrial and ventricular antitachycardia.

For purposes of explanation, the activation of the ventricular antitachycardia system will be disclosed. The atrial antitachycardia systems is identical to the ventricular system, except that a TRA is produced instead of a TRV.

When the above described logic values for MOPL 0-3 are programmed in memory, they are input as 1676, 1678, 1684 and 1682, respectively. The above described logic values for MPAO 0 and 1 are input as 1672 and 1674, respectively.

When patient activated antitachycardia is desired, the MPAO-0 signal 1672 and MPAO-1 signal 1674 programming is important. The logic "1" values of MPAO-0 signal 1672 and MPAO-1 signal 1674 are input to NAND Gate 1690. When both the input logic values are a logic "1" value, the output is a logic "0" value, which is input as a first input to NOR Gate 1722.

The second input to NOR Gate 1722 is $\overline{\text{CPAOCMD}}$ signal 1686. This is a negative true signal to strobe the patient option activate command. The logic value of this signal is a logic "0" value, when the patient activation is accomplished through a proper command to the apparatus. Therefore assuming this command is given a logic "0" value is the second input to NOR Gate 1722.

The third input to NOR Gate 1722 is RDCNT signal 1680, after it passes through invertor 1720. This signal has a logic "1" value during normal antitachycardia activation. Therefore, a logic "0" value is input to NOR Gate 1722 as the third input.

The fourth input to NOR Gate 1722 is the output of NAND Gate 1724. The inputs to this Gate are MOPL-2 signal 1684 and MOPL-3 signal 1682. As previously stated, the logic values of these signals are logic "1" values. Since both inputs are a logic "1" value the output is a logic "0" value, which is input to NOR Gate 1722.

All of the inputs to NOR Gate 1722 are logic "0" values, so, the output of NOR Gate 1722 is a logic "1" value, which input is a second input to NOR Gate 1734. The first input to NOR Gate 1734 is the output of NOR Gate 1730. There are two inputs to NOR Gate 1730. The first input is the signal feedback from the Q output of flip-flop 1736 which normally has a logic "1" value. NOR Gates 1730 and 1734; and flip-flop 1736 form a clocked set/reset latch.

The second input to NOR Gate 1730 is the RFOFF signal 1726. When the RF is turned on, the signal has a logic "0" value. When this is the case, the inputs to NOR Gate 1730 is a logic "1" value and a logic "0" value. So, the output of that gate is a logic "0" value which is input to NOR Gate 1734.

When the output of NOR Gate 1722 assumes a logic "1" value, as described, and input to NOR Gate 1734, the output of NOR Gate 1734 assumes a logic "0" value which is input to the D input of flip-flop 1736. On the next positive edge of $\overline{\text{CK1}}$ signal 167, the $\overline{\text{Q}}$ output of the flip-flop will assume a logic "1" value. This value is input to AND Gates 1740 and 1742 to enable VTACH signal 180 and ATACH signal 182 to have a logic "1" value.

When the RF is on, RDCNT signal has a logic "1" value for 1 clock period. When the antitachycardia modality is to be entered, the RF signal will be decoded and $\overline{\text{CPAOCMD}}$ signal will have a logic "0" value. This will cause the output of NOR Gate 1722 to assume a logic "1" value, which is input to NOR Gate 1734. This logic "1" value output is also TACH FORCE signal 164, which is input to FIG. 8A and causes, in FIG. 9A, the IRW signal 464 to remain at a logic "1" value and reset timing.

When the logic "1" value is input to NOR Gate 1734, the output changes from a logic "1" value to a logic "0" value. This logic "0" value is input to the D input of flip-flop 1736. On the next clock the Q output of flip-flop 1736 will assume a logic "0" value and the $\overline{\text{Q}}$ output a logic "1" value. The Q output is fed back to NOR Gate 1730 as an input and changes the output of that gate to a logic "1" value, which is input to NOR Gate 1734. Because of this change in the logic value of NOR Gate 1730, the output of NOR Gate 1734 will remain a logic "0" value until there is a change in the logic value of the output of NOR Gate 1722.

The $\overline{Q}$ output of flip flop 1736, having a logic "1" value is input to three AND Gates. These gates are AND Gate 1740, AND Gate 1742 and AND Gate 1744. The second input to AND Gate 1740 is MOPL-1 signal 1678, which as described has a logic "0" value. This signal is input to AND Gate 1740 after it passes through inverter 1738, the compliment of the MOPL-1 signal thereby being provided as an input to AND Gate 1740. Both inputs to AND Gate 1740 are a logic "1" value so the output of AND Gate 1740, which is VTACH signal 180 is a logic "1" value. This VTACH signal 180 is input to the mode section of the PGSL (FIG. 8A).

MOPL-1 signal 1678 is also input as the second input to AND Gate 1742, however, it does not pass through inverter 1738. Therefore, the logic "0" value of that signal is provided to AND Gate 1742 as the second input. The inputs to AND Gate 1742 are a logic "1" and a logic "0" value so the output of that gate, which is ATACH signal 182, is a logic "0" value. ATACH signal 182 having a logic "0" value is input to the mode section of the PGSL (FIG. 8A).

The third AND Gate, Gate 1744 has as its second input INDEX signal 1352. Referring to FIGS. 27 and 29, the generation of INDEX signal 1352 is shown. Therefore, once the apparatus is in one of the antitacycardia modalities, the delivery of a stimulation pulse is dependent on the generation of INDEX signal 1352, as will be described.

Referring to FIG. 23, the $\overline{Q}$ output of flip-flop 1736 is also TACH signal 1364, which is input to NOR Gate 1368. When TACH signal 1764 has a logic "1" value, the output of NOR Gate 1368 will be a logic "0" value. This prevents the changing of analog sections when INDEX signals are used to produce stimulation pulses in accordance with the antitachyardia modality. If this were not the case, the generation of an INDEX signal would cause indexing of the analog counter to the next analog section as previously described for markers. In producing the INDEX signals, the RF must be off for a period of 8 ms. to 42 ms. and then turned on.

Again referring to FIG. 30, when INDEX signal 1352 has a logic "1" value and the $\overline{Q}$ output of flip-flop 1736 has a logic "1" value, the output of AND Gate 1744, which is TACTRIG signal 162, is a logic "1" value. This TACTRIG signal 162 is input to the mode section of the PGSL (FIG. 8A).

When Command State RFOFF 1726 is set, the logic value of the signal is a logic "1" value. When it is not operative, it is a logic "0" value. Since the feedback signal from flip-flop 1736 has a logic "1" value the output of NOR Gate 1730 is a logic "0" value, regardless of the RF State. However, once the latch has been set by the logic value of NOR Gate 1722, changing from a logic "0" value to a logic "1" value, INDEX signal 1352 will determine whether a stimulator pulse will be output from the apparatus. This is because INDEX signal 1352 will cause a logic "1" value TACTRIG signal under these conditions.

Referring to FIG. 8A, TACTRIG signal 162 is input to NAND Gate 224. The second input to NAND Gate 224 is $V_{dd}$. The output of NAND Gate 224, which is $\overline{TRIG}$ signal 338, will have a logic "0" value, whenever TACTRIG signal 162 has a logic "1" value.

$\overline{TRIG}$ signal 338 with a logic "0" value is input to NAND Gate 766 (FIG. 14). Since the logic value is "0", the output of NAND Gate 766 is a logic "1" value regardless of the logic value of the other inputs. This logic "1" value output from NAND Gate 766 is input to the D input of flip-flop 768. On the positive edge of $\overline{CK1}$ signal 167, the Q output of this flip-flop will assume a logic "1" value, which is TRV signal for producing a TRV stimulation pulse.

Referring to FIG. 8A, the VTACH signal 180 is input to NOR Gate 204, NOR Gate 208, NOR Gate 212, and NOR Gate 220. This will cause the outputs of the four NOR Gates to assume a logic "0" value. This will cause the data inputs $D_0$–$D_3$ to QUAD latch 238 to latch values that are indicative of the VVI pacing modality. Therefore, RXOVER signal 358 will be a logic "0" value.

If ATACH signal 182 is a logic "1" value, the mode section will latch $D_0$–$D_3$ inputs indicative of the AAI pacing modality. This will also cause RXOVER signal 358 to assume a logic "1" value for crossing over the output from a TRV to TRAREQ line.

The terms and expressions which are employed here are used as terms of description and not of limitation and there is no intention in the use of such terms and expressions of excluding equivalents of the features shown and described, or portions thereof, it being recognized that various modifications are possible within the scope of the invention as claimed.

We claim:

1. A programmable apparatus for cardiac stimulation comprising:
   a first sensing means for sensing electrical activity in a first area of tissue;
   a second sensing means for sensing electrical activity in a second area of tissue;
   a pulse generating timing means connected to said first and second sensing means response to electrical activity sensed in said first and second area of tissue respectively for defining a stimulation cycle and for determining the timing for supplying electrical pulses within said stimulation cycle to said first and second areas of tissue for respective depolarization of said first and second areas of tissue;
   pulse generating means responsive to said pulse generating timing means for generating stimulating pulses that are selectively delivered to said first and second areas of tissue; and
   circuit means for inhibiting the operation of said first sensing means for the duration of the stimulation cycle whenever premature electrical activity is sensed in said second area of tissue by said second sensing means prior to one of a set of prescribed events, said set of prescribed events comprising: (1) the sensing of electrical activity by said first sensing means in said first area of tissue during said stimulation cycle, and (2) the generating of a stimulation pulse by said pulse generating means for delivery to said first area of tissue during said stimulation cycle.

2. The apparatus as recited in claim 1 wherein said first area of tissue includes cardiac atrial tissue and said second area of tissue includes cardiac ventricular tissue, and further wherein said pulse generating means includes electrical leads for connecting said atrial and ventricular tissue with said cardiac stimulation apparatus.

3. The apparatus as recited in claim 2 wherein the apparatus further comprises at least a first (A), second (B), and third (C) timing means for interaction with said pulse timing means, and wherein said first timing means (A) comprises a first timer that defines a sampling period during which naturally occurring depolarization of atrial or ventricular tissue, resulting in P-Waves or R-waves, respectively, must occur if said P-Waves or R-waves are to be considered as being sensed by said pulse generating timing means; said second timing means (B) comprises a second timer that defines the stimulation cycle of the apparatus; and said third timing means (C) comprises a third timer that defines an absolute refractory period, a relative refractory period, and a maximum track rate period during a stimulation cycle of the second timing means.

4. The cardiac pacemaker of claim 1 wherein said prescribed atrial activity comprises the providing of a stimulation pulse to the atrium.

5. In a multi-mode cardiac pacemaker that selectively provides operating modalities of at least DVI and DDD, said DVI operating mode including means for selectively providing stimulation pulses to both the atrium and ventricle of a heart, means for sensing naturally occurring electrical activity in the ventricle, and means for inhibiting stimulation pulses in the presence of naturally occurring electrical activity; said DDD operating mode including said means for selectively providing stimulation pulses to both the atrium and ventricle of a heart, means for sensing naturally occurring electrical activity in both the atrium and ventricle, and said means for inhibiting stimulation pulses in the presence of naturally occurring electrical activity; an additional pacing modality of DDX comprising:

said means for selectively providing stimulation pulses to both the atrium and ventricle of a heart;

said means for sensing naturally occurring electrical activity in both the atrium and ventricle;

circuit means responsive to said means for sensing naturally occurring electrical activity for signaling the occurrence of premature electrical activity sensed in the ventricle of the heart; and control means for causing said cardiac pacemaker to operate in said DDD operating mode in the absence of premature electrical activity as signaled by said circuit means and for causing said cardiac pacemaker to operate in said DVI operating mode in the presence of premature electrical activity as signaled by said circuit means.

6. The cardiac pacemaker of claim 4 wherein said circuit means signals the occurrence of premature electrical activity whenever electrical activity is sensed in the ventricle of the heart subsequent to previously sensed ventricular electrical activity but prior to prescribed atrial activity.

7. The cardiac pacemaker of claim 5 wherein said prescribed atrial activity includes naturally occurring electrical activity sensed in the atrium.

* * * * *